US012629410B2

(12) United States Patent
Rice et al.

(10) Patent No.: US 12,629,410 B2
(45) Date of Patent: May 19, 2026

(54) MULTI-ANTIGENIC PEPTIDE MIMICS OF GONOCOCCAL LIPO-OLIGOSACCHARIDE (LOS) EPITOPES

(71) Applicant: University of Massachusetts, Boston, MA (US)

(72) Inventors: Peter A. Rice, Worcester, MA (US); Michael W. Pennington, Worcester, MA (US); Sunita Gulati, Worcester, MA (US); Jutamas Shaughnessy, Worcester, MA (US); Sanjay Ram, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 799 days.

(21) Appl. No.: 17/762,159

(22) PCT Filed: Sep. 22, 2020

(86) PCT No.: PCT/US2020/052057
§ 371 (c)(1),
(2) Date: Mar. 21, 2022

(87) PCT Pub. No.: WO2021/061676
PCT Pub. Date: Apr. 1, 2021

(65) Prior Publication Data

US 2022/0395567 A1 Dec. 15, 2022

Related U.S. Application Data

(60) Provisional application No. 62/903,963, filed on Sep. 23, 2019.

(51) Int. Cl.

| | |
|---|---|
| ***A61K 38/00*** | (2006.01) |
| ***A61K 39/095*** | (2006.01) |
| ***A61P 31/04*** | (2006.01) |
| ***C07K 7/64*** | (2006.01) |
| ***C07K 14/22*** | (2006.01) |
| *A61K 39/00* | (2006.01) |

(52) U.S. Cl.
CPC ............ *A61K 39/095* (2013.01); *A61P 31/04* (2018.01); *C07K 7/64* (2013.01); *C07K 14/22* (2013.01); *A61K 39/00* (2013.01); *A61K 2039/6031* (2013.01)

(58) Field of Classification Search
None
See application file for complete search history.

(56) References Cited

U.S. PATENT DOCUMENTS 7,189,405 B1 * 3/2007 Rice ..................... A61K 39/095 424/193.1

FOREIGN PATENT DOCUMENTS

| | | |
|---|---|---|
| EP | 20867242.8 | 12/2023 |
| WO | WO 01/32692 A2 | 5/2001 |

OTHER PUBLICATIONS

Martinho et al. (Int. J. Nanomedicine. 2017 25; 12: 7053-7073). Rational design of novel, fluorescent, tagged glutamic acid dendrimers with different terminal groups and in silico analysis of their properties (Year: 2017).*

Ngampasutadol et al. (Vaccine 24 (2006) 157-170). Characterization of a peptide vaccine candidate mimicking an oligosaccharide epitope of Neisseria gonorrhoeae and resultant immune responses and function (Year: 2006).*

Extended European Search Report for EP Application No. 20867242.8 dated Dec. 11, 2023.

Gulati et al., Targeting Lipooligosaccharide (LOS) for a Gonococcal Vaccine. Front Immunol. Feb. 27, 2019;10:321. doi: 10.3389/fimmu.2019.00321.

Gulati et al., Immunization against a saccharide epitope accelerates clearance of experimental gonococcal infection. PLoS Pathog. 2013;9(8):e1003559. doi: 10.1371/journal.ppat.1003559. Epub Aug. 29, 2013.

Invitation to Pay Additional Fees for Application No. PCT/US2020/052057, mailed Dec. 8, 2020.

International Search Report and Written Opinion for Application No. PCT/US2020/052057, mailed Feb. 11, 2021.

International Preliminary Report on Patentability for Application No. PCT/US2020/052057, mailed Apr. 7, 2022.

Hua et al., Preparation and properties of EDC/NHS mediated crosslinking poly (gamma-glutamic acid)/epsilon-polylysine hydrogels. Mater Sci Eng C Mater Biol Appl. Apr. 1, 2016;61:879-92. doi: 10.1016/j.msec.2016.01.001. Epub Jan. 6, 2016.

Martinho et al., Rational design of novel, fluorescent, tagged glutamic acid dendrimers with different terminal groups and in silico analysis of their properties. Int J Nanomedicine. Sep. 25, 2017;12:7053-7073. doi: 10.2147/IJN.S135475.

(Continued)

*Primary Examiner* — Lianko G Garyu
*Assistant Examiner* — Mercy H Sabila
(74) *Attorney, Agent, or Firm* — Wolf, Greenfield & Sacks, P.C.

(57) ABSTRACT

In some aspects, the disclosure relates to compositions of peptide mimics useful in the treatment of *Neisseria gonorrhoeae* (*N. gonorrhoeae*). In some embodiments, the peptide mimics are multi-antigenic molecules of a conserved gonococcal lipo-oligosaccharaide (LOS) epitope. In some aspects, the disclosure relates to methods of making peptide mimics for the treatment of *N. gonorrhoeae*. In some aspects, the disclosure relates to methods of using peptide mimics for the treatment of *N. gonorrhoeae*.

2 Claims, 21 Drawing Sheets

Specification includes a Sequence Listing.

(56) References Cited

OTHER PUBLICATIONS

Ngampasutadol et al., Characterization of a peptide vaccine candidate mimicking an oligosaccharide epitope of Neisseria gonorrhoeae and resultant immune responses and function. Vaccine. Jan. 12, 2006;24(2):157-70. doi: 10.1016/j.vaccine.2005.07.065. Epub Aug. 10, 2005.
Partial European Search Report for Application No. 20867242.8, mailed Sep. 27, 2023.
Wischnjow et al., Renal Targeting: Peptide-Based Drug Delivery to Proximal Tubule Cells. Bioconjug Chem. Apr. 20, 2016;27(4):1050-7. doi: 10.1021/acs.bioconjchem.6b00057. Epub Mar. 30, 2016.

* cited by examiner

1 Det A Ch1 / 220nm

PeakTable

Detector A Ch1 220nm

| Ret. Time | Area | Height | Area % |
|---|---|---|---|
| 11.330 | 9220 | 1134 | 0.055 |
| 11.683 | 27987 | 1788 | 0.167 |
| 11.897 | 25373 | 2023 | 0.151 |
| 12.733 | 44185 | 5677 | 0.263 |
| 13.155 | 16628690 | 1037985 | 99.001 |
| 13.600 | 50018 | 5052 | 0.298 |
| 21.041 | 11063 | 1302 | 0.066 |
| | | | 100.000 |

Click Core 4

Tetra MAP #1 Click

MULTI-ANTIGENIC PEPTIDE MIMICS OF GONOCOCCAL LIPO-OLIGOSACCHARIDE (LOS) EPITOPES

CROSS-REFERENCE TO RELATED APPLICATIONS

This application is a national stage filing under 35 U.S.C. § 371 of international PCT application PCT/US2020/052057, filed Sep. 22, 2020, which claims priority under 35 U.S.C. § 119(e) to U.S. provisional patent application, U.S. Ser. No. 62/903,963, filed Sep. 23, 2019, the entire contents of each of which are incorporated herein by reference.

STATEMENT REGARDING FEDERALLY SPONSORED RESEARCH OR DEVELOPMENT

This invention was made with government support under AI114710 awarded by the National Institutes of Health. The government has certain rights in the invention.

BACKGROUND

The sexually transmitted disease, gonorrhea, is a commonly reported communicable disease and poses a worldwide risk. Gonorrhea is caused by the bacterium *Neisseria gonorrhoeae* (*N. gonorrhoeae*) which is a gram-negative diplococcus. Although *N. gonorrhoeae* primarily infects mucous membranes, it is capable of invading tissues and evading host defenses. *N. gonorrhoeae* is the causative agent of a spectrum of sequelae. These sequelae range from asymptomatic mucosal infections to significant disease syndromes in both sexes, for example, disseminated gonococcal infection (DGI) in men and women, as well as salpingitis or pelvic inflammatory disease (PID) in women. Other sequelae include, recurrent infection, chronic pelvic pain, dyspareunia, pelvic adhesions and other lasting inflammatory effects.

*N. gonorrhoeae* has multiple virulence factors. The surface components of this pathogen play an important role in attaching to and invading host cells, while providing potential targets for the host immune response. Gonococcal infections elicit local and systemic humoral and cellular immune responses to several components which are exhibited as surface exposed antigens of the bacterium, particularly pili, porin (Por) or protein I (PI), opacity associated proteins (Opas) or protein IIs, Rmp or protein III, and lipooligosaccharides (LOS). Pili, Opa, Por, and LOS are all implicated in attachment to and invasion of the host and all display considerable variation on their surface exposed regions.

In both symptomatic and asymptomatic patients, gonococcal infections have been shown to stimulate increased levels of anti-gonococcal serum immunoglobulins. The peripheral humoral response is predominately IgG (mostly subclass IgG3), with lesser amounts of IgM and IgA. Quantitatively, the antibody response is primarily directed against the pili, Opa proteins, and LOS. Local antibodies are present in genital secretions, but in reduced amounts, and may be directed against different antigenic targets than those in serum. The predominant class of antibodies present in secretions is also IgG (mostly IgG3) and not secretory IgA (sigA). Antibodies against LOS are present as well, but in lesser amounts than those against pili, Por, and Opa. Although patients infected with *N. gonorrhoeae* may show an antibody response to many gonococcal antigens, *N. gonorrhoeae* isolated from patients with disseminated infection (DGI) are resistant to the bactericidal action of normal human serum (NHS) and of most convalescent sera. This serum-resistant phenotype, termed stable serum resistance (SR), may enable the organism to evade local defenses, penetrate mucosal barriers and disseminate via the bloodstream.

Attempts to use individual surface components of the pathogen as targets for conventional vaccines have been unsuccessful because of their antigenic variability. Pilus vaccines have been protective only against infection with the homologous strain (used to make the pilus vaccine) and Por vaccination has been unsuccessful even in human experimental challenge. In addition, *N. gonorrhoeae* express marked phenotypic heterogeneity, typically shifting from one antigenic form to another at a frequency of >1 in $10^3$ organisms making the surface of this organism a moving target for most vaccine strategies. Although the vaccine candidates have provoked antibody responses, the antibodies and immune responses produced have not been broadly protective.

SUMMARY

*Neisseria gonorrhoeae* (*N. gonorrhoeae*), the causative agent of the sexually transmitted disease gonorrhea, has become resistant to almost every antibiotic in clinical use. Currently, the combination of the antibiotics ceftriaxone and azithromycin is the first-line of treatment for gonorrhea recommended by the Centers for Disease Control and Prevention (CDC). However, resistance to each of these antibiotics has been reported in several countries, which further limits treatment options. In addition, the number of cases of gonorrhea is increasing rapidly. In 2017, 555,608 cases of gonorrhea were reported to the CDC, a 67% increase in the number of cases in five years (www.cdc.gov/std/stats17/Gonorrhea.htm). Therefore, there is an urgent need for safe and effective vaccines against gonorrhea to prevent the global spread of multidrug-resistant organisms.

In some aspects, the disclosure relates to compound (e.g., peptide mimic) comprising Formula (I)

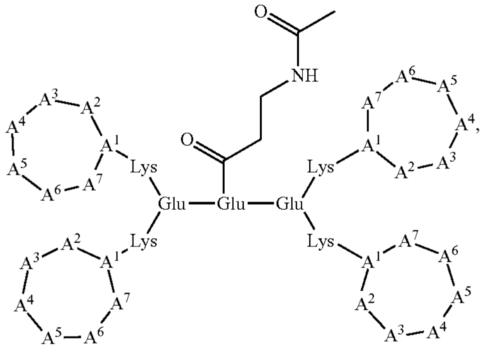

or a salt or polymorph thereof, wherein: A1, A2, A3, A5, A6, and A7 are each independently a bond, an amino acid residue, substituted or unsubstituted acyl, substituted or unsubstituted alkylene, substituted or unsubstituted alkenylene, substituted or unsubstituted heteroalkylene, substituted or unsubstituted heterocyclylene, or substituted or unsubstituted heteroarylene, or a combination thereof; and A4 is a peptidyl sequence.

In some embodiments, A1, A2, A3, A5, A6, and A7 are each independently an amino acid residue, substituted or unsubstituted acyl, or substituted or unsubstituted alkylene, or a combination thereof. In some embodiments, A1, A2, A3, A5, and A6 are each independently an amino acid residue. In some embodiments, A1, A2, A3, A5, and A6 are each independently glycine, proline, or cysteine. In some embodiments, A1 is cysteine, and A2, A3, A5, and A6 are each independently glycine or proline. In some embodiments, A7 is an amino acid residue, substituted or unsubstituted acyl, or substituted or unsubstituted alkylene, or a combination thereof. In some embodiments, A7 is cysteine, substituted or unsubstituted acyl, or substituted or unsubstituted alkylene, or a combination thereof.

In some embodiments, A7 is $-(C{=}X)-CR_2-$; wherein X is oxygen (O) or sulfur (S), and each R is independently hydrogen (H), substituted or unsubstituted alkyl, or halogen. In some embodiments, A7 is $*-(C{=}O)-CH_2-$; wherein * indicates attachment to A6.

In some embodiments, A4 is an antigenic peptidyl sequence. In some embodiments, A4 is a 12-mer antigenic peptidyl sequence. In some embodiments, A4 is a 12-mer antigenic peptidyl sequence, wherein each amino acid residue is independently isoleucine, proline, valine, leucine, aspartic acid, glutamic acid, asparagine, glycine, phenylalanine, or alanine.

In some embodiments, A4 is *-Ile-Pro-Val-Leu-Asp-Glu-Asn-Gly-Leu-Phe-Ala-Pro-(SEQ ID NO: 2); wherein * indicates attachment to A5.

In some embodiments, the compound (e.g., peptide mimic) of Formula (I) comprises Formula (I-a)

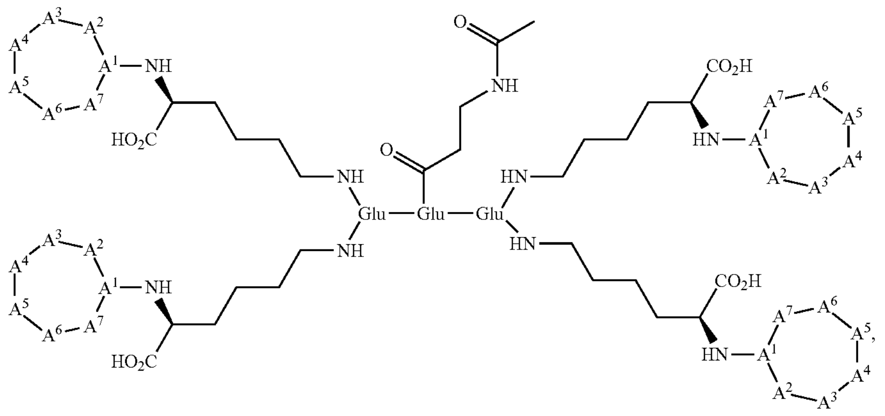

or a salt or polymorph thereof.

In some embodiments, the compound (e.g., peptide mimic) of Formula (I) comprises Formula (I-b)
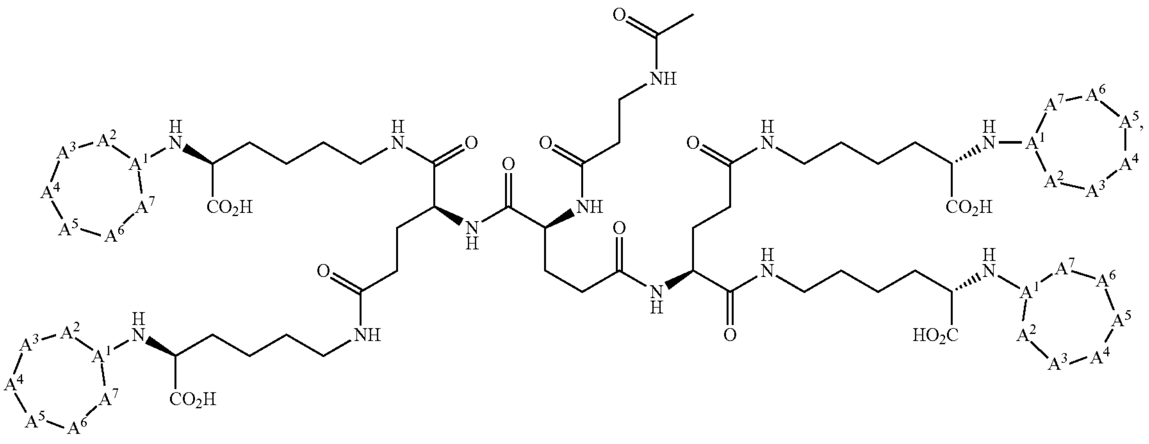
or a salt or polymorph thereof.
In some embodiments, the compound (e.g., peptide mimic) of Formula (I) comprises Formula (I-c)
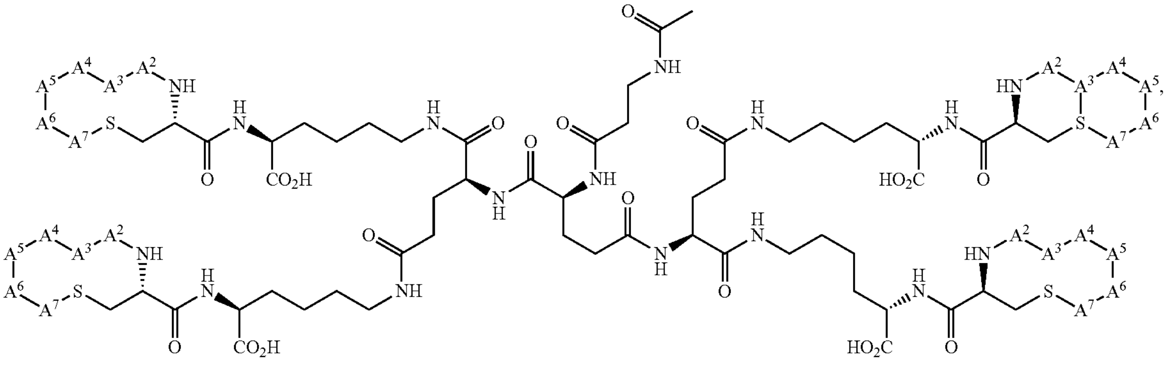
or a salt or polymorph thereof.
In some embodiments, the compound (e.g., peptide mimic) of Formula (I) comprises Formula (I-d)
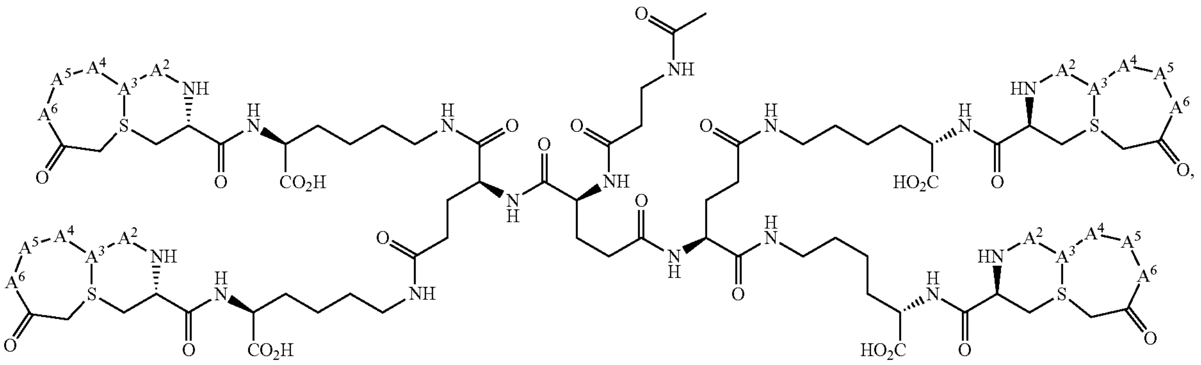
or a salt or polymorph thereof.

In some embodiments, the compound (e.g., peptide mimic) of Formula (I) comprises Formula (I-e)

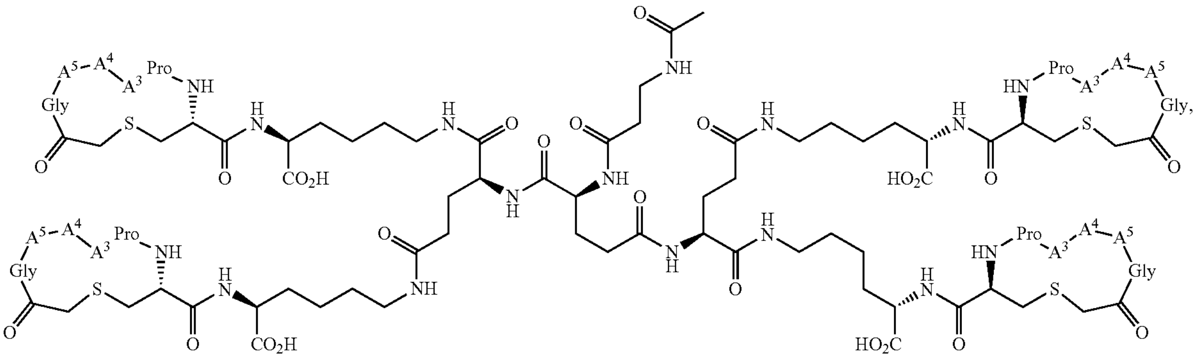

or a salt or polymorph thereof.

In some embodiments, the compound (e.g., peptide mimic) of Formula (I) comprises Formula (I-f)

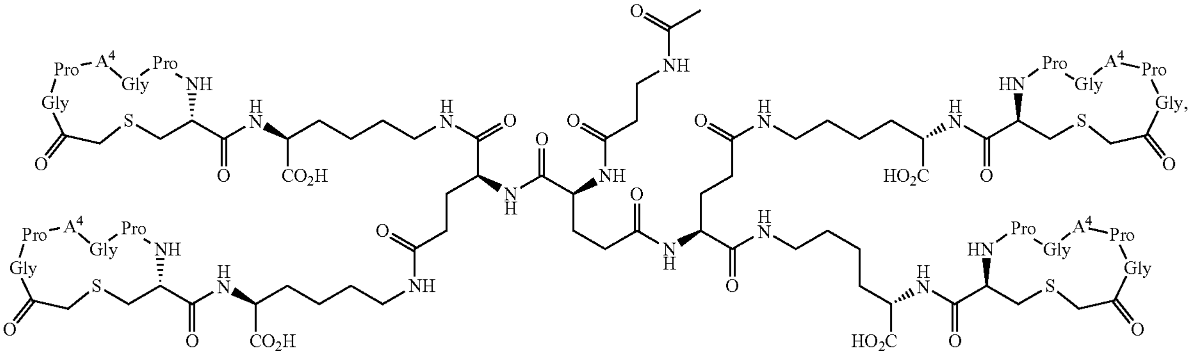

or a salt or polymorph thereof.

In some embodiments, the compound (e.g., peptide mimic) of Formula(I-f), or a salt or polymorph thereof, wherein A4 is *-Ile-Pro-Val-Leu-Asp-Glu-Asn-Gly-Leu-Phe-Ala-Pro-(SEQ ID NO: 2), wherein * indicates attachment to Pro.

In some aspects, the disclosure relates to a compound (e.g., peptide mimic) of the Formula (II), or a salt or polymorph thereof, wherein, A2, A3, A5, and A6 are each independently an amino acid residue; A4 is an antigenic peptidyl sequence; $R^1$ is hydrogen, a solid support resin, or a protecting group; and $R^2$ is hydrogen or a protecting group.

In some aspects, the disclosure relates to a compound (e.g., peptide mimic) of Formula (III), or a salt or polymorph thereof, wherein, X is a leaving group; A2, A3, A5, and A6 are each independently an amino acid residue; A4 is an antigenic peptidyl sequence; $R^1$ is hydrogen, a solid support resin, or a protecting group; and $R^2$ is hydrogen or a protecting group.

In some aspects, the disclosure relates to a peptide mimic of a conserved gonococcal lipo-oligosaccharide (LOS) epitope not found on human blood group antigens, wherein the peptide mimic is capable of inducing in a subject an immune response against the conserved gonococcal LOS epitope. In some embodiments, the peptide mimic comprises the amino acid sequence of the MAP Core Peptide 2 as shown in FIG. 1A (SEQ ID NO: 1). In some embodiments, the immune response is T-cell dependent.

In some embodiments, the peptide mimic is coupled to a second agent. In some embodiments, the second agent is an adjuvant. In some embodiments, the second agent is a second protein.

In some embodiments, the peptide mimic competes with gonococcal lipooligosaccharide (LOS) for binding to monoclonal antibody 2C7 produced by a hybridoma cell line having the ATCC accession number HB-11859.

In some embodiments, the peptide mimic immuno-specifically binds to monoclonal antibody 2C7 produced by a hybridoma cell line having the ATCC accession number HB-11859.

In some embodiments, the peptide mimic immuno-specifically binds to a monoclonal antibody produced by immunizing a subject with an anti idiotypic monoclonal antibody, or fragment thereof, wherein the anti-idiotypic monoclonal antibody is produced by a hybridoma cell line having the ATCC accession number HB-11311.

In some embodiments, the disclosure relates to compositions containing any of the peptide mimics disclosed herein in an effective amount and a pharmaceutically acceptable excipient or carrier.

In some aspects, the disclosure relates to a method of immunizing a subject against *N. gonorrhoeae* infection comprising administering to a subject an effective amount of the peptide mimics disclosed herein and a pharmaceutically acceptable carrier. In some embodiments, the peptide mimic of further comprises a complement protein. In some embodiments, the complement protein is C3d.

In some aspects, the disclosure relates to a method of immunizing a subject against *N. gonorrhoeae* infection comprising administering to the subject an effective amount of the peptide mimic and a pharmaceutically acceptable carrier. In some embodiments, the method for immunizing against *N. gonorrhoeae* infection comprising an effective amount of composition comprising the peptide mimic is used. In some embodiments, the composition comprises a peptide mimic coupled to a complement protein to increase the antigenicity thereof. In some embodiments, the complement protein is C3d.

BRIEF DESCRIPTION OF DRAWINGS

FIG. 1A: shows the chemical structure of TMCP2, the 2C7 mimitope peptide configured as a tetrameric multiantigenic peptide (peptide mimic) (MAP). The 2C7 mimitope is indicated in shown as the sequence "$H_2C$-CO-GPIPVLDENGLFAPGPC" (SEQ ID NO: 1) Cyclization is maintained through a thioether bond. The reverse peptide mimic core is represented the schematic of the peptide mimic as "Ac-β-Ala-Glu[Glu-OH]$_2$." The reverse peptide mimic core links to each cyclic peptide through a lysine (K) residue. FIG. 1B: shows inhibition of mAb 2C7 binding to solid phase-affixed (coated) gonococcal LOS by: monomeric cyclic peptide (peptide mimic Core Peptide 2, abbreviated 'CP2'); TMCP2 and nominal LOS (control). mAb 2C7 (0.04 μg/ml) was added to microtiter wells coated with LOS purified from gonococcal strain 15253 in the presence of increasing concentrations of CP2, TMCP2 or LOS (positive control for 100% inhibition). The Y-axis shows the % inhibition of mAb 2C7 binding (residual binding) to immobilized LOS in the presence of the peptide (TMCP2 or CP2) or soluble LOS relative to binding of mAb 2C7 alone to immobilized LOS.

FIG. 2A: shows antibody levels against LOS purified from *N. gonorrhoeae* strain 15253 (elaborates the 2C7 epitope optimally). Anti-LOS IgG levels against 15253 LOS were measured in sera obtained 2 weeks after each dose. None of the sera showed detectable IgG Ab binding to 15253 ΔlgtG LOS. GLA-SE alone (adjuvant control) showed no detectable anti-gonococcal LOS IgG. FIG. 2B: shows bactericidal activity of immune sera against *N. gonorrhoeae* FA1090. Post-dose 3 sera (IgM depleted) were tested for their ability to kill *N. gonorrhoeae* FA1090 using human complement (16.7% (v/v)) as the complement source. The concentration of heat-inactivated mouse antiserum in the reaction mixtures are shown on the X-axis. All IgM-depleted anti-sera from mice immunized with GLA-SE alone did not show any bactericidal activity (>100% survival; data not shown).

FIG. 3A: Efficacy of TMCP2/GLA-SE against FA1090. FIG. 3B: Efficacy of TMCP2/GLA-SE against MS11. The left panels of FIGS. 3A-3B (Kaplan Meier analysis) show time to clearance of infection. Groups were compared using the Mantel-Cox log-rank test. Significance was set at 0.008 (Bonferroni's correction for 4 groups). The center panels of FIGS. 3A-3B show log 10 CFU versus time. The right panels of FIGS. 3A-3B show bacterial burdens consolidated over time (Area Under the Curve [log 10 CFU]analysis). The four groups were compared using the non-parametric Kruskal-Wallis equality of populations rank test. The $\chi 2$ with ties (three degrees of freedom) was 14.36 (P=0.0025) for FA1090 (FIG. 3A) and 13.69 (P=0.0034) for MS11 (FIG. 3B). Pairwise comparisons across groups (indicated with the graphs) was made with the Two-sample Wilcoxon rank-sum (Mann-Whitney) test.

FIG. 4A: shows anti-LOS antibody levels in immune sera. Sera obtained 2 weeks after each dose were assayed for antibody levels against *N. gonorrhoeae* 15253 LOS. None of the anti-sera from mice immunized with GLA-SE alone (adjuvant control) showed measurable anti-gonococcal LOS IgG levels. FIG. 4B: shows bactericidal activity of immune sera. Post-dose 3 sera (IgM depleted) used at concentrations of 10% (1/10 dilution), 12.5% (1/8 dilution) or 16.7% (1/6 dilution) (concentrations indicated on the X-axis) were tested for their ability to kill *N. gonorrhoeae* FA1090 using human complement (16.7% (v/v)) as the complement source. Y-axis, % bacterial survival at 30 min relative to 0 min. None of the IgM-depleted anti-sera from adjuvant control mice (given GLA-SE alone) showed any bactericidal activity (>100% survival; data not shown). FIG. 4C: shows bactericidal activity against strain MS11 of immune sera from mice immunized with three doses of 50 μg, each given 3 weeks apart. Bactericidal assays were performed as described in B, except that immune sera were tested at (lower) concentrations: 1.3, 3.3 and 6.7% with 6.7% human complement (IgG/IgM depleted NHS (Pel-Freez)) added as a source of complement. None of the IgM-depleted antisera from adjuvant control mice (given GLA-SE alone) showed any bactericidal activity (>100% survival; Table 5 and Table 6 show the numerical data).

FIG. 5A: shows three panels. The left panel shows time to clearance of infection (Kaplan Meier analysis; groups were compared using the Mantel-Cox log-rank test). The middle panel shows log 10 CFU versus time. The right panel shows bacterial burdens consolidated over time (Area Under the Curve [log 10 CFU] analysis). Pairwise comparisons between groups was made with the Two-sample Wilcoxon rank-sum (Mann-Whitney) test. FIG. 5B: shows anti-LOS antibody levels in immune sera. Sera obtained 2 weeks after the third vaccine dose was assayed for antibody levels against *N. gonorrhoeae* 15253 LOS. None of the anti-sera from mice immunized with GLA-SE alone (adjuvant control) showed measurable anti-gonococcal LOS IgG levels. FIG. 5C: shows bactericidal activity of immune sera. Sera obtained 2 weeks after the 3rd vaccine dose (IgM depleted) used at concentrations of 10% (1/10 dilution), 12.5% (1/8 dilution) or 16.7% (1/6 dilution) (concentrations indicated on the X-axis) were tested for their ability to kill *N. gonorrhoeae* FA1090 using human complement (16.7% (v/v)) as the complement source. Y-axis, % bacterial survival at 30 min relative to 0 min. None of the IgM-depleted anti-sera from adjuvant control mice (given GLA-SE alone) showed any bactericidal activity (>100% survival; data not shown).

FIG. 12A: shows immunogenicity of TMCP2 with different adjuvants. BALB/c mice (n=5/group) were immunized IM with 5, 25, or 50 μg of TMCP2 plus the adjuvants indicated above each graph at 0, 3, and 6 weeks. Pre-immune sera (wk 0) and sera collected 2 weeks after each dose (wk 2, 5, and 8) were assayed for IgG against Ng 15253 LOS by ELISA. Data using the 50 μg dose, which elicited the highest responses, are shown. FIG. 12B: shows serum bactericidal activity antisera elicited by TMCP2 immunization with different adjuvants. Week 8 (post-dose 3) antisera from all 5 mice in each group were pooled and tested in serum bactericidal assays at anti-serum dilutions of either 1:3 or 1:6, with normal human serum (NHS) as the complement source. Because intact antisera (IgM replete) in all groups, including the adjuvant control groups, supported bactericidal activity (>95% killing in every instance, the data shown are following IgM depletion).

FIG. 13A: IgM binding LOS. FIG. 13B: IgG binding to LOS. X-axes, reciprocal serum dilution; Y-axes, antibody (IgM or IgG) binding (OD405 nm). Note the different Y-axes scales in the upper and lower panels.

FIG. 20A shows the (6-Azido-hexynoyl)$_4$-Lys$_2$-Lys-β-Ala-OH structure of Click Core 4. FIG. 20B shows the structure of Click Core 4 product with Cyclic peptide #1.

DETAILED DESCRIPTION OF CERTAIN EMBODIMENTS

Definitions

Figure 1A:
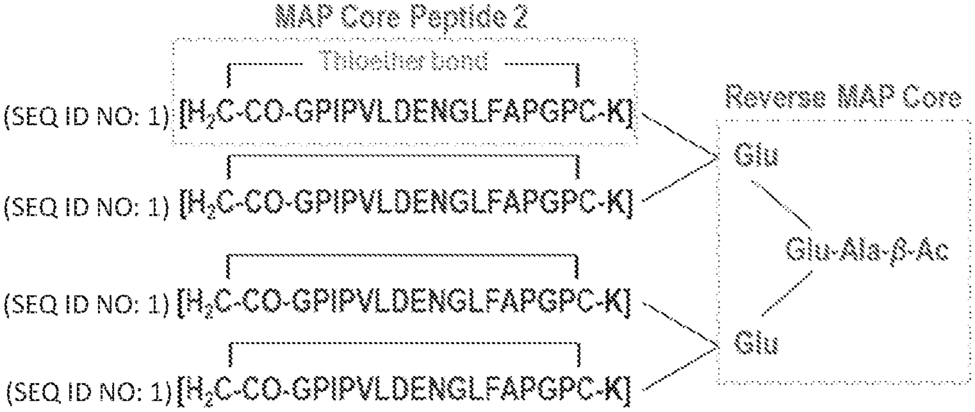
FIGS. 1A-1B show the structure and characterization of one of the peptide mimics described herein (also referred to as TMCP2).

The term "acyl," as may be used herein, refers to a group having the general formula —C(═O)$R^{X1}$, —C(═O)O$R^{X1}$, —C(═O)—O—C(═O)$R^{X1}$, —C(═O)S$R^{X1}$, —C(═O)N($R^{X1}$)$_2$, —C(═S)$R^{X1}$, —C(═S)N($R^{X1}$)$_2$, and —C(═S)S($R^{X1}$), —C(═N$R^{X1}$)$R^{X1}$, —C(═N$R^{X1}$)O$R^{X1}$, —C(═N$R^{X1}$)S$R^{X1}$, and —C(═N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6 membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)).

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-12}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-8}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-6}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("$C_1$ alkenyl"). The one or more carbon-carbon double bonds can be internal (such as in 2-butenyl) or terminal (such as in 1-butenyl). Examples of $C_{1-4}$ alkenyl groups include methylidenyl ($C_1$), ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{1-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_5$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{1-20}$ alkenyl. In certain embodiments, the alkenyl group is a substituted $C_{1-20}$ alkenyl. In an alkenyl group, a C═C double bond for which the stereochemistry is not specified (e.g., —CH═$CHCH_3$ or

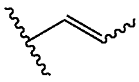
)

may be in the (E)- or (Z)-configuration.

As used herein, an "antibody" is an intact immunoglobulin comprising two each of immunoglobulin light and heavy chains. Accordingly, antibodies include intact immunoglobulins of types IgA, IgG, IgE, IgD, IgM (as well as subtypes thereof), wherein the light chains of the immunoglobulin may be of types kappa or lambda.

The terms "binding affinity" and "KA," as may be used interchangeably herein, refer to the apparent association a molecule to its ligand. Binding affinities are well known in the art and generally the KA is known to be the reciprocal of the dissociation constant (KD). The compositions and agents (e.g., peptide mimics) described herein may have a binding affinity (KA) of at least $10^5$, $10^6$, $10^7$, $10^8$, $10^9$, $10^{10}$ M, or higher. An increased binding affinity corresponds to a decreased KD. Higher affinity binding of an antibody to a first target relative to a second target can be indicated by a higher KA (or a smaller numerical value KD) for binding the first target than the KA (or numerical value KD) for binding the second target. In such cases, the antibody has specificity for the first target relative to the second target. Differences in binding affinity (e.g., for specificity or other comparisons) can be greater than 1, for example at least 1.1; 1.5; 2; 3; 4; 5; 10; 15; 20; 37.5; 50; 70; 80; 91; 100; 500; 1,000; 10,000, 100,000 fold, or more.

The term "effective amount," as used herein, refers to an amount of a biologically active agent that is sufficient to elicit a desired biological response. For example, in some embodiments, an effective amount of a peptide mimic may refer to the amount of the peptide mimic that is sufficient to treat a disorder (e.g., *N. gonorrhoeae*). In some embodiments, an effective amount of a peptide mimic provided herein, may refer to the amount of the peptide mimic that is sufficient to induce a therapeutic effect. As will be appreciated by the skilled artisan, the effective amount of an agent (e.g., peptide mimic), may vary depending on various factors as, for example, on the subject to be treated (e.g., age, gender, severity of infection) or on the concentration and route of administration of the agent being used.

The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$alkyl"). In certain embodiments, a heteroalkyl group refers to a saturated group having from 1 to 12 carbon atoms and 1 or more heteroatoms within the parent chain ("hetero$C_{1-20}$alkyl"). In some embodiments, a heteroalkyl group is a saturated group having 1 to 11 carbon atoms and 1 or more heteroatoms within the parent chain ("hetero$C_{1-11}$ alkyl"). In some embodiments, a heteroalkyl group is a saturated group having 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and lor 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-12}$ alkyl. In certain embodiments, the heteroalkyl group is a substituted hetero$C_{1-12}$ alkyl.

The term "heteroaryl" refers to a radical of a 5-14 membered monocyclic or polycyclic (e.g., bicyclic, tricyclic) 4n+2 aromatic ring system (e.g., having 6, 10, or 14 7t electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3-to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetra¬hydro¬benzo¬ithienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetra¬hydro¬pyrano[3,4-b]pyrrolyl, 5,6-dihydro-4H-furo[3,2-b]pyrrolyl, 6,7-dihydro-5H-furo¬[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo¬[2,3-b]pyridinyl, 4,5,6,7-tetra¬hydro¬furo[3,2-c]pyridinyl, 4,5,6,7-tetrahydro¬thieno[3,2-b]pyridinyl, 1,2,3,4-tetrahydro-1,6-naphthyridinyl, and the like.

The term "linker," as used herein, refers to a chemical moiety linking two molecules or moieties (e.g., components of a peptide mimic as disclosed herein). Typically, the linker is positioned between, or flanked by, two groups, molecules, or other moieties and connected to each one via a covalent bond, thus connecting the two, however a linker may connect to ends of a molecule (e.g., nucleic acid, peptidyl sequence, peptide). In some embodiments, the linker comprises an amino acid or a plurality of amino acids (e.g., a peptide or protein). In some embodiments, the linker comprises a nucleotide (e.g., DNA or RNA) or a plurality of nucleotides (e.g., a nucleic acid). In some embodiments, the linker is an organic molecule, functional group, group, polymer, or other chemical moiety. In some embodiments, the linker is a cleavable linker, e.g., the linker comprises a bond that can be cleaved upon exposure to, for example, UV light or a hydrolytic enzyme, such as a protease or esterase. In some embodiments, the linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids). In other embodiments, the linker is a chemical bond (e.g., a covalent bond, amide bond, disulfide bond, ester bond, carbon-carbon bond, carbon heteroatom bond).

As used herein, "monoclonal antibodies" are monospecific antibodies produced initially by a single clone of antibody forming cells.

As used herein a "peptide mimic" refers to a peptide which presents in a similar manner and which has a profile similar to that of an epitope, of which it is a mimic. By presenting and having a profile similar to that of an epitope, a peptide mimic may elicit an immunological response in a similar fashion as the epitope of which it mimics.

A "leaving group" (LG) is an art-understood term referring to an atomic or molecular fragment that departs with a pair of electrons in heterolytic bond cleavage, wherein the molecular fragment is an anion or neutral molecule. As used herein, a leaving group can be an atom or a group capable of being displaced by a nucleophile. See e.g., Smith, March Advanced Organic Chemistry 6th ed. (501-502). Exemplary leaving groups include, but are not limited to, halo (e.g., fluoro, chloro, bromo, iodo) and activated substituted hydroxyl groups (e.g., $—OC(=O)SR^{aa}$, $—OC(=O)R^{aa}$, $—OCO_2R^{aa}$, $—OC(=O)N(R^{bb})_2$, $—OC(=NR^{bb})R^{aa}$, $—OC(=NR^{bb})OR^{aa}$, $—OC(=NR^{bb})N(R^{bb})_2$, $—OS(=O)R^{aa}$, $—OSO_2R^{aa}$, $—OP(R^{cc})_2$, $—OP(R^{cc})_3$, $—OP(=O)_2R^{aa}$, $—OP(=O)(R^{aa})_2$, $—OP(=O)(OR^{cc})_2$-$OP(=O)_2N(R^{bb})_2$, and $—OP(=O)(NR^{bb})_2$, wherein $R^{aa}$, $R^{bb}$, and $R^{cc}$ are as defined herein). Additional examples of suitable leaving groups include, but are not limited to, halogen alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some embodiments, the leaving group is a sulfonic acid ester, such as toluenesulfonate (tosylate, —OTs), methanesulfonate (mesylate, —OMs), p-bromobenzenesulfonyloxy (brosylate, —OBs), $—OS(=O)_2(CF_2)_3CF_3$ (nonaflate, —ONf), or trifluoromethanesulfonate (triflate, —OTf). In some embodiments, the leaving group is a brosylate, such as p-bromobenzenesulfonyloxy. In some embodiments, the leaving group is a nosylate, such as 2-nitrobenzenesulfonyloxy. In some embodiments, the leaving group is a sulfonate-containing group. In some embodiments, the leaving group is a tosylate group. In some embodiments, the leaving group is a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties..

In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not limited in any manner by the exemplary substituents described herein.

Exemplary carbon atom substituents include halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(═O)$R^{aa}$, —$CO_2H$, —CHO, —$C(OR^{cc})_2$, —$CO_2R^{aa}$, —OC(═O)$R^{aa}$, —$OCO_2R^{bb}$, —C(═O)$N(R^{bb})_2$, —OC(═O)$N(R^{bb})_2$, —$NR^{bb}$C(═O)$R^{aa}$, —$NR^{bb}CO_2R^{aa}$, —$NR^{bb}$C(═O)$N(R^{bb})_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)$N(R^{bb})_2$, —OC(═$NR^{bb}$)$N(R^{bb})_2$, —$NR^{bb}$C(═$NR^{bb}$)$N(R^{bb})_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —$Si(R^{aa})_3$, —$OSi(R^{aa})_3$ —C(═S)$N(R^{bb})_2$, —C(═O)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$(R^{aa})_2$, —P(═O)$(OR^{cc})_2$, —OP(═O)$(R^{aa})_2$, —OP(═O)$(OR^{bb})_2$, —P(═O)$(N(R^{bb})_2)_2$, —OP(═O)$(N(R^{bb})_2)_2$, —$NR^{bb}$P(═O)$(R^{aa})_2$, —$NR^{bb}$P(═O)$(OR^{cc})_2$, —$NR^{bb}$P(═O)$(N(R^{bb})_2)_2$, —$P(R^{cc})_2$, —$P(OR^{cc})_2$, —$P(R^{cc})_3^+X^-$, —$P(OR^{cc})_3$*$X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_2$, —$B(R^{aa})_2$, —$B(OR^{cc})_2$, —$BR^{aa}(OR^{cc})$, $C_{1-20}$ alkyl, $C_{1-20}$ perhaloalkyl, $C_{1-20}$ alkenyl, $C_{1-20}$ alkynyl, hetero$C_{1-20}$alkyl, hetero$C_{1-20}$alkenyl, hetero$C_{1-20}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group ═O, ═S, ═$NN(R^{bb})_2$, ═$NNR^{bb}$C(═O)$R^{aa}$, ═$NNR^{bb}$C(═O)$OR^{aa}$, ═$NNR^{bb}$S(═O)$_2R^{aa}$, ═$NR^{bb}$, or ═$NOR^{cc}$;

wherein:

each instance of $R^{aa}$ is, independently, selected from $C_{1-20}$ alkyl, $C_{1-20}$ perhaloalkyl, $C_{1-20}$ alkenyl, $C_{1-20}$ alkynyl, hetero$C_{1-20}$alkyl, hetero$C_{1-20}$alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(R^{aa})_2$, —P(═O)$(OR^{cc})_2$, —P(═O)$(N(R^{cc})_2)_2$, $C_{1-20}$ alkyl, $C_{1-20}$ perhaloalkyl, $C_{1-20}$ alkenyl, $C_{1-20}$ alkynyl, hetero$C_{1-20}$alkyl, hetero$C_{1-20}$alkenyl, hetero$C_{1-20}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-20}$ alkyl, $C_{1-20}$ perhaloalkyl, $C_{1-20}$ alkenyl, $C_{1-20}$ alkynyl, hetero$C_{1-20}$alkyl, hetero$C_{1-20}$alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3^+X^-$, —$N(OR^{ee})R^{ff}$, —SH, —$SR^{ee}$, $SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}$C(═$NR^{ff}$)$N(R^{ff})_2$, —$NR^{ff}SO_2R^{ee}$, —$SO_2N(R^{ff})_2$, —$SO_2R^{ff}$, —$SO_2OR^{ee}$, —$OSO_2R^{ee}$ —S(═O)$R^{ee}$, —Si(Re)$_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$, —OP(═O)$(R^{ee})_2$, —OP(═O)$(OR^{ee})_2$, $C_{1-10}$ alkyl, $C_{1-10}$ perhaloalkyl, $C_{1-10}$ alkenyl, $C_{1-10}$ alkynyl, hetero$C_{1-10}$alkyl, hetero$C_{1-10}$alkenyl, hetero$C_{1-10}$alkynyl, $C_{3-10}$ carbocyclyl, 3-10 membered heterocyclyl, $C_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents are joined to form ═O or ═S; wherein $X^-$ is a counterion;

each instance of $R^{ee}$ is, independently, selected from $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, 3-10 membered heterocyclyl, $C_{6-10}$ aryl, and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)\ {}^+X^-$, —$NH_3{}^+X^-$, —$N(OC_{1-6}$ alkyl$)(C_{1-6}$ alkyl), —$N(OH)(C_{1-6}$ alkyl), —NH(OH), —SH, —$SC_{1-6}$ alkyl, —$SS(C_{1-6}$ alkyl), —$C(=O)(C_{1-6}$ alkyl), —$CO_2H$, —$CO_2(C_{1-6}$ alkyl), —$OC(=O)(C_{1-6}$ alkyl), —$OCO_2(C_{1-6}$ alkyl), —$C(=O)NH_2$, —$C(=O)N(C_{1-6}$ alkyl$)_2$, —$OC(=O)NH(C_{1-6}$ alkyl), —$NHC(=O)(C_{1-6}$ alkyl), —$N(C_{1-6}$ alkyl$)C(=O)(C_{1-6}$ alkyl), —$NHCO_2(C_{1-6}$ alkyl), —$NHC(=O)N(C_{1-6}$ alkyl$)_2$, —$NHC(=O)NH(C_{1-6}$ alkyl), —$NHC(=O)NH_2$, —$C(=NH)O(C_{1-6}$ alkyl), —$OC(=NH)(C_{1-6}$ alkyl), —$OC(=NH)OC_{1-6}$ alkyl, —$C(=NH)N(C_{1-6}$ alkyl$)_2$, —$C(=NH)NH(C_{1-6}$ alkyl), —$C(=NH)NH_2$, —$OC(=NH)N(C_{1-6}$ alkyl$)_2$, —$OC(NH)NH(C_{1-6}$ alkyl), —$OC(NH)NH_2$, —$NHC(NH)N(C_{1-6}$ alkyl$)_2$, —$NHC(=NH)NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$ —$C(=S)N(C_{1-6}$ alkyl$)_2$, $C(=S)NH(C_{1-6}$ alkyl), $C(=S)NH_2$, —$C(=O)S(C_{1-6}$ alkyl), —$C(=S)SC_{1-6}$ alkyl, —$SC(=S)SC_{1-6}$ alkyl, —$P(=O)(OC_{1-6}$ alkyl$)_2$, —$P(=O)(C_{1-6}$ alkyl$)_2$, —$OP(=O)(C_{1-6}$ alkyl$)_2$, —$OP(=O)(OC_{1-6}$ alkyl$)_2$, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, or 5-10 membered heteroaryl; or two geminal $R^{gg}$ substituents can be joined to form =O or =S; and each $X^-$ is a counterion.

The terms "protein," "peptide," "peptidyl sequence," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide (e.g., peptide mimic) may be naturally occurring, recombinant, or synthetic, or any combination thereof. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, Molecular Cloning: A Laboratory Manual (4th ed., Cold Spring Harbor Laboratory Press, Cold Spring Harbor, N.Y. (2012)), the entire contents of which are incorporated herein by reference.

The terms "percent identity," "sequence identity," "% identity," "% sequence identity," and % identical," as they may be interchangeably used herein, refer to a quantitative measurement of the similarity between two sequences (e.g., nucleic acid or amino acid). The percent identity of genomic DNA sequence, intron and exon sequence, and amino acid sequence between humans and other species varies by species type, with chimpanzee having the highest percent identity with humans of all species in each category.

Calculation of the percent identity of two nucleic acid sequences, for example, can be performed by aligning the two sequences for optimal comparison purposes (e.g., gaps can be introduced in one or both of a first and second nucleic acid sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences.

The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTA Atschul, S. F. et al., J. Molec. Biol., 215, 403 (1990)).

When a percent identity is stated, or a range thereof (e.g., at least, more than, etc.), unless otherwise specified, the endpoints shall be inclusive and the range (e.g., at least 70% identity) shall include all ranges within the cited range (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (e.g., 0.1%), hundredths of a percent (e.g., 0.01%), etc.).

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions. In some embodiments, the compositions and agents described herein (e.g., peptide mimics) are polymorphs.

As used herein, the term "salt" refers to any and all salts. The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the peptide mimics of the disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "subject," as used herein, refers to an individual organism, for example, an individual mammal. As used herein, a "mammal," may be any animal constituting the class Mammalia (e.g., a human, mouse, rat, cat, dog, sheep, rabbit, horse, cow, goat, pig, guinea pig, hamster, chicken, turkey, or a non-human primate (e.g., Marmoset, Macaque)). In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence. In some embodiments, any of the methods described herein may be used to treat a subject.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

Certain Embodiments

LOS is an important virulence determinant of *N. gonorrhoeae*. Considerable evidence supports the role of LOS as a major target of bactericidal antibody directed to the surface of *N. gonorrhoeae*. Antibodies to LOS have several important functions: bactericidal activity; complement activation through the classical or alternative complement pathways; and opsonic activity. Additionally, LOS has been shown to be the most effective gonococcal antigen to induce a functional antibody response to homologous and heterologous gonococci.

The monoclonal antibody (mAb) 2C7, detects a LOS derived oligosaccharide (OS) epitope that appears to be widely conserved and expressed amongst clinical isolates of gonococci. Typically, saccharides are T-cell independent antigens. When administered alone as immunogens, they generally elicit only a primary antibody response. In addition, oligosaccharides are small (<10 saccharide units), and would likely require additional biochemical derivatization to render them immunogenic. The use of such oligosaccharides as vaccine candidates, therefore, is limited in several respects.

The instant disclosure generally solves the problems referred to above by providing peptide mimics of widely conserved oligosaccharide epitopes of *N. gonorrhoeae* which are not present in human blood group antigens. Such peptide mimics elicit bactericidal antibody responses against a conserved oligosaccharide epitope of *N. gonorrhoeae* to significantly reduce the duration and burden of gonococcal cervico-vaginal colonization and methods of use. Such peptide mimics can be used as described herein as well as according to methods described in the art, for example in U.S. Pat. Nos. 5,476,784 and 6,099,839 (both incorporated herein by reference), as a surrogate antigen to elicit a T cell-dependent immune response against an oligosaccharide epitope of *N. gonorrhoeae*.

Peptide Mimics

The instant disclosure is directed to peptide mimics that immune-specifically (e.g., reacts, binds, or generates an immune reaction to a specific antigen or molecule) react with an antibody directed to a conserved oligosaccharide epitope of *N. gonorrhoeae*, which oligosaccharide epitope is not present in human blood group antigens. Such peptide mimics can be used in a manner similar to the anti-idiotypic antibodies described, as a surrogate antigen to elicit a T cell-dependent immune response against an oligosaccharide epitope of *N. gonorrhoeae*. The peptide mimic may be administered to uninfected subjects to induce a specific immune response directed against gonococcal organisms or cells bearing said oligosaccharide antigen. Such an immune response can be immune-prophylactic (e.g., eliciting an immune response or priming the immune system to respond in the event of an exposure) in character, in that it would prevent, and/or reduce the severity of, an infection should the recipient be exposed to the gonococcal organism or cells bearing said oligosaccharide antigen.

Accordingly, in some aspects, the disclosure relates peptide mimic, comprised of a compound (e.g., peptide mimic), having a formula, Formula (I) of:

(I)

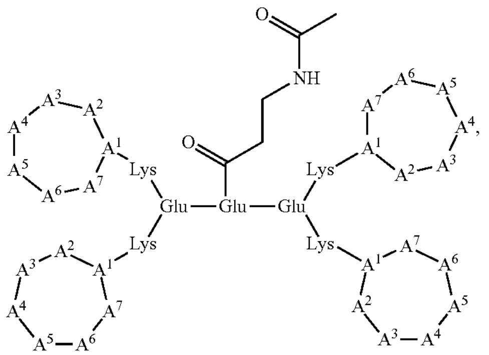

or a salt or polymorph thereof, wherein $A^1$, $A^2$, $A^3$, $A^5$, $A^6$, and $A^7$ are each independently a bond, an amino acid residue, substituted or unsubstituted acyl, substituted or unsubstituted alkylene, substituted or unsubstituted alkenylene, substituted or unsubstituted heteroalkylene, substituted or unsubstituted heterocyclylene, or substituted or unsubstituted heteroarylene, or a combination thereof; and $A^4$ is a peptidyl sequence.

In some embodiments, $A^1$, $A^2$, $A^3$, $A^5$, $A^6$, and $A^7$ are each independently an amino acid residue, substituted or unsubstituted acyl, or substituted or unsubstituted alkylene, or a combination thereof. In some embodiments, $A^1$, $A^2$, $A^3$, $A^5$, and $A^6$ are each independently an amino acid residue. In some embodiments, $A^1$, $A^2$, $A^3$, $A^5$, and $A^6$ are each independently glycine, proline, or cysteine. In some embodiments, $A^1$ is cysteine; and $A^2$, $A^3$, $A^5$, and $A^6$ are each independently glycine or proline. In some embodiments, $A^7$ is an amino acid residue, substituted or unsubstituted acyl, or substituted or unsubstituted alkylene, or a combination thereof. In some embodiments, $A^7$ is cysteine, substituted or unsubstituted acyl, or substituted or unsubstituted alkylene, or a combination thereof. In some embodiments, $A^7$ is $-(C{=}X)-CR_2-$; wherein X is O or S, and each R is independently hydrogen, substituted or unsubstituted alkyl, or halogen. In some embodiments, $A^7$ is $*-(C{=}O)-CH_2-$; wherein * indicates attachment to $A^6$.

In some embodiments, $A^4$ is an antigenic peptidyl sequence. In some embodiments, $A^4$ is a 12-mer antigenic peptidyl sequence. In some embodiments, $A^4$ is a 12-mer antigenic peptidyl sequence, wherein each amino acid residue is independently isoleucine, proline, valine, leucine, aspartic acid, glutamic acid, asparagine, glycine, phenylalanine, or alanine (SEQ ID NO.: 2). In some embodiments, $A^4$ is *-Ile-Pro-Val-Leu-Asp-Glu-Asn-Gly-Leu-Phe-Ala-Pro-(SEQ ID NO: 2); wherein * indicates attachment to $A^5$.

In some aspects, the disclosure relates to a peptide mimic, comprising a compound (e.g., peptide mimic) with a formula of Formula (I-a)

(I-a)
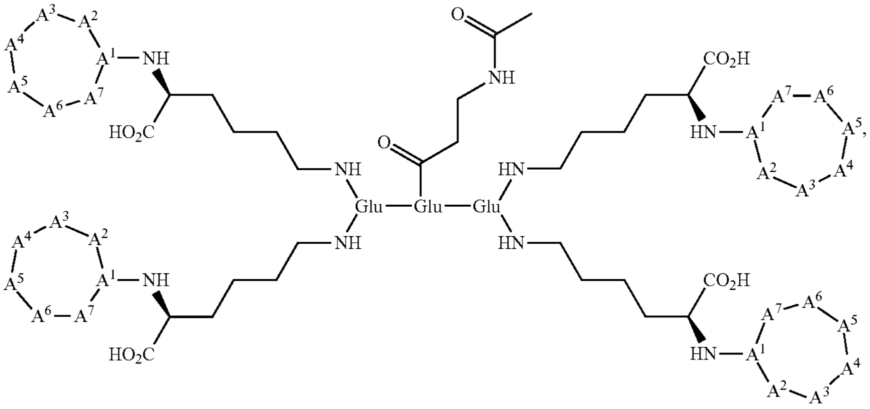
or a salt or polymorph thereof.
In some aspects, the disclosure relates to a peptide mimic, comprising a compound (e.g., peptide mimic) with a formula of Formula (I-b)
(I-b)
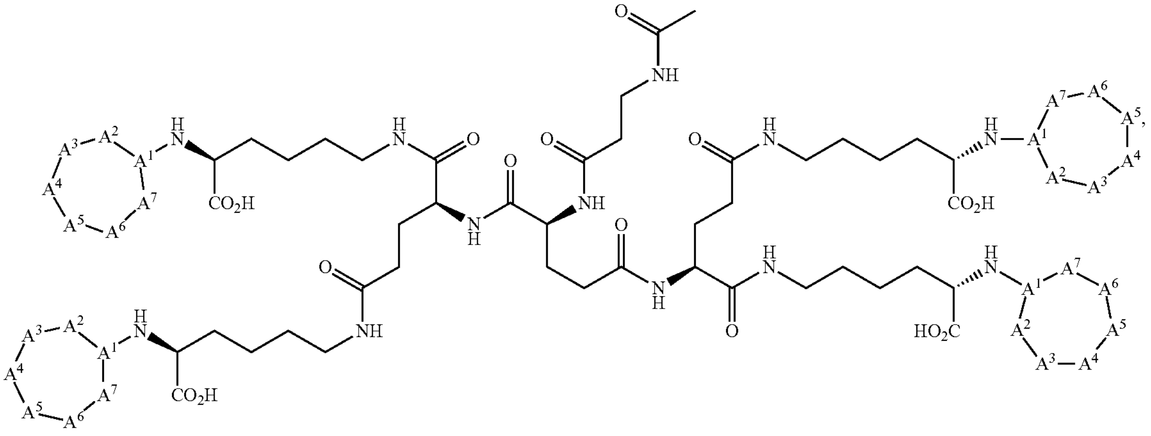
or a salt or polymorph thereof.
In some aspects, the disclosure relates to a peptide mimic, comprising a compound (e.g., peptide mimic) with a formula of Formula (I-c)

(I-c)
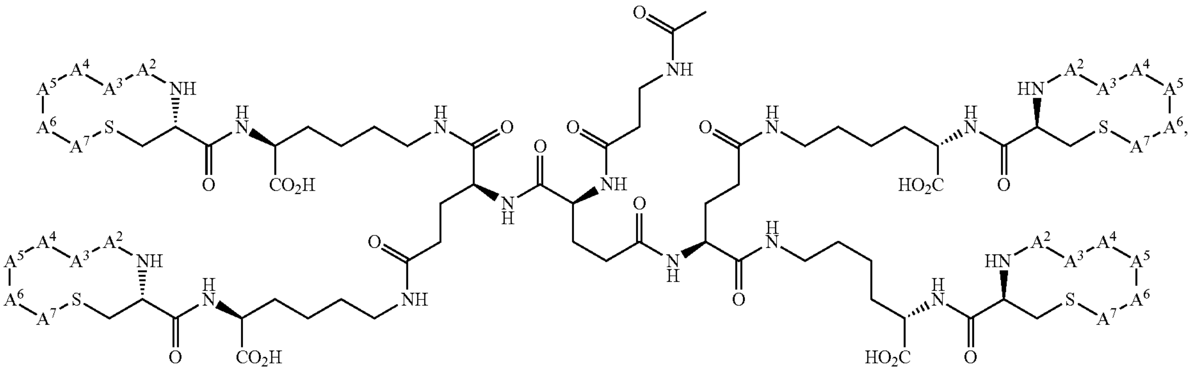
or a salt or polymorph thereof.
In some aspects, the disclosure relates to a peptide mimic, comprising a compound (e.g., peptide mimic) with a formula of Formula (I-d):
(I-d)
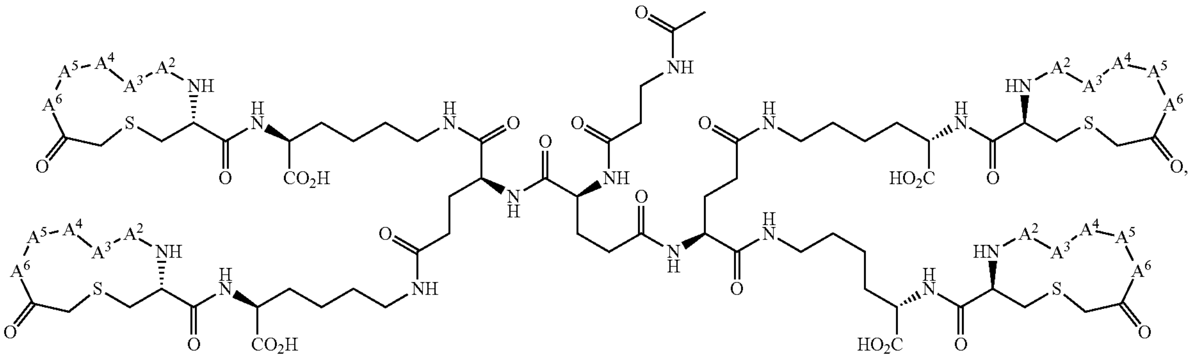
or a salt or polymorph thereof.
In some aspects, the disclosure relates to a peptide mimic, comprising a compound (e.g., peptide mimic) with a formula of Formula (I-e):
(I-e)
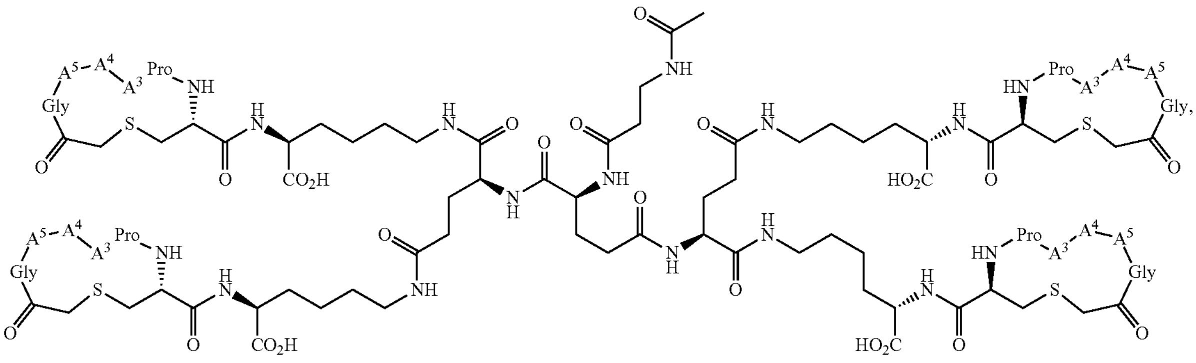
or a salt or polymorph thereof.

In some aspects, the disclosure relates to a peptide mimic, comprising a compound (e.g., peptide mimic) with a formula of Formula (I-f):

(I-f)

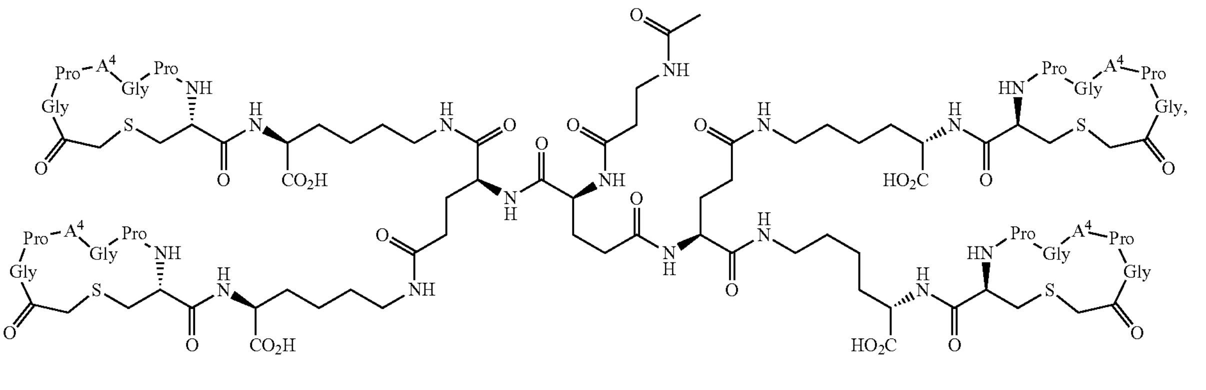

or a salt or polymorph thereof.

In some embodiments, $A^4$ of the peptide mimic with a formula, Formula (I-f), is *-Ile-Pro-Val-Leu-Asp-Glu-Asn-Gly-Leu-Phe-Ala-Pro- (SEQ ID NO: 2), wherein * indicates attachment to Pro.

In some aspects, the disclosure relates to a peptide mimic, comprising a compound (e.g., peptide mimic) of the formula

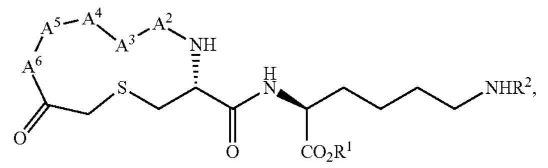

or a salt or polymorph thereof, wherein $A^2$, $A^3$, $A^5$, and $A^6$ are each independently an amino acid residue; $A^4$ is an antigenic peptidyl sequence; $R^1$ is hydrogen, a solid support resin, or a protecting group; and $R^2$ is hydrogen or a protecting group.

In some aspects, the disclosure relates to a peptide mimic, comprising a compound (e.g., peptide mimic) of the formula

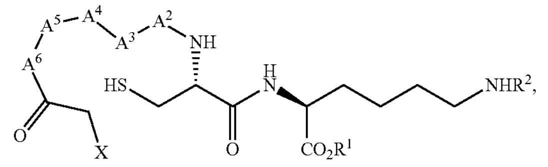

or a salt or polymorph thereof, wherein X is a leaving group; $A^2$, $A^3$, $A^5$, and $A^6$ are each independently an amino acid residue; $A^4$ is an antigenic peptidyl sequence; $R^1$ is hydrogen, a solid support resin, or a protecting group; and $R^2$ is hydrogen or a protecting group.

In some aspects, the disclosure relates to a peptide mimic of a conserved gonococcal lipo-oligosaccharide (LOS) epitope not found on human blood group antigens, wherein the peptide mimic is capable of inducing in a subject an immune response against said conserved gonococcal LOS epitope and wherein the peptide mimic comprises the amino acid sequence of SEQ ID NO: 1.

In some embodiments, the immune response induced by the peptide mimic is T-cell dependent. T-cells are a form of lymphocytes which develop in the thymus, contain T-cell Receptor (TCR), and either modulate an immune response upon recognition of a ligand or directly kill a ligand presenting cell.

In some embodiments, the peptide mimic competes with LOS) for binding to monoclonal antibody 2C7 produced by a hybridoma cell line having the ATCC accession number HB-11859. LOS (often used to refer to low molecular weight bacterial liposaccharides) are glycolipids found in the outer membrane of some types of gram-negative bacteria, such as *N. gonorrhoeae*. LOS plays a central role in maintaining the integrity and functionality of the outer membrane cell envelope and plays an important role in the pathogenesis of certain bacterial infections. Furthermore, LOS molecules are responsible for the ability of some bacterial strains to display molecular mimicry and antigenic diversity, aiding in the evasion of host immune defenses and thus contributing to the virulence of these bacterial strains.

In some embodiments, the peptide mimic immuno-specifically binds to monoclonal antibody 2C7 produced by a hybridoma cell line having the ATCC accession number HB-11859. In some embodiments, the peptide mimic immuno-specifically binds to a monoclonal antibody produced by immunizing a subject with an anti-idiotypic monoclonal antibody, or fragment thereof, wherein said anti-idiotypic monoclonal antibody is produced by a hybridoma cell line having the ATCC accession number HB-11311.

In some embodiments, a composition for immunizing against *N. gonorrhoeae* infection comprises an effective amount of any of the peptide mimics disclosed herein, or a combination thereof. In some embodiments, a composition for immunizing against *N. gonorrhoeae* infection comprising an effective amount of a peptide mimic comprising the amino acid sequence of SEQ ID NO: 1. In some embodiments, a method of immunizing a subject against *N. gonorrhoeae* infection is disclosed, comprising administering to the subject an effective amount of the one or more of the peptide mimics disclosed herein. In some embodiments, the compositions and/or agents of the disclosure (e.g., peptide mimics) comprise any of the sequences disclosed in Tables 1a-2 of the present disclosure. In some embodiments, the compositions and/or agents of the disclosure (e.g., peptide mimics) comprise a linker. In some embodiments, the compositions and/or agents of the disclosure (e.g., peptide mimics) further comprise any of the linkers as disclosed in Tables 1a-2 of the present disclosure. In some embodiments, a peptide mimic, or composition thereof, comprises a sequence with at least 70% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 99.95%, 99.99%, or more) identity to any of SEQ ID NO: 1-4, 6-9, or 11-19. In some embodiments, the peptide mimic, or composition thereof, comprises a sequence with at least 70% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, 99.95%, 99.99%, or more) identity to any of the sequences disclosed in Tables 1a-2 disclosed herein. In some embodiment, the peptide mimic, or composition thereof, comprises a sequence of any of SEQ ID NO: 1-4, 6-9, or 11-19. In some embodiment, the peptide mimic, or composition thereof, comprises a sequence of any of the sequences disclosed in Tables 1a-2 disclosed herein. In some embodiment, the peptide mimic, or composition thereof, comprises a sequence of IPVLDENGLFAP (SEQ ID NO: 2).

In some embodiments, the peptide mimic is coupled to a complement protein. A "complement protein" as used herein, refers to any protein of the complement system which operate to opsonize pathogens and induce a reaction to fight infection in the host. In some embodiment, the complement protein is C3d. Complement protein C3d is the final product of the complement component 3 (C3), which is a central protein of the immune system. When conjugated to an antigen, C3d is known to enhance immune response and is known to enhance B-cell responses. It is accordingly often used as an adjuvant to various therapeutics. In some embodiments, the complement protein is C3d.

In some embodiments, any of the peptide mimics disclosed herein may be coupled to a second agent. An "agent" as used herein, refers to any other chemical, compound (e.g., peptide mimic), adjuvant, neoadjuvant, or composition, with the primary effect of being therapeutic or prophylactic for the condition or indication being treated, for example, a secondary vaccine, treatment, prophylactic drug, food, or any other chemical, compound (e.g., peptide mimic), adjuvant, neoadjuvant, or composition with the purpose of modulating (e.g., increasing, decreasing) the effects of the peptide mimic or any side effects thereof. An "adjuvant" as used herein, refers to any therapy or treatment (e.g., composition, drug, or method based) which is used as an adjunct to the primary or initial therapy or treatment. Adjuvants may be administered concurrently (e.g., at the same time, simultaneously) with the primary or initial treatment or shortly after the administration of the primary or initial treatment. In some, but not all, cases an adjuvant modulates (e.g., increases, decreases) the effect of the primary or initial treatment. In some, but not all, cases an adjuvant is used to modulate (e.g., increase, decrease) a side effect of the primary or initial treatment. In some, but not all, cases an adjuvant is used to prepare (e.g., condition) a subject in anticipation of the primary or initial treatment or aid in the primary or initial treatment's effects or sustain or aid in the recovery of the subject after the primary or initial treatment. A "neoadjuvant" as used herein, refers to an adjuvant which is administered prior to the primary treatment. In some embodiments, the second agent is an adjuvant or neoadjuvant. In some embodiments, the second agent is an adjuvant. In some embodiments, the second agent is a neoadjuvant.

In some embodiments, the peptide mimics may include a carrier protein. A "carrier protein" as used herein, refers to a protein which carries (i.e., facilitates the transfer of) a substance (e.g., peptide mimic) from one side of a biological membrane to the other, often through conformational change in the protein after binding of the solute to be transported. Transport may be passive, down the electrochemical gradient of the carrier protein, or actively coupled to the electrochemical gradient of another solute.

In some embodiments, the peptide mimics may further comprise a pharmaceutically acceptable composition. In some embodiments, the peptide mimics described herein can be formulated for administration to a subject as a pharmaceutically acceptable composition, which as used herein, comprises the peptide mimic and another pharmaceutically acceptable carrier, diluent, or excipient). A carrier, diluent, or excipient that is "pharmaceutically acceptable" includes one that is sterile and pyrogen free. Suitable pharmaceutical carriers, diluents, and excipients are well known in the art. The carrier(s) must be "acceptable" in the sense of being compatible with the inhibitor and not deleterious to the recipients thereof.

Formulations suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. Aqueous solutions may be suitably buffered (preferably to a pH of from 3 to 9). The preparation of suitable parenteral formulations under sterile conditions is readily accomplished by standard pharmaceutical techniques well-known to those skilled in the art.

Any of the peptide mimics described herein may be administered by any administration route known in the art, such as parenteral administration, oral administration, buccal administration, sublingual administration (e.g., tablets, capsules, ovules, elixirs, solutions or suspensions, which may contain flavoring or coloring agents, for immediate-, delayed- or controlled-release applications) topical administration, or inhalation, in the form of a pharmaceutical formulation comprising the active ingredient, optionally in the form of a non-toxic organic, or inorganic, acid, or base, addition salt, in a pharmaceutically acceptable dosage form. Suitable tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds (e.g., peptide mimics) of the disclosure may be combined with various sweetening or flavoring agents, coloring matter or dyes, with emulsifying and/or suspending agents and with diluents such as water, ethanol, propylene glycol and glycerin, and combinations thereof. Additionally, lubricating agents such as magnesium stearate, stearic acid, glyceryl behenate and talc may be included.

In some embodiments, the administration route is oral administration and the formulation is formulated for oral administration. In other embodiments, the administration route is rectal (e.g., intrarectal) and the composition is formulated for rectal administration.

The formulations may be presented in unit-dose or multi-dose containers, for example sealed ampoules or vials, and may be stored in a freeze-dried (lyophilized) condition requiring only the addition of the sterile liquid carrier immediately prior to use.

In some embodiments, any of the agents described herein can be administered to a subject at a dose of between 15 and 150 μg per subject or between 0.25 to 2.2 μg/kg per subject. In some embodiments, any of the agents described herein can be administered to a subject in single or divided doses. In some embodiments, any of the agents described herein is administered to a subject in a single dose. In some embodiments, any of the agents described is administered to a subject in divided doses (e.g., multiple or sequential doses). In some embodiments, any of the agents described herein can be administered to a subject at a dose of between 25 and 100 μg per subject or between 0.4 to 1.7 μg/kg per subject, administered in single or divided doses (e.g., multiple or sequential doses). A physician in any event may determine the actual dosage which will be most suitable for any subject, which will vary with the age, weight and the particular disease or disorder to be treated or prevented.

Therapeutic Applications

Aspects of the disclosure relate to a method of modulating immune responses, for example, immune responses mediated by peptide mimics as described herein. To perform such a method, an effective amount of the peptide mimics as described herein can be administered as described herein.

In some embodiments, the method described herein comprises administering an effective amount of a peptide mimic or a composition comprising one or more peptide mimics to a subject in need of the treatment. The subject may be a human subject who has, or is at risk for infection from, *N. gonorrhoeae*. Such a subject may be on antibiotic treatment (e.g., have undergone an antibiotic treatment or is currently treated with antibiotics).

In some embodiments, peptide mimics as described herein can be administered at a specific period before, during, or after a target indication (e.g., infection by *N. gonorrhoeae*) has occurred in the subject. In some embodiments, peptide mimics as described herein is administered prior to manifestation of one or more symptoms of the target indication. In other embodiments, the peptide mimics as described herein are administered to the subject during or after manifestation of one or more symptoms of the target indication, or during or after occurrence of the target indication, such as within 12 or 24 hours of an infection or manifestation of one or more symptoms of the indication. In some embodiments, the peptide mimics as described herein are administered to the subject within 7 days (e.g., within 7, 6, 5, 4, 3, 2, or 1 days) after the subject is infected with a pathogen such as a bacterium or a virus, or manifests a symptom of the infection.

In some embodiments, the peptide mimics as described herein can be administered at a specific period before, during, or after an antibiotic treatment. In some embodiments, the peptide mimics as described herein are administered prior to an antibiotic treatment. In other embodiments, the peptide mimics as described herein are administered to the subject during or after the antibiotic treatment, such as within 12 or 24 hours of the antibiotic treatment. In some embodiments, the peptide mimics as described herein are administered to the subject within 6 months (e.g., within 3 months, within 2 months, within 1 month, or with 2 weeks) after the subject is treated with an antibiotic. Infection can be detected using any method known in the art. In some embodiments, the subject has one or more symptoms of infection. In some embodiments, the subject is not, or has not, manifested any symptoms.

Methods and compositions described herein are meant for any subject that has or is at risk of any of the target disorders described herein.

Kits for Modulating Immune Responses

Another aspect of the present disclosure relates to kits for use in modulating immune responses of subjects infected with, or at risk of being infected with, *N. gonorrhoeae*. Accordingly, in some embodiments, such a kit can comprise one or more of the active agents described herein, including the peptide mimics as described herein, or a pharmaceutical composition comprising the same, or a dietary supplement comprising the same.

In some embodiments, the kit can comprise instructions for use in accordance with any of the methods described herein. The instructions can comprise a description of administration of the peptide mimics as described herein, or a pharmaceutical composition comprising the same, for modulating immune responses and/or alleviating any of the target indications described herein. The instructions relating to the peptide mimics as described herein, or a pharmaceutical composition comprising the same, generally include information as to dosage, dosing schedule, and route of administration for the intended treatment. Such instructions may also include recommended weight-based dosages and/or age-based dosages.

Instructions supplied in the kits described herein are typically written instructions on a label or package insert (e.g., a paper sheet included in the kit), but machine-readable instructions (e.g., instructions carried on a magnetic or optical storage disk) are also acceptable. The label or package insert indicates that the composition is used for immune modulation or treatment of a target indication in subjects. In some embodiments, the label or package insert may indicate that the composition is suitable for use in specific groups of subjects, e.g., as described herein. For example, the label or package insert may indicate that the composition is suitable for use in human patients. Instructions may be provided for practicing any of the methods described herein.

The peptide mimics as described herein, or a pharmaceutical composition comprising the same in the kit may be in suitable packaging. Suitable packaging includes, but is not limited to, vials, bottles, jars, flexible packaging (e.g., sealed Mylar or plastic bags or paper bags with a polyethylene liner), and the like. The packaging may be in unit doses, bulk packages (e.g., multi-dose packages) or sub-unit doses.

Kits may optionally provide additional components such as buffers and interpretive information. Normally, the kit comprises a container and a label or package insert(s) on or associated with the container.

Without further elaboration, it is believed that one skilled in the art can, based on the above description, utilize the disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Activation of the classical pathway of complement requires engagement of the C1 complex (subunits of C1q, C1r, and C1s), triggered by Fc antibody domains. Upon binding to surfaces, Fc domains of proximate IgG molecules form ordered hexamers through non-covalent interactions, which then simultaneously engage multiple globular heads of C1q, also a hexameric molecule. Multimeric interactions between globular domains of C1q and Fe convert otherwise low-affinity monomeric IgG Fc-C1q associations to interactions of high avidity, which permits autocatalysis of C1r and further complement activation. An effective bactericidal antibody requires a critical density of surface targets to engage C1q and permit complement activation. On a molar basis, LOS is the most abundant gonococcal outer membrane molecule and serves as a convenient target for binding of closely spaced antibody molecules whose Fc domains can then readily engage the C1 complex an activate complement. An intact complement pathway is necessary and sufficient for efficacy of mAb 2C7 in the mouse vaginal colonization model (Gulati S et al. PLoS Biol. 2019 Jun. 19; 17(6): e3000323. PMID: 31216278). The importance of complement in host defenses against gonorrhea, is highlighted by the observation that both congenital and acquired defects of individual terminal components of complement are associated with an increased incidence of disseminated gonococcal infection (DGI). Based on the data with mAb 2C7, it is proposed that attenuation of colonization by antibodies elicited by TMCP2 vaccine also occurs via complement-dependent bactericidal antibody activity. A vaccine candidate that comprises gonococcal outer membrane vesicles plus microencapsulated IL-12 given intravaginally requires B cell activity, presumably to produce antibodies, however, a requirement for complement has not been shown.

No other gonococcal vaccine candidates tested in the cervico-vaginal colonization model in estradiol-treated mice show sterilizing immunity. Immunomodulatory effects of estrogen may curb immune defenses that are important to clear *N. gonorrhoeae*. Seminal studies showed that the activity of terminal complement components in male mice exceeds, by 8-to10-fold, activity in female mice. Administration of testosterone increases complement activity; estrogen has the opposite effect. Therefore, a vaccine antibody response that utilizes terminal complement to act in concert with the bactericidal action of antibody may also require waning of the suppressive effects of estrogen on terminal complement components before full bactericidal activity is restored.

A retrospective epidemiologic analysis showed that a detergent extracted meningococcal outer membrane vesicle (dOMV) vaccine called MeNZB designed and implemented in a widespread vaccination program to control an epidemic of group B meningococcal disease in New Zealand, showed diminished coverage in populations subsequently infected with *N. gonorrhoeae*—calculated as 31% effectiveness of MenZB in decreasing gonococcal infection—reduced to 14% in populations co-infected with *N. gonorrhoeae* and *Chlamydia*, a frequent clinical occurrence. Meningococci and gonococci share several similarities and it is possible that one or more proteins in MeNZB that cross-react with *N. gonorrhoeae* may elicit protective immune responses. Subjects administered a licensed group B meningococcal vaccine, BEXSERO®, which contains 5 recombinant meningococcal protein antigens in addition to the same dOMV that constitutes MeNZB, elicit antibodies, immunochemically, that cross-react with *N. gonorrhoeae*. However, in a separate study, bactericidal antibody activity against *N. gonorrhoeae* FA1090 in immune sera from subjects vaccinated with BEXSERO® was not observed. How MeNZB provides protection against gonorrhea remains unclear. Currently, several gonococcal vaccine candidates are undergoing preclinical evaluation, some of which elicit bactericidal activity. Knowledge of the immune defenses responsible for clearing gonococcal infection is an important aspect of developing effective vaccines against this disease.

Three glycosyltransferase genes—lgtA, lgtC, lgtD—involved in LOS biosynthesis are phase-variable because of slipped-strand mispairing of homopolymeric poly-G tracts in their open reading frames; a fourth, lgtG, containing a poly-C tract is also phase variable. Expression of the 2C7 epitope requires lgtG to be phase-varied 'on'; expression status of the three other lgt genes modulate binding of mAb 2C7 to LOS. As discussed above, the 2C7 LOS epitope is expressed almost universally in vivo and by minimally passaged isolates. The 2C7 epitope was identified in 64 of 68 (94%) gonococcal isolates examined directly in cervical secretions from women in a sexually transmitted disease clinic in Boston in the early 1990s and 96 of 101 (95%) of randomly chosen minimally (second-passage) isolates. Recently, it was reported that 100% of 75 minimally passaged isolates from China also expressed the 2C7 epitope. Importantly, mAb 2C7 was bactericidal (>50% killing) against each (100%) of the 62 isolates tested in complement-dependent bactericidal assays, including strains that expressed very low levels of the epitope. Because LOS is the most abundant outer membrane molecule on gonococci, expression of the 2C7 epitope on even a small fraction of LOS may permit binding of antibody at a density sufficient to engage the C1 complex and activate the classical pathway. It is speculated that widespread expression of this epitope results from gonococci's ability to sialylate lactose expressed from Hep II, which facilitates engagement of Siglec receptors. Many Siglec receptors signal through their immunoreceptor tyrosine-based inhibitory motif (ITIM) tails to dampen host inflammatory responses that otherwise sense invading pathogens. Neu5Ac (sialic acid) that caps lactose from Hep II also inhibits complement C3 deposition on the bacterial surface. Genetic deletion of lgtG markedly attenuates the ability of *N. gonorrhoeae* to colonize the vagina of estradiol-treated mice. Additional evidence for the importance of lgtG expression was provided by Lam and Gray-Owen, who showed that serial passage of *N. gonorrhoeae* in mice was accompanied by increased fitness of bacteria with each generation—i.e., an increasing fraction of mice could be infected with bacteria recovered from each successive mouse passage. Intriguingly, there was a reproducible positive selection for gonococcal variants with lgtG 'on'. Resistance to antibodies elicited by a '2C7 vaccine' would require lgtG to be turned completely 'off'. Based on the accumulated evidence from: studies of minimally passaged isolates; bacteria examined directly ex vivo from humans (without passage on media) and studies in mice—as discussed above, it is proposed that mutations in gonococci that eliminate 2C7 LOS epitope would render the organism less fit and avirulent. From a public health perspective, translation to a decrease in burden and duration of infection can have profound effects on disease pathology and transmission. In conclusion, TMCP2 represents an important step forward in the development of a safe, economical and effective gonococcal vaccine, or subcomponent thereof.

In order that this disclosure may be better understood, the following examples are set forth. These examples are for purposes of illustration only, and are not to be construed as limiting the scope of the disclosure in any manner.

Example 1: Peptide Mimics Elicit Immunogenic Response

Materials and Methods

Bacterial Strains

*N. gonorrhoeae* strain FA1090 (Opa+, Pil+) (20), MS11 (Opa+, Pil+) (21), 15253 (22) and 15253 ΔlgtG (isogenic mutant of 15253 with lgtG deleted; does not react with mAb 2C7) (16).

Purification of LOS

LOS was purified from strains 15253 and 15253 ΔlgtG using the hot water phenol extraction method (23).

Materials for Production of TMCP-2

The peptide mimic (also referred to herein as TMCP2) was synthesized using a solid phase approach for the thioether peptide component and a classical solution phase method for production of the reverse peptide mimic core and final tetra peptide mimic construct. Briefly, the thioether monomer was synthesized on a Fmoc-Lys-Wang resin using standard Fmoc-tBu amino acid derivatives. At the completion of assembly of the protected linear peptide sequence: H-Gly-Pro-(Ile-Pro-Val-Leu-Asp-Glu-Asn-Gly-Leu-Phe-Ala-Pro)-Gly-Pro-Cys-Lys-OH (SEQ ID NO: 7)-, bromoacetic acid was coupled to the N-terminus via symmetric anhydride coupling. The peptide Br-Ac-Gly-Pro-Ile-Pro-Val-Leu-Asp-Glu-Asn-Gly-Leu-Phe-Ala-Pro-Gly-Pro-Cys-Lys-OH (SEQ ID NO: 7) was cleaved from the solid support and simultaneously de-protected using trifluoroacetic acid containing $H_2O$ and triisopropyl silane as cationic scavengers. The crude linear peptide was purified using preparative HPLC and subsequently cyclized by dilution into 1% $Na_2CO_3$ buffer to a concentration of 0.3 mg/ml. Cyclization was completed at 18 hour and the cyclic thioether peptide (structure indicated 'peptide mimic Core Peptide 2' in FIG. 1A) was purified via preparative RP-HPLC. Fractions which had a purity of >90% by analytical HPLC were pooled and lyophilized. The cyclic thioether monomer peptide was characterized using ESI-MS (calculated m/z=1864.17; found m/z=1864.88).

The reverse peptide mimic core construct was synthesized starting with Ac-β-Ala-OH. $H\text{-}Glu(OBz1)_2$ was coupled to the Ac-β-Ala-OH using diphenylphosphoryl azide. The benzyl groups were liberated via catalytic hydrogenation. Ac-β-Ala-Glu-OH was subsequently reacted with 2 equivalents of $H\text{-}Glu(OBz1)_2$. The benzyl groups were removed again via catalytic hydrogenation. The final reverse tetra peptide mimic core peptide $Ac\text{-}\beta\text{-}Ala\text{-}Glu[Glu\text{-}OH]_2$ ('Reverse peptide mimic Core' in FIG. 1A) was isolated and characterized by ESI MS: calculated m/z=519.19; found m/z=519.22. This compound was subsequently activated to the tetra NHS ester in the presence of diisopropyl carbodiimide.

Figure 6:
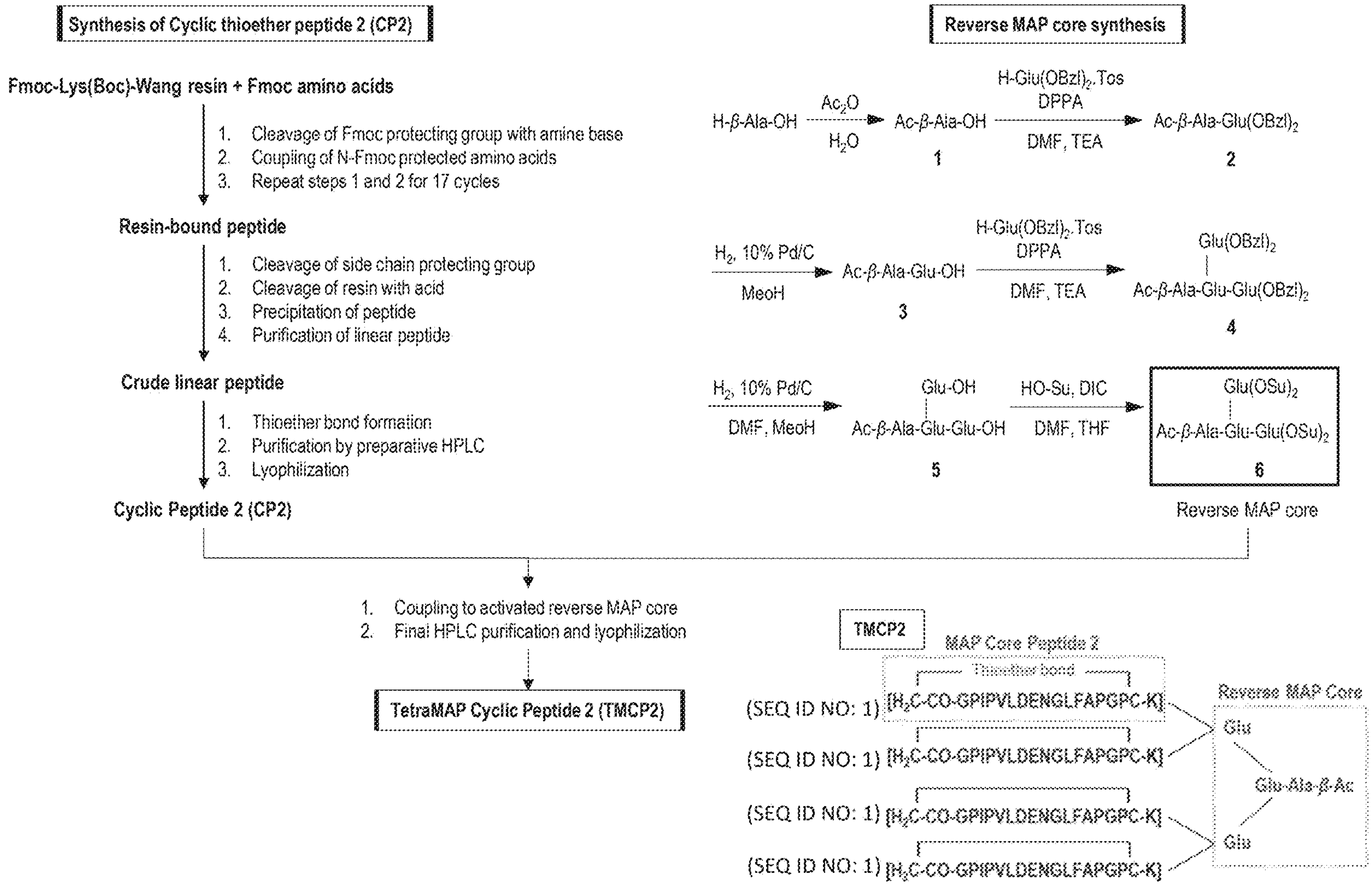
FIG. 6 shows schematic describing the steps in the synthesis of TMCP2. Multi-antigen peptide (peptide mimic); acetic anhydride (Ac2O); N,N-dimethylformamide (DMF); diphenylphosphoryl azide (DPPA); Glutamic acid 1-benzyl ester (Glu(OBz1)); triethylamine (TEA); N-hydroxysuccinimide (HO-Su); diisopropylcarbodiimide (DIC); palladium on carbon catalyst (Pd/C).

TCMP-2 was synthesized by adding 4.2 equivalents of the cyclic thioether peptide mimic Core Peptide 2 to the Reverse peptide mimic Core ($Ac\text{-}\beta\text{-}Ala\text{-}Glu[Glu(OSu)_2]_2$). Following coupling for 20 hours, the crude peptide tetra peptide mimic TMCP-2 was isolated by preparative RP-HPLC. The resulting fractions with a purity >95% were pooled and lyophilized. The final product TCMP-2 was isolated and characterized by ESI-MS (resulting TMCP-2 structure shown in FIG. 1A). FIG. 6 shows a summary of the synthesis procedure.

Immunization of Mice

Six week-old female BALB/c mice were immunized with TMCP2 (dose specified for each experiment) and GLA-SE (5 g) as the adjuvant. Control mice received GLA-SE adjuvant alone. Sera were collected two weeks after each immunization.

ELISA to Measure Anti-LOS Antibody Levels

Microtiter wells were coated with LOS purified from 15253 or 15253 ΔlgtG (80 μg/ml) in PBS as described previously. Serial dilutions of immune sera were dispensed into wells and bound anti-LOS Ab was disclosed with anti-mouse IgG conjugated to alkaline phosphatase. A standard curve for mouse IgG was generated by coating wells with anti-mouse IgG (Sigma) and pure mouse IgG (Sigma) also as described previously.

Inhibition ELISA

In order to compare antigenicity of peptide mimic Core Peptide 2 (monomeric cyclic CP2) and composite TMCP2 compounds with LOS that expresses the 2C7 epitope, inhibition ELISA was performed using mAb 2C7 reacted with the individual compounds to assess inhibition of binding (residual binding) of mAb to LOS by each compound. Microtiter wells were coated with LOS (80 μg/ml in PBS) purified from strain FA1090. Wells were washed and blocked with PBS-0.05% Tween 20. mAb 2C7 (0.04 μg/ml) either alone or containing monomeric cyclic peptide CP2 (1.07 to 1070 μM) or composite TMCP2 (concentrations ranging from 0.25 to 250 PM) was dispended into LOS coated wells. Residual binding of 2C7 mAb was measured with anti-mouse IgG conjugated to alkaline phosphatase. Bound IgG was quantitated using a mouse IgG standard curve and percent inhibition determined compared to reaction mixtures that contained LOS (full inhibition).

Depletion of Mouse IgM

Because earlier it was observed that sera from naïve and mice given adjuvant alone manifest bactericidal activity mediated by IgM, mouse IgM was depleted from all sera collected as part of immunization studies. Sera from mice diluted 1:1 in PBS was mixed with anti-mouse IgM agarose (Sigma; binding capacity ≥0.4 mg/ml) (1 volume of packed agarose to 1 volume of serum diluted 1:1) in a 2.0 ml microspin filter column (Costar) with a pore size of 0.22 μM) for 15 min at 22° C. Filter-sterilized IgM depleted sera were collected by centrifugation of the mixture at 1000 g for 2 min and heat-inactivated (56° C. for 30 min) to eliminate intrinsic complement activity in mouse serum prior to use in serum bactericidal assays where human complement was substituted.

Serum Bactericidal Assays

Serum bactericidal assays were performed. Bacteria that had been harvested from an overnight culture on chocolate agar plates were repassaged onto fresh chocolate agar and allowed to grow for 6 h at 37° C. in an atmosphere containing 5% $CO_2$. Bacteria were then suspended in HBSS containing 1 mM MgCl2 and 0.15 mM $CaCl_2$) (HBSS++) for use in serum bactericidal assays. Briefly, about 2000 colony forming units (CFUs) of *N. gonorrhoeae* FA090 were incubated with serial dilutions of immune mouse sera (heat-inactivated and IgM-depleted) in the presence or absence of 20% normal human serum (NHS) as a source of human complement. Serum bactericidal assays with strain MS11 were performed with IgG and IgM depleted NHS (Human complement; Pel-Freez) because this strain is susceptible to killing by NHS. Final volumes of bactericidal reaction mixtures were 150 μl. Aliquots of 25-μl reaction mixtures were plated onto chocolate agar in duplicate at the beginning of the assay (to) and again after incubation at 37° C. for 30 min ($t_{30}$). Survival was calculated as the number of viable colonies at $t_{30}$ relative to $t_0$.

Mouse Protection Experiments

Use of animals in this study was performed in strict accordance with the recommendations in the Guide for the Care and Use of Laboratory Animals of the National Institutes of Health. The protocol was approved by the Institutional Animal Care and Use Committee (IACUC) at the University of Massachusetts Medical School. The BALB/c mouse model of vaginal colonization described by Jerse was used (25). Two weeks after the last immunization, mice in the diestrus phase of the estrous cycle were started on treatment (that day) with 0.1 mg PREMARIN® (Pfizer; a mixture of sodium estrone sulfate and sodium equilin sulfate also containing sodium sulfate conjugates of 17α-dihydroequilin, 17α-estradiol and 17β-dihydroequilin) in 200 μl of water, given subcutaneously on each of three days; −2, 0 and +2 days (before, the day of and after gonococcal inoculation) to prolong the estrus phase of the reproductive cycle and promote susceptibility to *N. gonorrhoeae* infection. Antibiotics (vancomycin and streptomycin) ineffective against *N. gonorrhoeae* were also used to reduce competitive microflora (26). Mice were infected on Day 0 with either strain FA1090 or MS11 (inoculum specified for each experiment). Vaginas were swabbed daily to enumerate gonococcal CFU.

Statistical Analyses

Experiments that compared clearance of *N. gonorrhoeae* in independent groups of mice estimated and tested three characteristics of the data (13): 1) time to clearance; 2) longitudinal trends in mean $\log_{10}$ CFU; 3) and the cumulative CFU as area under the curve (AUC). Statistical analyses were performed using mice that initially yielded bacterial colonies on Days 1 and/or 2. Median time to clearance was estimated using Kaplan-Meier survival curves; times to clearance were compared between groups using the Mantel-Cox log-rank test. Mean $\log_{10}$ CFU trends over time were compared between groups using a linear mixed model with mouse as the random effect using both a random intercept and a random slope. A quadratic or cubic function in time was determined to provide the best fit; random slopes were linear in time. A likelihood ratio test was used to compare nested models (with and without the interaction term of group and time) to test whether the trend differed over time between the two groups. The mean AUC ($\log_{10}$ CFU versus time) was computed for each mouse to estimate the bacterial burden over time (cumulative infection); the means under the curves were compared between groups using the non-parametric two-sample Wilcoxon rank-sum (Mann-Whitney) test because distributions were skewed or kurtotic. The Kruskal-Wallis equality-of-populations rank test was also applied to compare more than two groups in an experiment.

Results

Characterization of TMCP2

Figure 7:
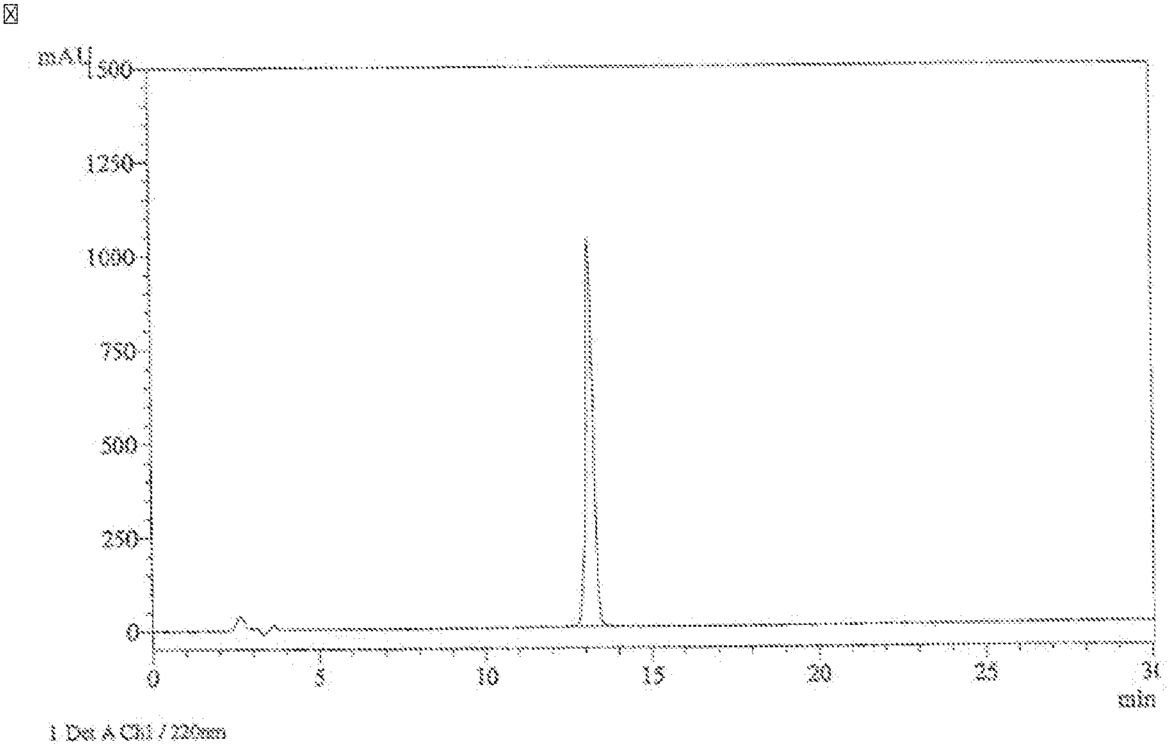
FIG. 7 shows the purity of TMCP2 determined by high-performance reverse-phase separation. TMCP2 was analyzed using a YMC-Pack-ODS-A C18 column (4.6 mm×250 mm) with a particle size of 5 μm and pore size of 200 Å using a linear gradient of 0.05% trifluoroacetic acid (TFA) versus acetonitrile (MeCN) as the nonpolar solvent at a flow rate of 1 ml/min. A major peak (99% of the total area) at 13.155 min was noted.
Figure 8:
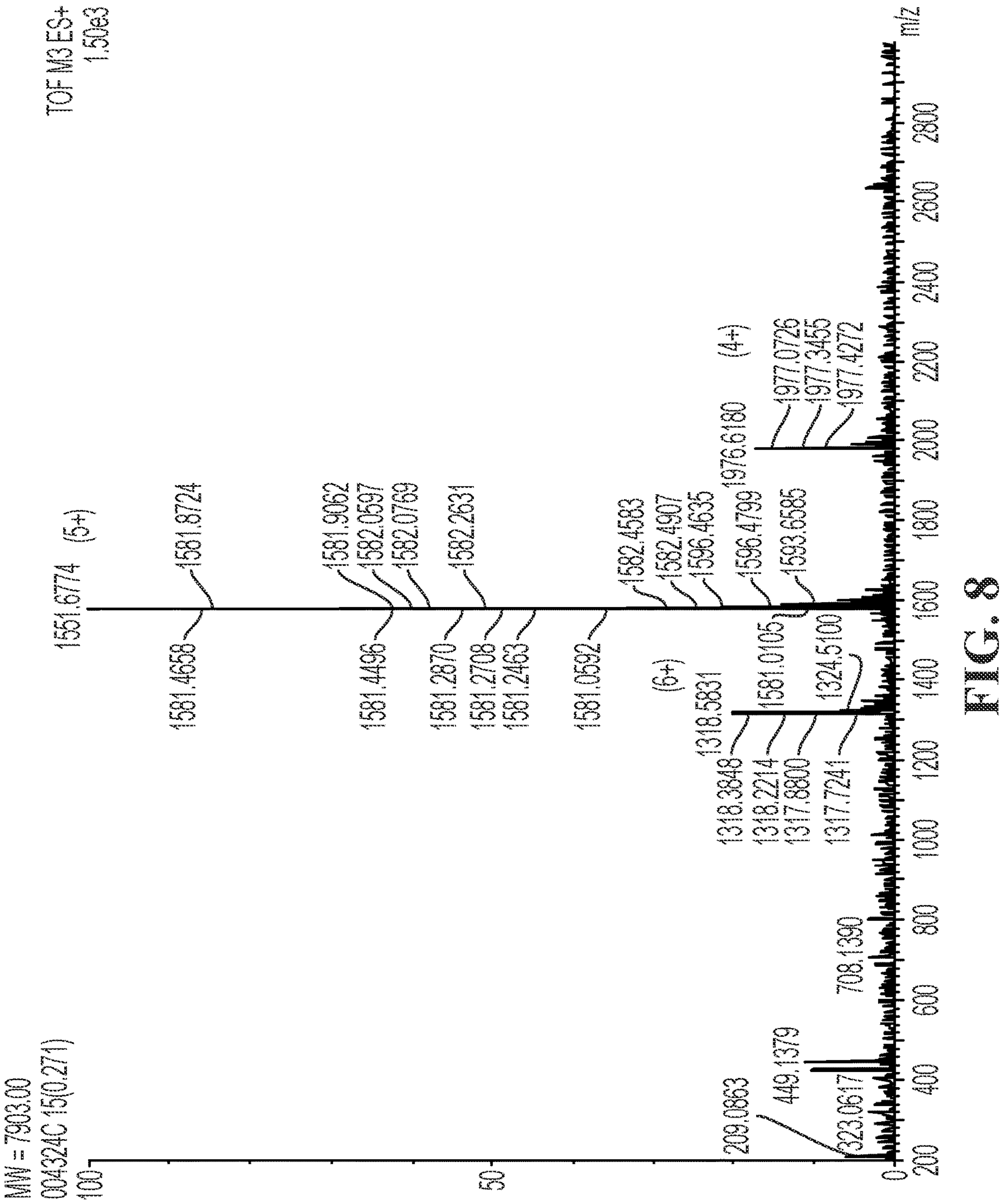
FIG. 8 shows positive electrospray ionization time-of-flight mass spectrometry (TOF MS ES+) of purified TMCP2. The TMCP2 peptide mimic peptide was highly homogeneous by both analytical RP-HPLC as well as ESI-MS where the multicharged ions at M+4 (m/z=1976.62), M+5 (m/z=1581.68) and M+6 (m/z=1318.56).
Figure 15:
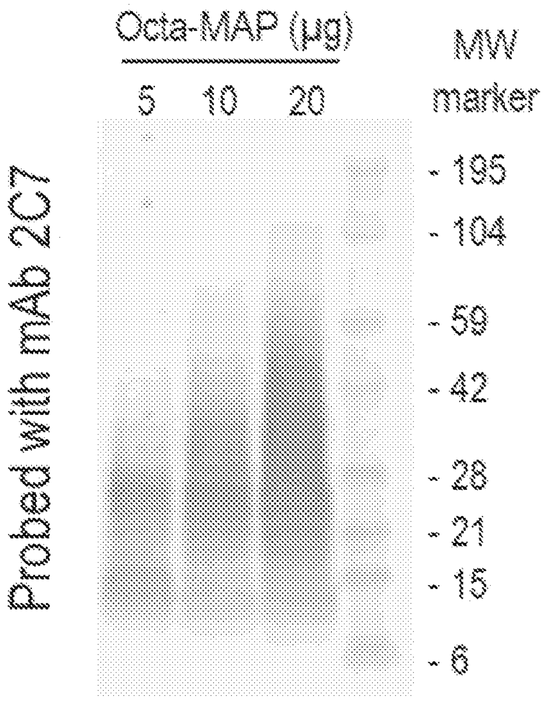
FIG. 15 shows western blot analysis of Octa-MAP 1 product.

Initial synthesis of the multivalent antigenic peptide (Octa-MAP) as a vaccine candidate that encompassed 8 copies of the mimitope of the 2C7 epitope (termed PEP1) onto a lysine core (13), yielded a heterogeneous compound because of reversible disulfide bonding between the terminally located Cys residues on PEP1 Internal bonding within the same molecule and externally to other like molecules resulted in a pattern of extreme MW heterogeneity (Table 1A and FIG. 15). In order to synthesize a stable homogenous compound, potentially suitable for clinical use, several strategies were undertaken, further documented in Tables 1A-1H, Table 2, FIG. 9, FIG. 10 and FIG. 11). A final stable compound that circularized the mimitope via a stable non-reducible (covalent) thioether bond between the terminal cysteines in linear PEP1, formed the cyclized peptide (renamed monomeric Cyclic Peptide 2 [CP2]) that was linked to each of four lysines in a scaffold where —NH2 groups on lysines, in turn, were linked to —COOH groups on glutamate molecules in a core that formed the basis of the tetrameric CP2 structure (termed TMCP2) (FIG. 1A). The purity of TMCP2 determined by high-performance reverse-phase (RP-HPLC) separation showed a major peak (99% of the total area) at 13.155 min (FIG. 7). The identity of TMCP2 was verified with positive electrospray ionization time-of-flight mass spectrometry (TOF MS ES+) (FIG. 8) that showed multicharged ions at M+4 (m/z=1976.62), M+5 (m/z=1581.68), and M+6 (m/z=1318.56). The TMCP2 tetra MAP peptide was highly homogeneous as determined by RP-HPLC; ESI-MS supporting the validity of this conclusion.

Figure 1B:
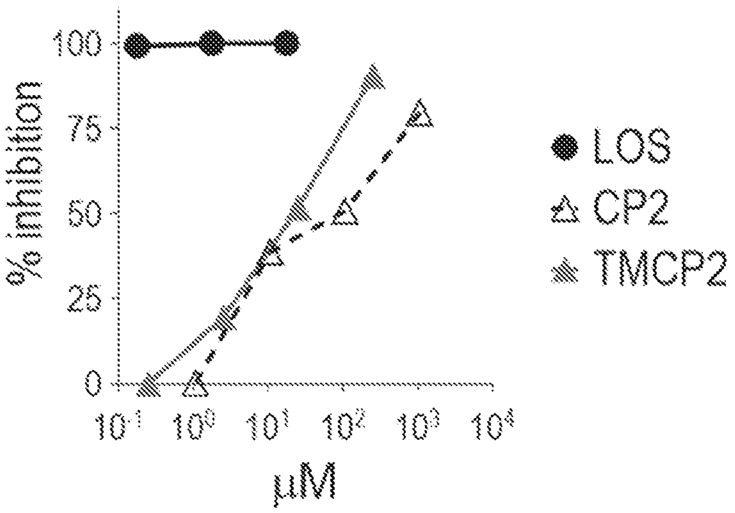

Attempts to measure mAb 2C7 (7) binding directly to immobilized peptide mimic Core Peptide 2 (abbreviated CP2 in FIG. 1A) and composite TMCP2 by ELISA were not successful. The possibility of poor capture of the peptides by the microtiter wells was considered and therefore used an ELISA to measure inhibition of binding (residual binding) of mAb 2C7 to immobilized gonococcal LOS that had been reacted with increasing concentrations of the peptides (FIG. 1B). 50% inhibition of mAb 2C7 binding to immobilized 15253 LOS in the presence of 25 μM and 107 μM of TMCP2 and CP2, respectively, was observed; the −4-fold lower molar concentration of TMCP2 (compared to CP2) required to achieve 50% inhibition is consistent with its tetrameric nature; overall higher avidity and maintenance of the 4:1 molar ratio in binding experiments ensured that linking CP2 to the 'peptide mimic' Core did not alter antigenicity of the final compound. Purified LOS, used as a positive control, completely inhibited mAb 2C7 binding to immobilized LOS even at the lowest concentration (0.178 μM) tested.

Choice of Lead Adjuvant

Figure 12A:
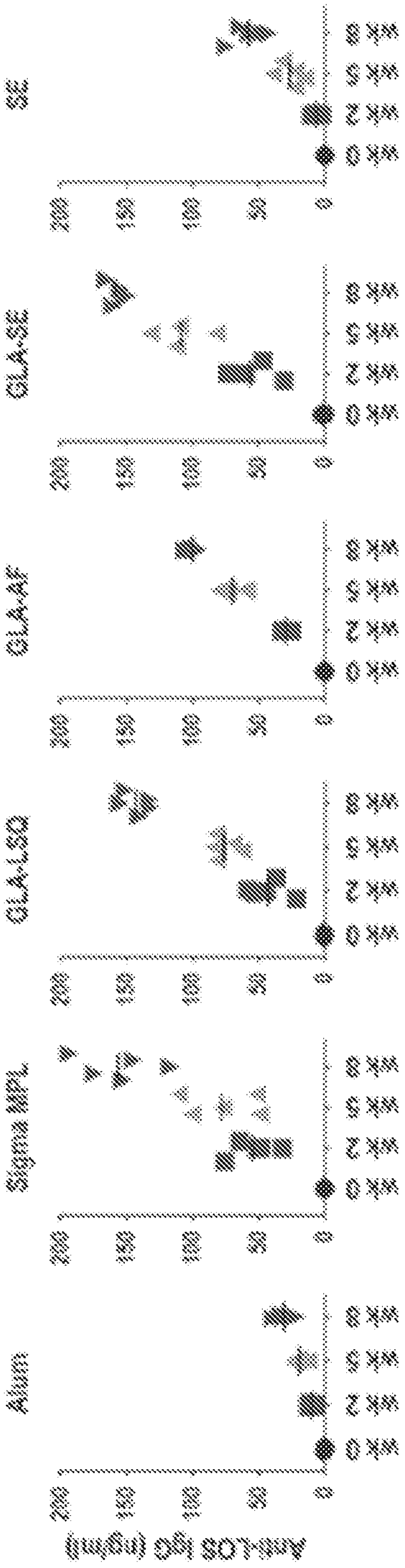
FIGS. 12A-12B show GLA-SE as the adjuvant for tetra-MAP vaccine candidate TMCP2.
Figure 12B:
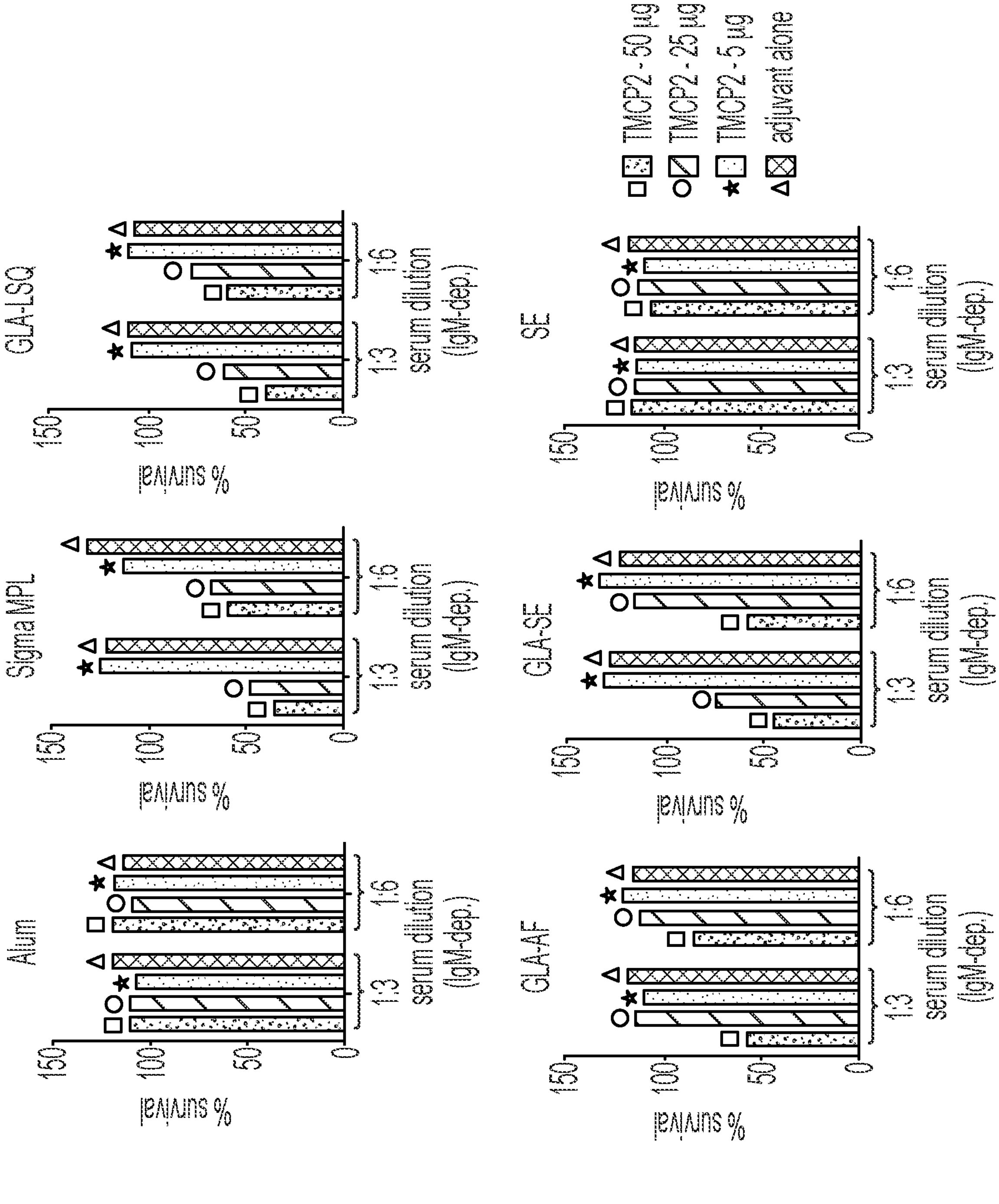

TMCP2 was tested with three additional adjuvants with properties similar to Sigma MPL: (i) Glucopyranosyl Lipid Adjuvant (GLA) in a stable oil-in-water nanoemulsion (SE) (GLA-SE); (ii) GLA-Liposome QS21 (GLA-LSQ; QS-21 is a water-soluble extract of the *Quillaja saponaria* [soap bark] tree) and (iii) GLA-Aqueous formulation (GLA-AF) (FIGS. 12A-12B). Sigma MPL adjuvant was a control. Alum (Alhydrogel) and the stable oil-in-water nanoemulsion (SE) were also tested. GLA-SE and GLA-SQ yielded the highest anti-LOS IgG titers, similar to those elicited by Sigma MPL; GLA-AF gave intermediate titers, while Alum and SE yielded low titers (FIG. 12A).

In light of the importance of complement-dependent killing for the activity of mAb 2C7 in vivo (58), serum bactericidal assays were performed to assess functionality of immune antibodies. During the course of the antigen optimization and adjuvant selection studies (performed between mid-2016 and early-2018), heat-inactivated (56° C. for 30 min) mouse sera (used to deplete endogenous complement) from naïve mice or mice given adjuvant alone (control mice sera) supported complement-dependent bactericidal activity against strain FA1090 when normal human serum (NHS) was added as the source of complement; FA1090 is highly resistant to the bactericidal action of NHS alone (27). Control mouse sera plus heat-inactivated (56° C. for 30 min) NHS failed to kill gonococci, suggesting that observed killing was complement dependent. A systematic analysis of the bactericidal activity of heat-inactivated sera with added NHS from several strains of naïve mice from different sources was carried out (Table 3). Except for Rag−/− and JhD mice that both lack antibody, heat-inactivated sera from all other mice tested supported human complement-dependent killing of *N. gonorrhoeae*. Similarly, bactericidal activity was supported by sera from CD1 mice housed at the Childrens Hospital Oakland Research Institute, Oakland, CA given Alum adjuvant (28).

Absorption of naïve or adjuvant control mouse sera against anti-mouse IgM-linked agarose, but not protein A/G agarose (depletes IgG), abrogated bactericidal activity (survival >80%), revealing IgM as the antibody subclass responsible for the underlying bactericidal activity. Mouse sera used in (human) complement-dependent bactericidal assays in adjuvant selection studies was depleted of IgM. Anti-LOS IgG levels in 5 immune sera before and after passage through anti-mouse IgM agarose were measured, and it was noted that absorption resulted in a mean decrease in IgG concentration of 13.6% (range 9.2-18.5%).

Serum bactericidal assays with IgM-depleted immune and adjuvant control sera performed using normal human serum (NHS) as the source of complement (FIG. 12B) showed that killing of gonococci mirrored anti-LOS IgG titers. Based on these data, GLA-SE was chosen as the lead adjuvant because it has received approval for human use.

Figure 2A:
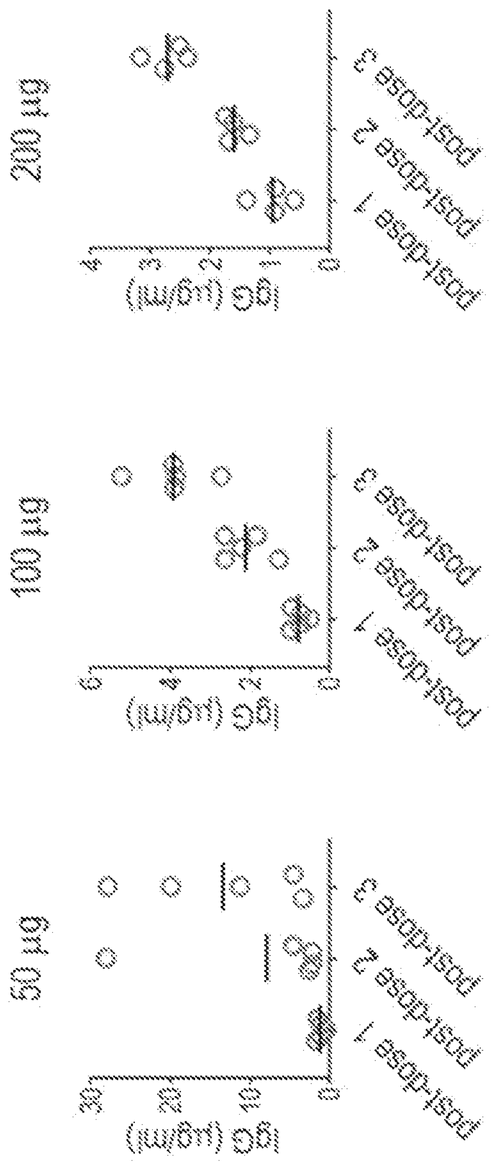
FIGS. 2A-2B show immunogenicity (FIG. 2A) of TMCP2/GLA-SE and functional activity of elicited antibodies (FIG. 2B). Six-week old female BALB/c mice were immunized with three doses of TMCP2 given at 50,100 or 200 μg per dose with GLA-SE adjuvant (5 μg) every 3 weeks, or with GLA-SE alone (adjuvant control). The groups immunized with 50 μg or 100 μg of TMCP2 per dose contained 5 mice each; the group given 200 μg/dose of TMCP2 had 4 mice.

Immunogenicity and Bactericidal Activity of Anti-Sera from Mice Immunized with TMCP2 and GLA-SE Adjuvant Immunization (initial inoculation plus boosting at 3 and 6 weeks [3 doses]) of mice with 50 μg (5 mice), 100 μg (5 mice), or 200 μg (4 mice) of TMCP2 combined with GLA-SE adjuvant. Immunization elicited anti-LOS IgG responses, measured two weeks after final boosting, that exceeded 2 μg/ml in every mouse (FIG. 2A). Responses in 3 of 5 mice given the 50 μg dose exceeded 10 μg/ml. The reasons for these high responses are not clear. Mice immunized with GLA-SE alone did not elicit detectable IgG responses against LOS. Specificity was demonstrated by non-reactivity of any of the sera with 15253 ΔlgtG LOS.

Figure 2B:
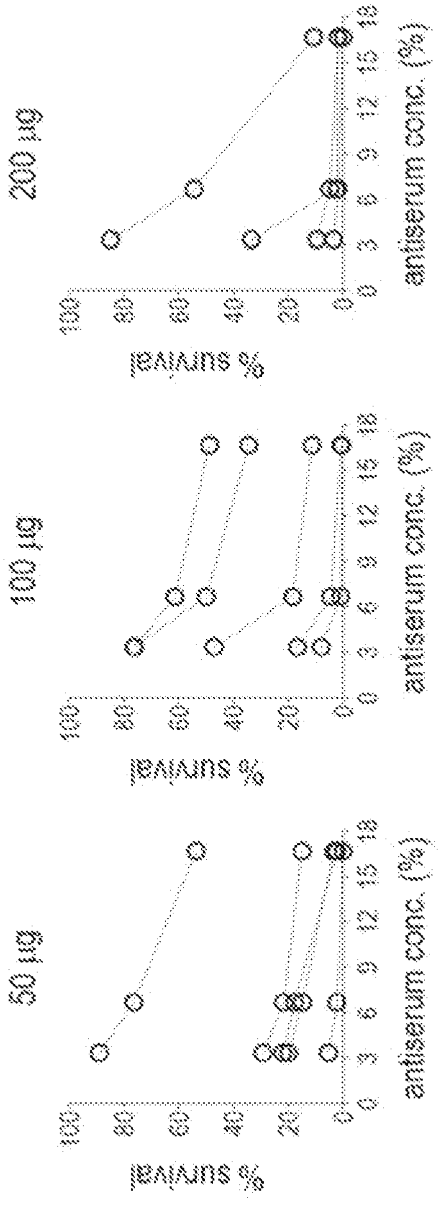

The 'natural' bactericidal IgM antibodies noted in naïve mice or mice given adjuvants alone seen in the adjuvant selection studies were not observed in subsequent experiments (performed after June 2018). Intact immune sera taken two weeks after the last immunization were tested for bactericidal activity against strain FA1090 (FIG. 2B; numerical data are shown in Table 3). All immune sera showed >50% killing when tested at a final dilution of 1:6 (immune serum concentration of 16.7%). Four of 5, 3 of 5, and 3 of 4 immune sera in the 50, 100, and 200 μg/dose groups, respectively, showed <50% survival (>50% killing) when immune serum was tested a concentration of 3.3% (1:30 dilution). Mice that received GLA-SE alone did not show IgG responses against LOS and did not support complement-dependent bactericidal activity of FA1090 (Table 4). Depleting IgM in these sera did not reduce bactericidal activity significantly (increase survival), indicating that IgG was responsible for the bactericidal activity in immune sera (Table 4).

During studies to develop TMCP2, it was noted that heat-inactivated sera from naïve mice or mice given adjuvant alone (control mice sera), depleted of endogenous complement, supported complement-dependent bactericidal activity against strains FA1090 and 15253 when normal human serum (NHS) was added; both strains are highly resistant to the bactericidal action of NHS alone. In addition, heat-inactivated (56° C. for 30 min) NHS added to control mouse sera failed to kill gonococci, suggesting that the observed killing was complement dependent. A systematic analysis of the bactericidal activity of heat-inactivated sera with added NHS from several strains of naïve mice from different sources was carried out (Table 1A-1H). Except for $Rag^{-/-}$ and JHD mice that both lack antibody, heat-inactivated sera from all other mice tested supported human complement-dependent killing of *N. gonorrhoeae*. Similarly, bactericidal activity was also supported by sera from CD1 mice housed at the Children's Hospital Oakland Research Institute, Oakland, CA given Alum adjuvant. Absorption of naïve or adjuvant control mouse sera against anti-mouse IgM agarose, but not protein A/G agarose (depletes IgG), abrogated bactericidal activity (survival >80%), revealing IgM as the antibody subclass responsible for the bactericidal activity. All mouse sera used in (human) complement-dependent bactericidal assays in this study have been depleted of IgM.

Post-dose 3 immune sera (IgM depleted) were tested for bactericidal activity against strain FA1090. Except for one serum sample in the group immunized with 50 μg of TMCP2/dose that showed 47% killing, all immune sera showed >50% killing when tested at a final dilution of 1:6 (immune serum concentration of 16.7%). Three of five immune sera in the 100 g/dose group and three of four immune sera in the 200 μg/dose group showed >50% killing at greater dilutions (1:30; 3.3% immune serum). Mice that received GLA-SE alone did not show IgG response against LOS and did not support bactericidal activity following IgM depletion.

In Vitro and In Vivo Efficacy of TMCP2 Tested at Various Doses

Three groups of female BALB/c mice (n=25 per group) were immunized with three doses of TMCP2 (50, 100, or 200 μg/dose, with GLA-SE adjuvant, 5 μg) given 3 weeks apart. A fourth group (n=25) received GLA-SE alone. Two weeks after the third immunization, mice in the diestrus phase of the estrous cycle were treated with PREMARIN® and challenged with *N. gonorrhoeae strain FA*1090 (n=6/group) or MS11 (n=6/group). Sera from mice not used for challenge (n=13 in each group) were collected by cardiac bleeding for immunologic studies (IgG LOS ELISA and serum bactericidal assays).

Figure 4A:
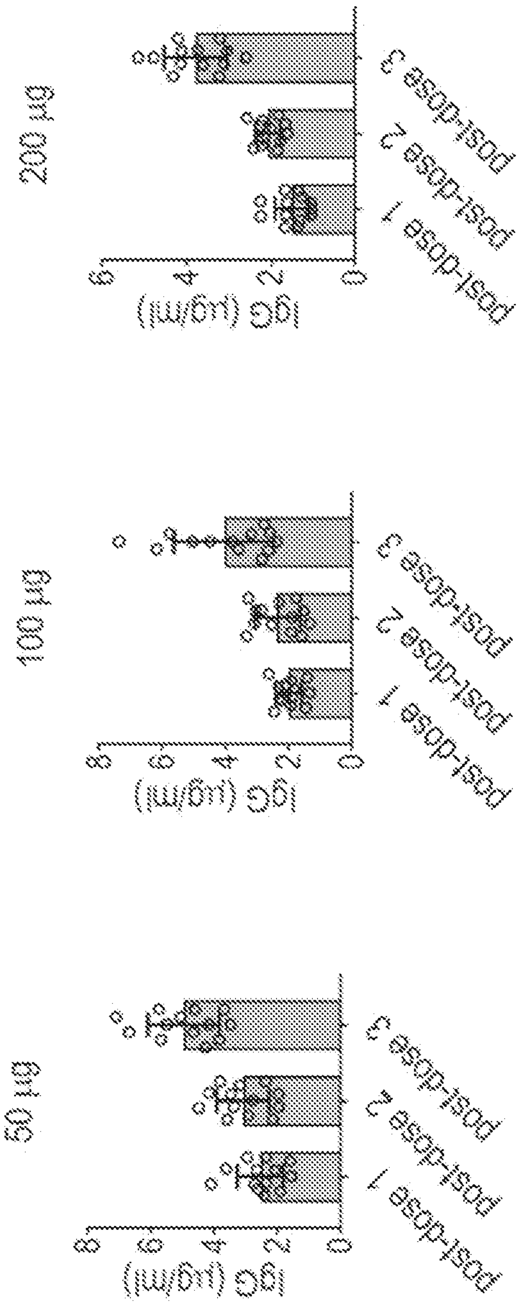
FIGS. 4A-4C show immunogenicity and functional activity of antibodies elicited in mice immunized with TMCP2/GLA-SE. Six-week-old female BALB/c mice were immunized with TMCP2 at doses of 50 μg, 100 μg, or 200 μg with GLA-SE adjuvant (5 μg), or with GLA-SE alone. Each group contained 13 mice and represented mice not used for challenge studies in FIG. 3.
Figure 13A:
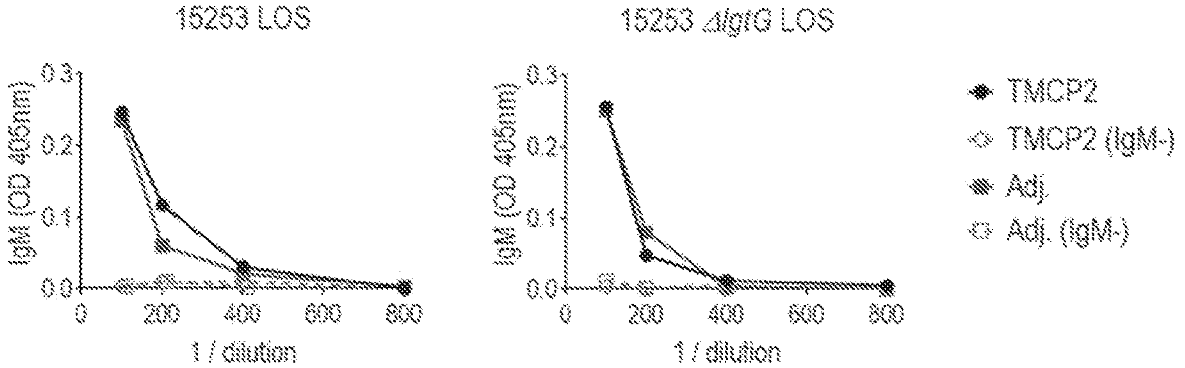
FIGS. 13A-13B show reactivity of IgM in immune and adjuvant control sera against LOS and FA1090. Post-dose 3 sera from mice (n=13) immunized with TMCP2 (50 μg/dose) plus GLA-SE were pooled (labeled 'TMCP2'); one aliquot was immunodepleted of IgM by passage over anti-mouse IgM agarose ('TMCP2 (IgM-)'). Similarly, an aliquot of pooled adjuvant control sera ('Adj.') was depleted of IgM ('Adj. (IgM-)'). The intact and IgM-depleted sera were tested for reactivity against LOS purified from strain 15253 (2C7-positive) or 15253 ΔlgtG (2C7-negative).
Figure 13B:
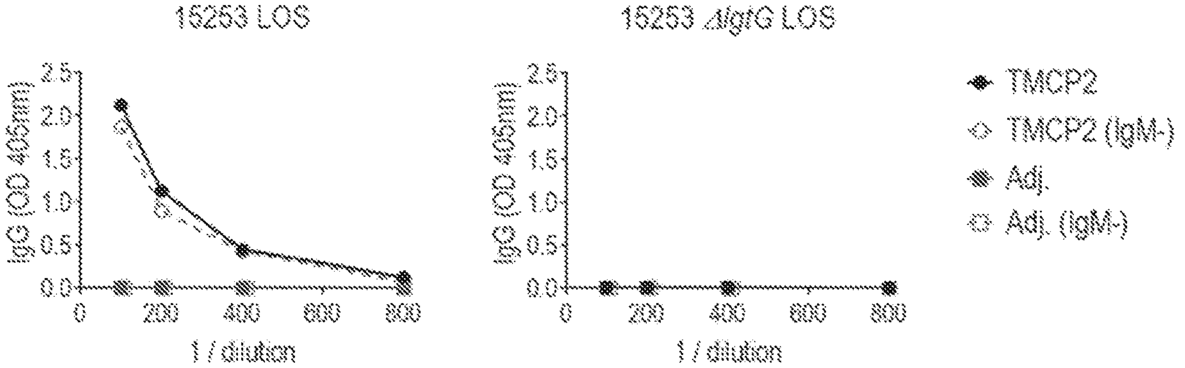
Figure 14:
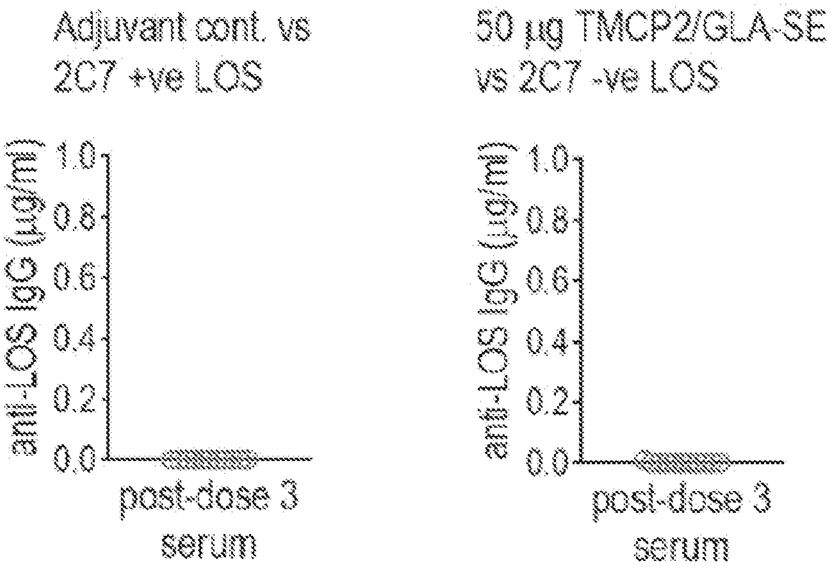
FIG. 14 shows specificity of IgG response to the 2C7 LOS epitope. Post-dose 3 sera from adjuvant (GLA-SE) control mice (experiment described in FIGS. 5A-5C) that were not infected with *N. gonorrhoeae* were tested for IgG reactivity with 2C7-positive LOS (left graph). Similarly, sera from TMP2/GLA-SE immunized mice not used for gonococcal challenge were tested for reactivity of IgG against 2C7-negative LOS derived from strain 15253 ΔlgtG.

Anti-LOS IgG levels were measured in immune sera (n=13 in each group) from mice not used for challenge experiments. As shown in FIG. 4A, anti-LOS IgG levels in intact immune sera exceeded 2 μg/ml in all mice. The mean anti-LOS IgG levels in the 50, 100, and 200 μg/dose groups were 4.98, 4.06 and 3.8 μg/ml, respectively. None of the sera from mice immunized with GLA-SE alone (adjuvant control) showed detectable anti-gonococcal LOS IgG levels. Anti-LOS IgM levels in pooled immune and pooled adjuvant sera were also measured (FIGS. 13A-13B). Similar IgM binding was measured to 15253 LOS (2C7-positive) and 15253 ΔlgtG LOS (2C7-negative) in immune sera and adjuvant sera indicating no apparent IgM response to the 2C7 epitope in mice (FIG. 13A). Predictably, passage of sera over anti-mouse IgM agarose abrogated IgM detection in both immune and adjuvant control sera. IgG binding to LOS in the same sera were also compared (FIG. 13B); only immune serum, but not adjuvant control serum bound 15253 LOS; no IgG binding to 15253 ΔlgtG LOS was detected.

Figure 4B:
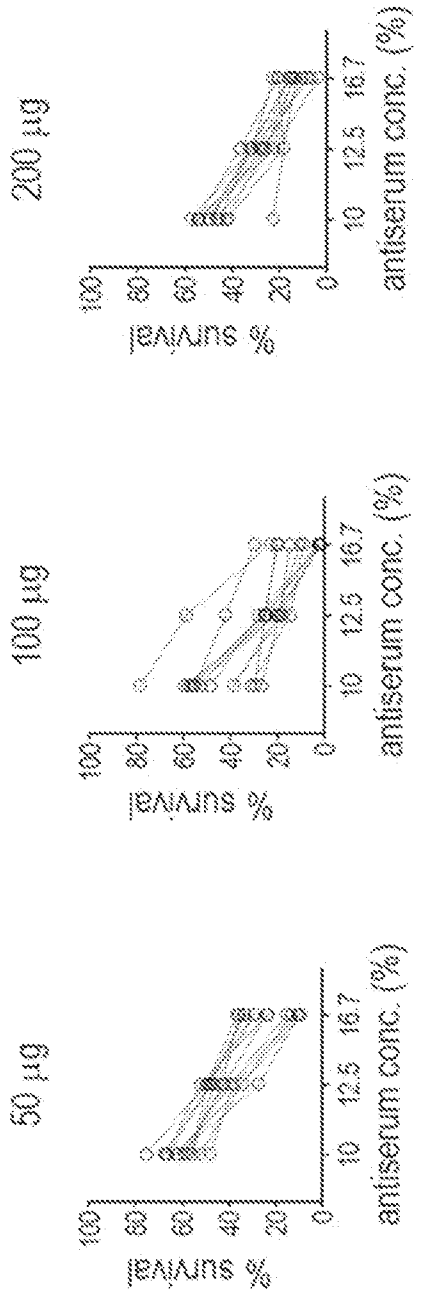
Figure 4C:
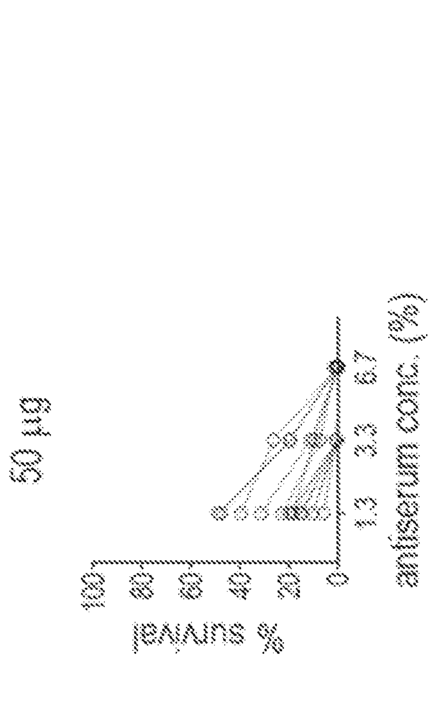

The 13 individual immune sera in each group collected after the $3^{rd}$ dose of TMCP2 were tested for ability to kill FA1090 and MS11 in complement-dependent serum bactericidal assays. Dose-dependent killing of *N. gonorrhoeae* was seen in all three groups. Notably, all sera in each group, when tested at a final concentration of 16.7% (1/6 dilution), resulted >50% complement-dependent killing (<50% survival) of FA1090 (FIG. 4B) and MS11. Strain MS11 was more susceptible than FA1090 to complement-dependent killing by sera from mice that had been immunized with a 50 μg/dose schedule. All 13 immune sera, when used at final concentrations of 3.3%, killed MS11, >60%; 6.7% immune serum concentrations resulted in >98% killing (FIG. 4C). Consistent with the observation that post-dose 3 sera did not possess specific IgM against the 2C7 epitope (FIGS. 13A-13B), significant decreases in killing of either FA1090 (Table 5) or MS11 (Table 6) when IgM was depleted were not noted. None of the antisera from adjuvant control (GLA-SE alone) mice showed any bactericidal activity (>100% survival; Table 5 and Table 6).

Figure 3A:
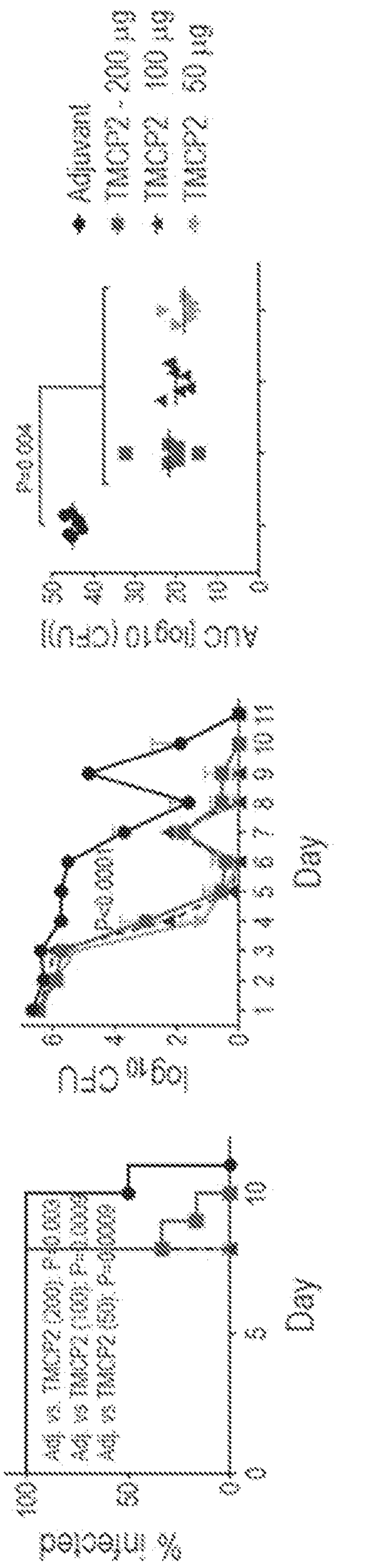
FIGS. 3A-3B show the efficacy of TMCP2/GLA-SE against *N. gonorrhoeae* strains FA1090 and MS11 in the mouse vaginal colonization model. Six week-old female BALB/c mice were immunized with TMCP2 (either 200 μg/dose, 100 μg/dose, or 50 μg/dose) plus GLA-SE (5 μg), or with GLA-SE alone (adjuvant control) at 0, 3, and 6 weeks. Two weeks after the last immunization, 12 mice in each group in the diestrus phase of the estrous cycle were treated with PREMARIN®; 6 mice in each of the four groups were infected intravaginally with strain FA1090 (5×107 CFU; n=6) or with strain MS11 (4.2×107 CFU) on day 0.
Figure 3B:
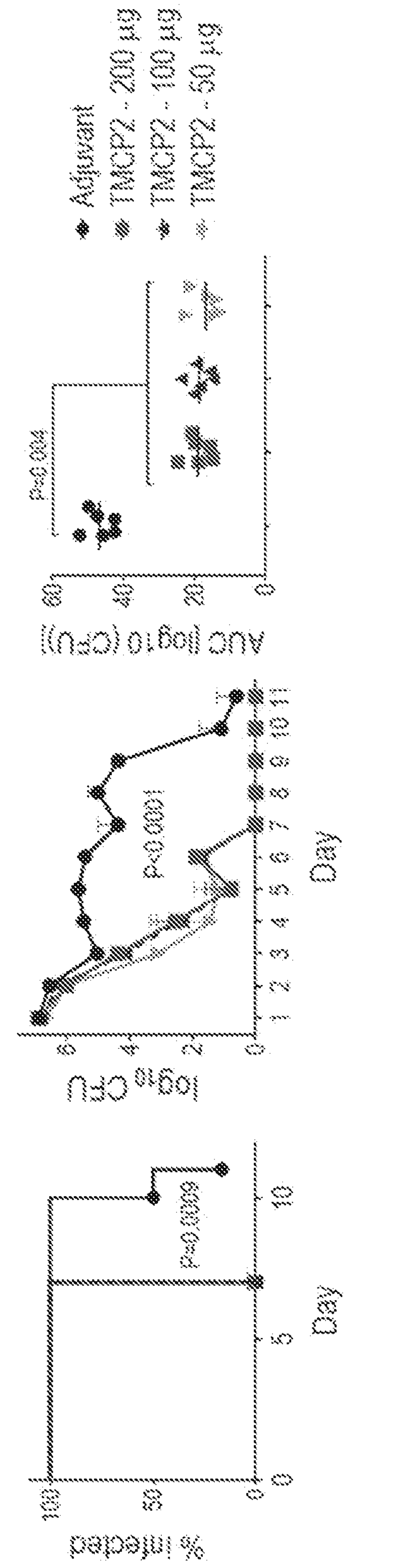

FIGS. 3A-3B show experimental challenge data with FA1090 and MS11, respectively, all three doses of TMCP2 accelerated clearance and diminished colonization with each of the gonococcal strains over the 11-day course of the experiments, compared to the adjuvant control. Mice challenged with FA1090 showed a transient 'reappearance' of bacteria on day 7 (MS11 'reappeared' on day 6); in the case of FA1090, reappearance of the organism resulted in delayed clearance compared to MS11 (Kaplan Meier curves; left graphs). The rate of decline of CFU with time (middle graphs) and the Area Under Curve analyses (right graphs) showed similar vaccine efficacy at all three doses and against both isolates.

Efficacy of TMCP2 Using a Biweekly Schedule

Figure 5A:
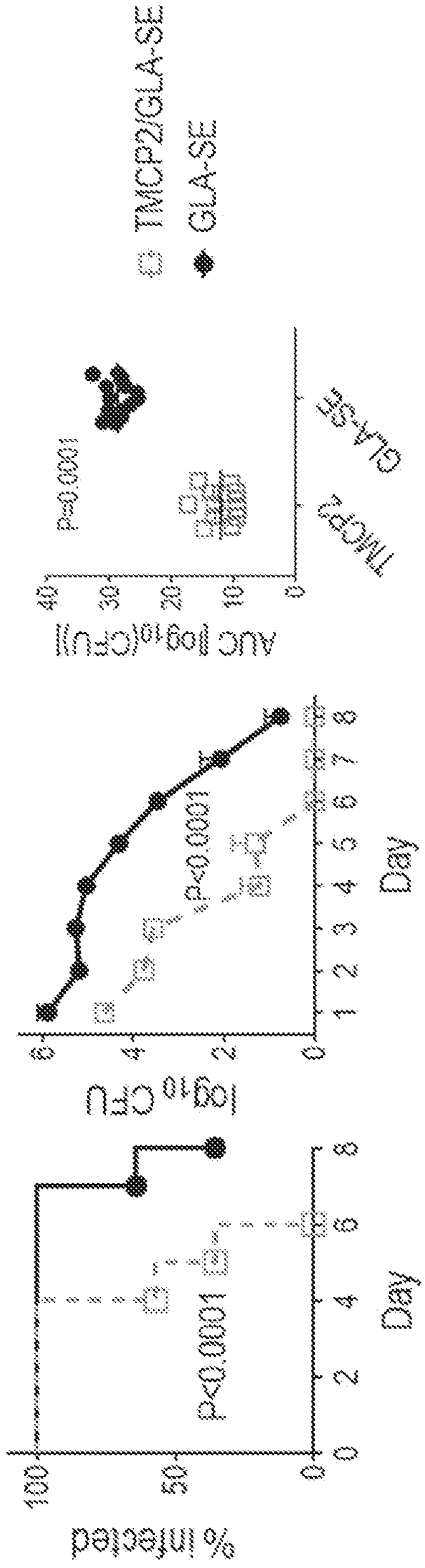
FIGS. 5A-5C show the efficacy of TMCP2/GLA-SE against *N. gonorrhoeae* FA1090 in the mouse vaginal colonization model using a biweekly 3-dose schedule. Six-week-old female BALB/c mice (n=25/group) were immunized with 50 μg/dose TMCP2 plus GLA-SE (5 μg), or with GLA-SE alone (adjuvant control) at 0, 2, and 4 weeks. Two weeks after the last immunization, 14 mice in each group in the diestrus phase of the estrous cycle were treated with PREMARIN® and infected intravaginally with strain FA1090 (107 CFU) on day 0. Serum from the remaining 11 mice in each group was collected by cardiac puncture for use in immunologic studies.
Figure 5B:
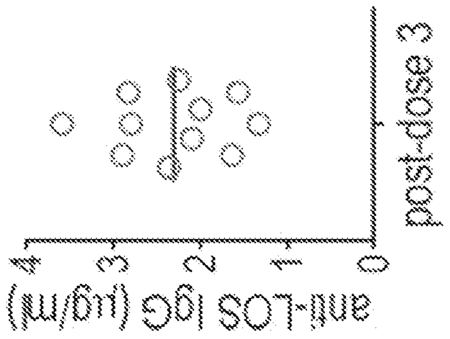
Figure 5C:
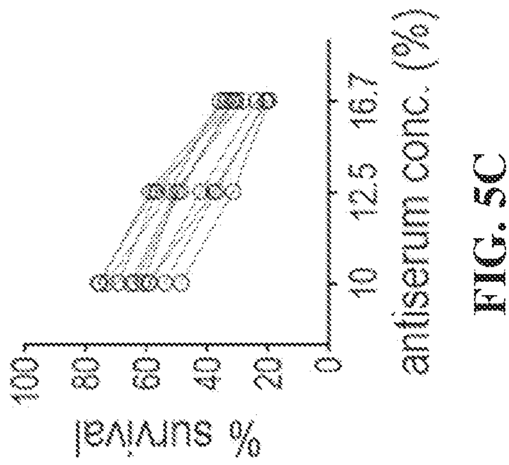

A more compressed schedule of immunization (dosing at 2 week instead of 3 week intervals) was also examined using the lower dose (50 μg of TMCP2), the latter as an approximation of the dose that might be used in human immunization. Mice were immunized with 50 μg of TMCP2 plus GLA-SE using 3, 50 μg doses, each given 2 weeks apart. Two weeks after the third dose, mice (n=14/group) were challenged with strain FA1090 (107 CFU). This immunization regimen also effectively attenuated gonococcal colonization (FIG. 5A). The mean anti-LOS level in the 11 immunized post-dose 3 immune sera obtained from non-infected mice was 2.31 μg/ml (standard deviation 0.68; range 1.33-3.59 μg/ml) (FIG. 5B). All sera showed bactericidal activity (>50% killing at 1:6 dilution [16.7% antiserum concentration]) (FIG. 5B) and similar to that achieved by similar/higher TMCP2 dosing and administration at longer intervals (FIGS. 3A-3B). Again, IgM depletion from sera did not significantly impact bactericidal activity (Table 7).

In a separate experiment, 5 mice were immunized with TMCP2 (50 g/dose) plus GLA-SE, or GLA-SE alone at 0, 2 and 4 weeks and collected serum and vaginal swabs 2 weeks after the third dose for measurement of anti-LOS IgG. Anti-LOS IgG was detected in vaginal swabs of all 5 mice given TMCP2 (Table 8).

DISCUSSION

A candidate gonococcal peptide vaccine, which elicits bactericidal antibodies against *N. gonorrhoeae*, significantly reduces the duration and burden of gonococcal cervicovaginal colonization in BALB/c mice. Combining TMCP2 with the Th1-biased adjuvant GLA-SE evoked 2C7 epitope-specific IgG antibody responses after immunization with three intramuscular doses. Studies in mice also suggest that a Th1 response clears infection and induces a memory response (35), which lends support to using Th1-inducing adjuvants for gonococcal vaccines.

A limitation of an octameric peptide vaccine used in a previous study (13) was heterogeneity of the molecular mass of the preparation, likely the result of formation of inter- and intramolecular disulfide bonds. To circumvent this problem, a novel synthetic method in which each peptide subunit was first circularized with a covalent, non-reducible thioether bond was devised; each of the circularized subunits was then linked to a dendrimeric Glu backbone. Attempts to synthesize an octameric peptide using this method were technically challenging; instead, a tetrapeptide multiple antigenic peptide was synthesized for evaluation. The resulting compound, TMCP2, showed a single peak on mass spectroscopy. This relatively facile synthesis process yielded a compound of greater than 95% purity, which is suitable for scale-up and production of an inexpensive gonococcal vaccine candidate.

Activation of the classical pathway of complement requires engagement of the C1 complex (subunits of C1q, C1r and C1s), triggered by Fe antibody domains. Upon binding to surfaces, Fc domains of proximate IgG molecules form ordered hexamers through non-covalent interactions (29), which then simultaneously engage multiple globular heads of C1q, also a hexameric molecule. Multimeric interactions between globular domains of C1q and Fc convert otherwise low-affinity monomeric IgG Fc-C1q associations to interactions of high avidity, which permits autocatalysis of C1r and further complement activation. An effective bactericidal antibody requires a critical density of surface targets to engage C1q and permit complement activation. On a molar basis, LOS is the most abundant gonococcal outer membrane molecule and serves as a convenient target for binding of closely spaced antibody molecules whose Fc domains can then readily engage the C1 complex an activate complement. It has been shown that an intact complement system is necessary and sufficient for efficacy of passively administered bactericidal mAb 2C7—given either systemically or intravaginally—in the mouse vaginal colonization model (58). The importance of complement in host defenses against gonorrhea, is highlighted by the observation that both congenital and acquired defects of individual terminal components of complement are associated with an increased incidence of disseminated gonococcal infection (DGI) (30-33). Based the data with mAb 2C7, it is proposed that attenuation of colonization by antibodies elicited by TMCP2 vaccine also occurs via complement-dependent bactericidal antibody activity. A vaccine candidate that comprises gonococcal outer membrane vesicles plus microencapsulated IL-12 given intravaginally requires B cell activity, presumably to produce antibodies (34), however, a requirement for complement has not been shown.

Similar to the research findings, no other gonococcal vaccine candidates tested in the cervicovaginal colonization model in estradiol-treated mice show sterilizing immunity (34, 35, 36). Immunomodulatory effects of estrogen (37) may curb immune defenses that are important to clear *N. gonorrhoeae*. Seminal studies over 50 years ago (38) showed that the activity of terminal complement components in male mice exceeds, by 8- to10-fold, activity in female mice. Administration of testosterone increases complement activity; estrogen has the opposite effect (39). Therefore, a vaccine antibody response that utilizes terminal complement to act in concert with the bactericidal action of antibody may also require waning of the suppressive effects of estrogen on terminal complement components before full bactericidal activity is restored.

A retrospective epidemiologic analysis showed that a detergent extracted meningococcal outer membrane vesicle (dOMV) vaccine called MeNZB designed and implemented in a widespread vaccination program to control an epidemic of group B meningococcal disease in New Zealand, showed diminished coverage in populations subsequently infected with *N. gonorrhoeae*—calculated as 31% effectiveness of MenZB in decreasing gonococcal infection—reduced to 14% in populations co-infected with *N. gonorrhoeae* and *Chlamydia*, a frequent clinical occurrence (40-42). Meningococci and gonococci share several similarities and it is possible that one or more proteins in MeNZB that cross-react with *N. gonorrhoeae* may elicit protective immune responses. Individuals administered a licensed group B meningococcal vaccine, Bexsero®, which contains 5 recombinant meningococcal protein antigens in addition to the same dOMV that constitutes MeNZB (43), elicit antibodies, immunochemically, that cross-react with *N. gonorrhoeae* (44). Antibodies elicited by immunizing mice with Bexsero® or MeNZB were reported to support bactericidal activity against *N. gonorrhoeae* (59). However, a separate study did not reveal bactericidal antibody activity against *N. gonorrhoeae* FA1090 in immune sera from individuals vaccinated with Bexsero® (28). How MeNZB provides protection against gonorrhea remains unclear; possible mechanisms may include reduction of adhesion of Ng to human cervical cells, as demonstrated with murine antibodies elicited by Bexsero® or MeNZB (59). Currently, several gonococcal vaccine candidates are undergoing pre-clinical evaluation (reviewed in Ref. (5)), some of which elicit bactericidal activity (45-47). Knowledge of the immune defenses responsible for clearing gonococcal infection is an important aspect of developing effective vaccines against this disease.

Three glycosyltransferase genes—lgtA, lgtC, lgtD—involved in LOS biosynthesis are phase-variable because of slipped-strand mispairing of homopolymeric poly-G tracts in their open reading frames (48, 49); a fourth, lgtG, containing a poly-C tract is also phase variable (12, 50-53). Expression of the 2C7 epitope requires lgtG to be phase-varied 'on'; expression status of the three other lgt genes modulate binding of mAb 2C7 to LOS (11). As discussed above, the 2C7 LOS epitope is expressed almost universally in vivo and by minimally passaged isolates. The 2C7 epitope was identified in 64 of 68 (94%) gonococcal isolates examined directly in cervical secretions from women in a sexually transmitted disease clinic in Boston in the early 1990s and 96 of 101 (95%) of randomly chosen minimally (second-passage) isolates (7). Recently, it was reported that 100% of 75 minimally passaged isolates from China also expressed the 2C7 epitope (16). Importantly, mAb 2C7 was bactericidal (>50% killing) against each (100%) of the 62 isolates tested in complement-dependent bactericidal assays, including strains that expressed low levels of the epitope (13). Because LOS is the most abundant outer membrane molecule on gonococci, expression of the 2C7 epitope on even a small fraction of LOS may permit binding of antibody at a density sufficient to engage the C1 complex and activate the classical pathway. It is speculated that widespread expression of this epitope results from gonococci's ability to sialylate lactose expressed from HepII, which facilitates engagement of Siglec receptors (17). Many Siglec receptors signal through their immunoreceptor tyrosine-based inhibitory motif (ITIM) tails (54) to dampen host inflammatory responses that otherwise sense invading pathogens (55, 56). Neu5Ac (sialic acid) that caps lactose from HepII also inhibits complement C3 deposition on the bacterial surface (16). Genetic deletion of lgtG or 1st (sialyltransferase) from a strain whose only site for sialylation is the terminal Gal of HepII lactose markedly attenuates the ability of *N. gonorrhoeae* to colonize the vagina of estradiol-treated mice (13, 16). Additional evidence for the importance of lgtG expression was provided by Lam and Gray-Owen, who showed that serial passage of *N. gonorrhoeae* in mice was accompanied by increased fitness of bacteria with each generation—i.e., an increasing fraction of mice could be infected with bacteria recovered from each successive mouse passage. Intriguingly, there was a reproducible positive selection for gonococcal variants with lgtG 'on' (57). Resistance to antibodies elicited by a '2C7 vaccine' would require lgtG to be turned completely 'off'. Based on the accumulated evidence from: studies of minimally passaged isolates; bacteria examined directly ex vivo from humans (without passage on media) and studies in mice—as discussed above, it is proposed that mutations in gonococci that eliminate 2C7 LOS epitope would render the organism less fit and avirulent. From a public health perspective, translation to a decrease in burden and duration of infection can have profound effects on disease pathology and transmission. In conclusion, TMCP2 represents an important step forward in the development of a safe, economical and effective gonococcal vaccine, or subcomponent thereof.

Peptide Constructs Prior to Derivation of the Lead Candidate (Numbers in Brackets Refer to Compounds Listed in Table 2 that Indicate Chemical Structures Screened for Use in this Study)

The Tetra-MAP preparation (termed Tetra MAP 1 [1]; and an Octa-MAP preparation (termed Octa MAP1 [2]) that had been used in a previous immunization/challenge study (—challenge performed with Octa-MAP 1 only) (Gulati S, Zheng B, Reed G W, Su X, Cox A D, St Michael F, Stupak J, Lewis L A, Ram S, Rice P A. 2013. PLoS Pathog 9: e1003559) was synthesized by 'step-wise' addition of amino acids to a poly-lysine core. This resulted in a heterogenous preparation (Table 1A; western blot showed for the Octa-MAP preparation only) that while effective in immunization/challenge studies, was not suitable for further clinical development.

Figure 18:
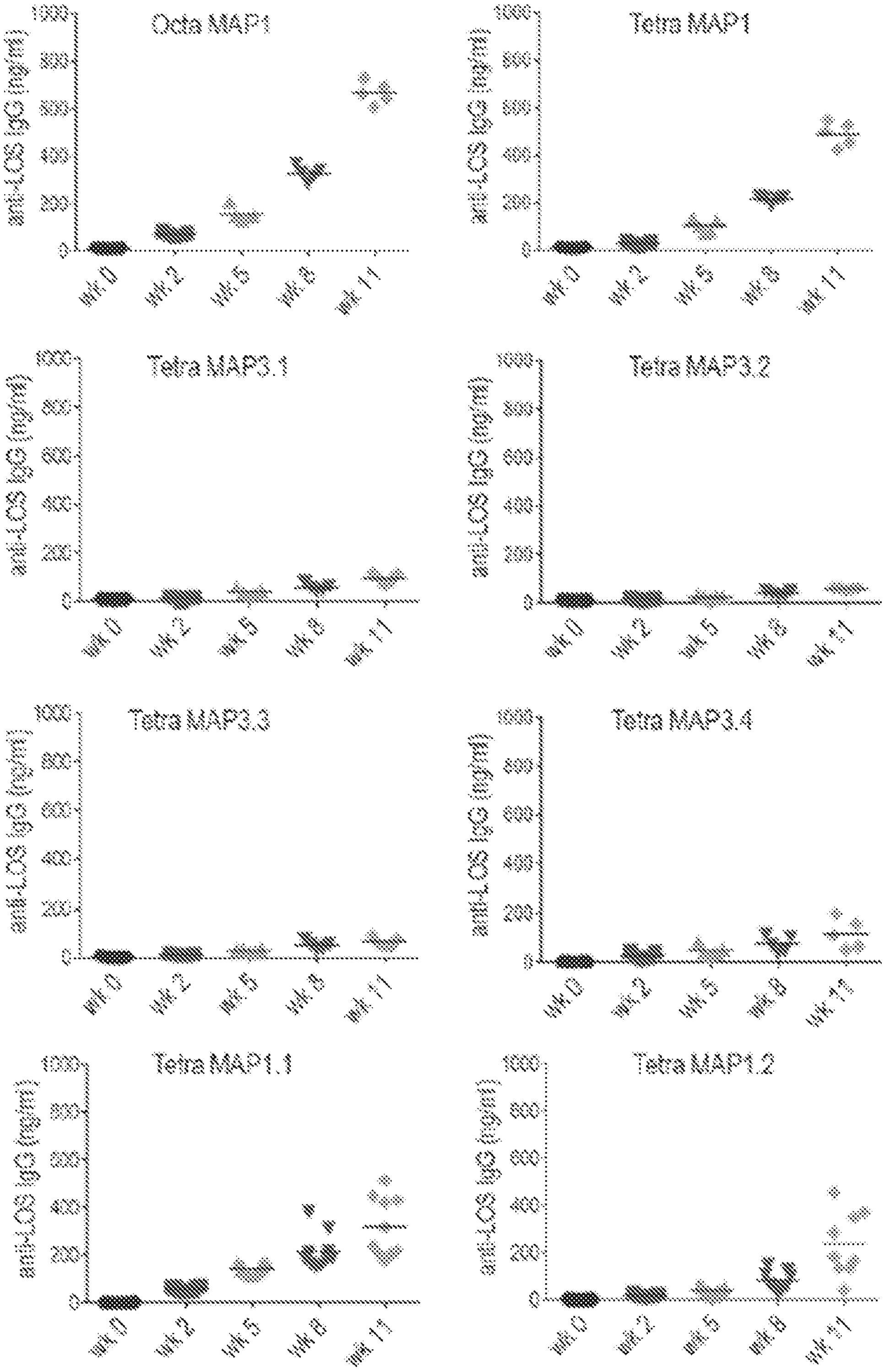
FIG. 18 shows immunization studies of original stepwise synthesized antigens Octa-MAP and Tetra-MAP, MOD3 derivatives for immunization, and Tetra MAP 1.1 and Tetra MAP 1.2 (n=9 mice/group). TetraMAP1.1 (bottom row; (identical structure to original Tetra-MAP1, but made by modular synthesis; structure: (CGPIPVLDENGLF APGPC)$_4$(Lys)$_2$Lys-β-Ala-COOH)) elicited similar anti-LOS Ab levels as Tetra MAP1 (top row). Mod3 (circularized peptide KIPVLDENGLFAP-PEG$_2$-KK (SEQ ID NO: 3)) was linked to different core structures to yield tetraMAP 3.1 ((KIPVLDENGLFAP-PEG$_2$-KK)$_4$-MAP$_4$), tetraMAP 3.2 ((KIPVLDENGLFAP-PEG$_2$-KKC)$_4$-Maleimide$_4$-MAP$_4$), tetraMAP 3.3 (KIPVLDENGLFAP-D Lys-D Lys$_4$-K$_2$-K-MAP$_4$) and tetraMAP 3.4 (KIPVLDENGLFAPGPC-D Lys-D Lys$_4$-K$_2$-K-MAP$_4$). Immunogenicity was evaluated in BALB/c mice (n=5 mice/group). IgG against 2C7+LOS was measured by ELISA. Original Octa MAP1 and Tetra-MAP1 compounds were included as historical (positive) controls.

To overcome heterogeneity of the immunogen, all further attempts used a 'modular' synthesis approach, where highly purified (and cyclized where indicated) peptides were added 'en bloc' to the core. Synthesis of Tetra-MAP (termed Tetra MAP 1.1 [3]) using the 'modular' approach and the original core yielded the same compound as the 'step-wise' prepared material. A 2nd compound that substituted serine for Cys at the N-terminal Cys residue (termed Tetra MAP 1.2 [4]) to reduce internal disulfide formation was also produced. Neither compound was superior to 'step-wise' produced material in immunogenicity studies (shown below in FIG. 18).

Construction of a Tetra-MAP was attempted utilizing 4 maleimide (MAL) residues from a Lys dendrimer core (Table1B) that would link sulfydryl groups (—SH) of the N-terminal cysteine directly to the (poly) lysine core. However, additional reaction of the maleimide residues with primary amines in the monomeric peptide in this reaction resulted in a product that was poorly soluble and highly heterogeneous; this approach was also abandoned.

Figure 16:
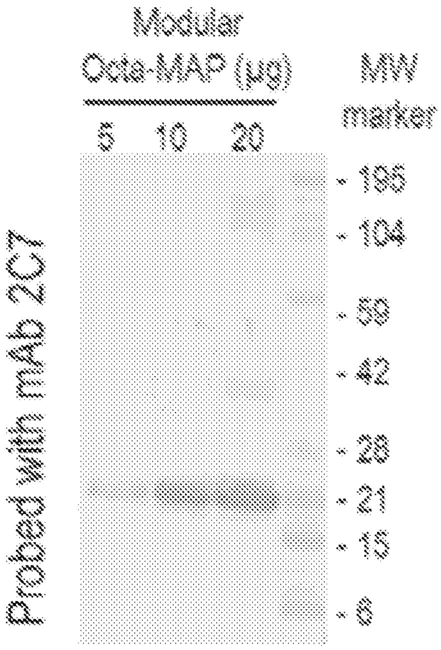
FIG. 16 shows western blot analysis of Modular Octa-MAP product.

In experiments to modify linkages of the monomeric peptide mimitope (PEP1) to the core, an Octa-MAP was made by first protecting the N-terminal Cys of the mimitope (PEP1) with a tert-butylsulfinyl (StBu) group [5] or replacing the N-terminal Cys with serine [6] and then linking the C-terminal Cys of the monomeric peptide to a heterobifunctional cross-linker intermediary molecule (MAL-PEG4-NHS), through the maleimide (MAL) reactive group (Table 1C). The reactive N-hydrosuccinimide (NHS) at the N-terminus was displaced and PEP1-MAL-PEG4 molecules were amide-linked to each of 8 Lys residues of a Poly-Lys backbone. Polyethylene glycol (PEG4) was included to ensure a water-soluble product. Unfortunately, this synthetic process, although yielding a homogenous compound (FIG. 16), was too inefficient and expensive for production and scale-up.

In order to eliminate heterogeneity, three processes were considered to modify the monomeric peptides: (i) elimination or replacement of terminal cysteines, (ii) use of Click chemistry as means to link peptide to the core and (iii) use of Reverse MAP synthesis (Reverse MAP entails positioning carboxyl groups in the core for modification by amine components from the peptide monomers) to link several versions of the initial peptides in stable cyclic forms using either disulfide or thioether bonds resulting in stable cyclic peptides that would be easier to purify, simplify chemical synthesis and increase the yield of the multiantigenic peptide (MAP).

Figure 17:
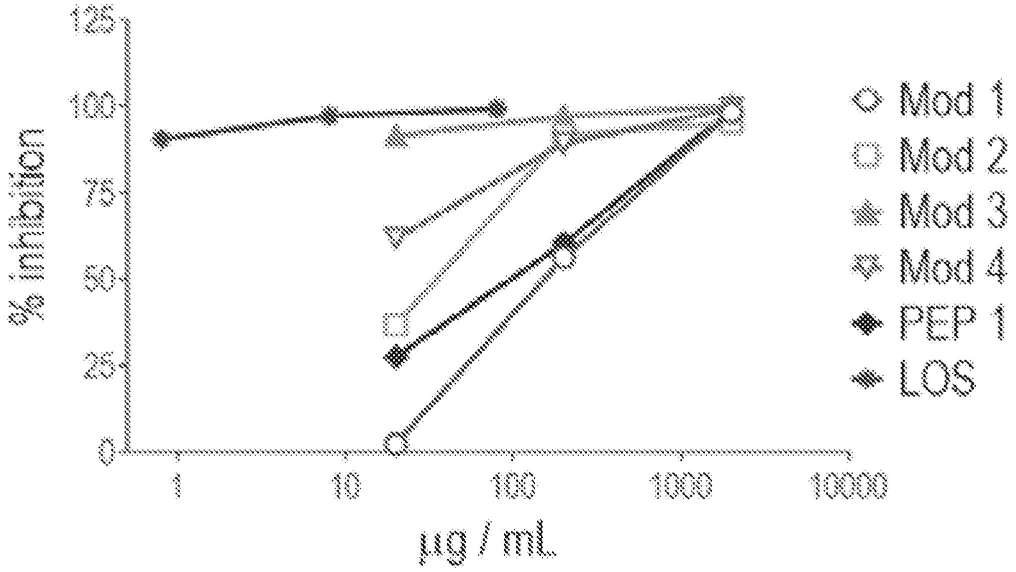
FIG. 17 shows circular monomeric peptides tested for their ability to inhibit mAb 2C7 binding to LOS in order to down-select for further tetra-MAP synthesis. PEP1 is the original mimitope peptide monomer. Mod3 showed the best ability to inhibit mAb 2C7 binding to LOS (inhibition ELISA assay described in methods) and was chosen to generate tetra-MAP derivates 3.1, 3.2, 3.3 and 4.4.

In the first process, PEP1 preparations were modified at the termini, also to eliminate Cys (labeled Mod 1 [7], Mod 2 [8], Mod 3 [9] and Mod 4 [10][Table 1D and FIG. 17]) and tested for comparative antigenicity using mAb 2C7 as the probe. Mod 3, the most antigenic, was used to make 4 different Tetra-MAP derivatives (Tetra MAP 3.1 [11], TetraMAP 3.2 [12], TetraMAP 3.3 [13] and TetraMAP 3.4 [14]) (Table 1E) each of which, used singly, was poorly immunogenic in BALB/c mice (FIG. 18; TetraMAP 1.1 [3] and TetraMAP 1.2 [4] were also tested for immunogenicity). Two linear concatemers of Mod 3, containing 2 copies of the nominal peptide using different length spacers were also non-immunogenic (Table 1H, [15] and [16]).

Figure 20A:
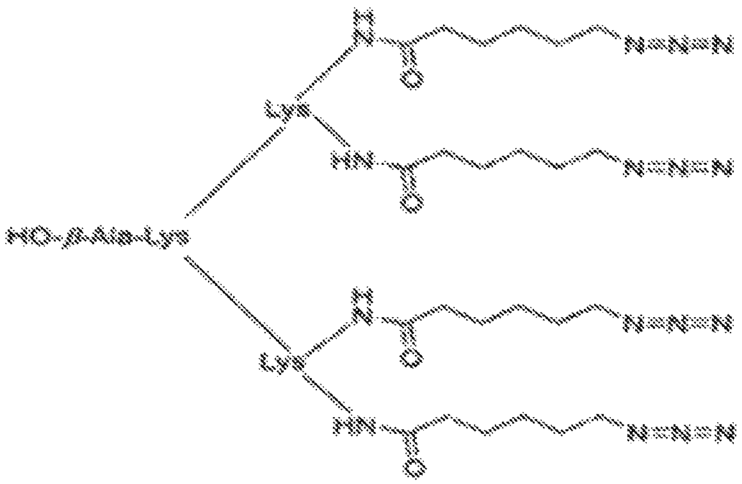
FIGS. 20A-20B show structure of Core synthesized for Click chemistry linkage.

A second approach to conjugate the peptide mimitope (cyclic) to the core using Click chemistry (copper-catalyzed reaction of an azide with an alkyne to form a 5-membered heteroatom ring) was then used. Several cyclic monomeric mimotope peptides were constructed (Click pep #1 through Click pep #4; Table 1G and [17] and [18]) and used in the Click chemistry approach to couple them to Click Core 4 (Table 1G and FIGS. 20A-20B) but this approach yielded low amounts of product with excess residual substrate (FIGS. 20A-20B; [17] and [18]); this approach was therefore abandoned.

Figure 9:
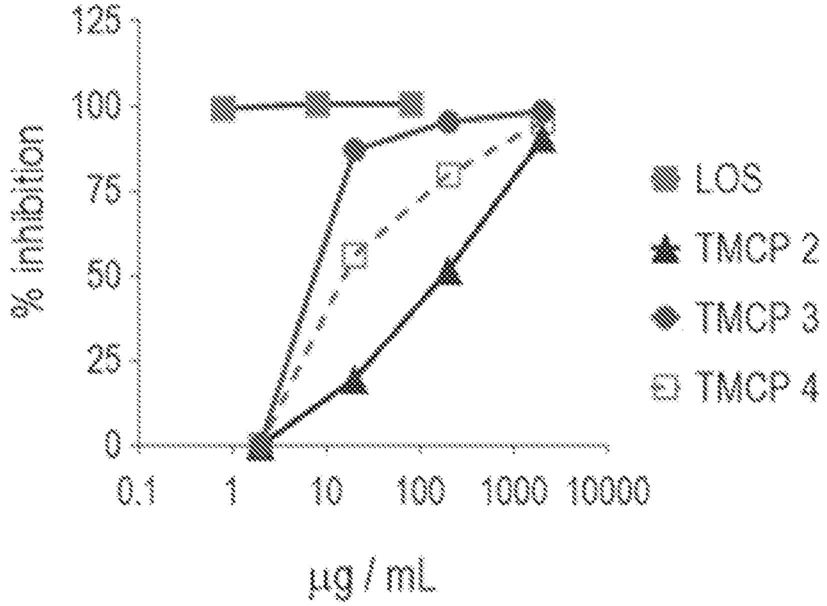
FIG. 9 shows inhibition of mAb 2C7 binding to solid phase-affixed (coated) gonococcal LOS by: TMCP2, TMCP3, TMCP4 (see Table 1K for description of peptides) and nominal LOS (control). mAb 2C7 (0.04 μg/ml) was added to microtiter wells coated with LOS purified from gonococcal strain 15253 in the presence of increasing concentrations of CP2, TMCP2 or LOS (positive control for 100% inhibition). The Y-axis shows the % inhibition of mAb 2C7 binding (residual binding) to immobilized LOS in the presence of the peptide (TMCP2 or CP2) or soluble LOS relative to binding of mAb 2C7 alone to immobilized LOS.
Figure 10:
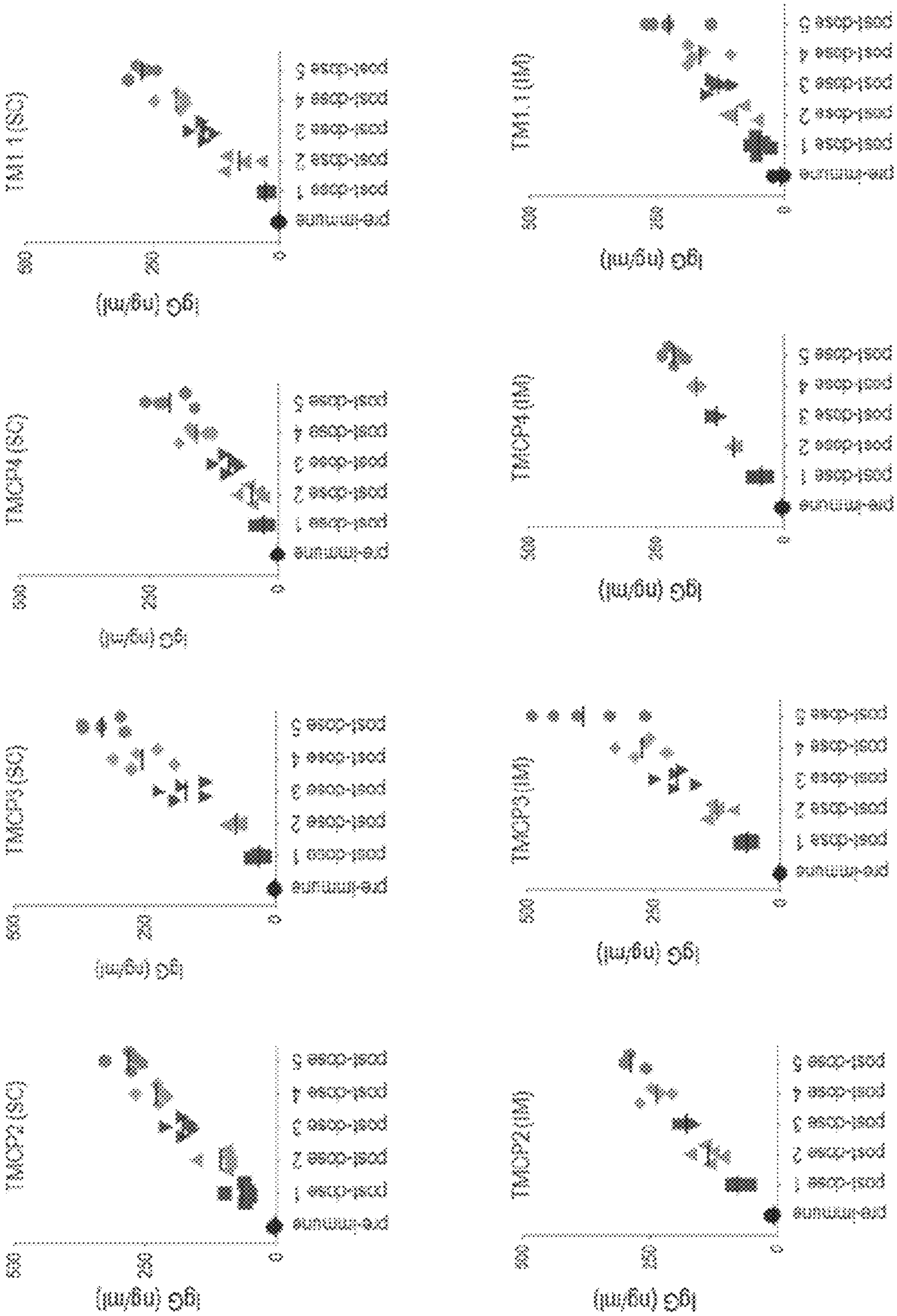
FIG. 10 shows anti-LOS antibody elicited by immunization of BALB/c mice with TMCP2, TMCP 3 and TMCP4 (see Tables 1A-1K for description of peptides). Antibodies elicited against LOS purified from *N. gonorrhoeae* strain 15253 (2C7-positive) in mice (n=5/group) immunized with tetra-MAP vaccine candidates TMCP2, TMCP3 and TMCP4 (50 μg/dose at weeks 0, 3, 6, 9, and 12) and Sigma MPL adjuvant given via the subcutaneous (SC) or intramuscular (IM) routes were measured by ELISA. A similar immunization schedule had been used previously with Octa-MAP1 (13) and was undertaken to permit development of maximal antibody titers. Tetra-MAP1.1 has the same peptide sequence and poly-lysine core ((Lys)2Lys-P-Ala-COOH) described previously (19) and was used as a control. Sera collected from each mouse at weeks 0 (pre-immune), 2 (post-dose 1), 5 (post-dose 2), 8 (post-dose 3), 11 (post-dose 4), and 14 (post-dose 5) were tested for reactivity with 15253 LOS.
Figure 11:
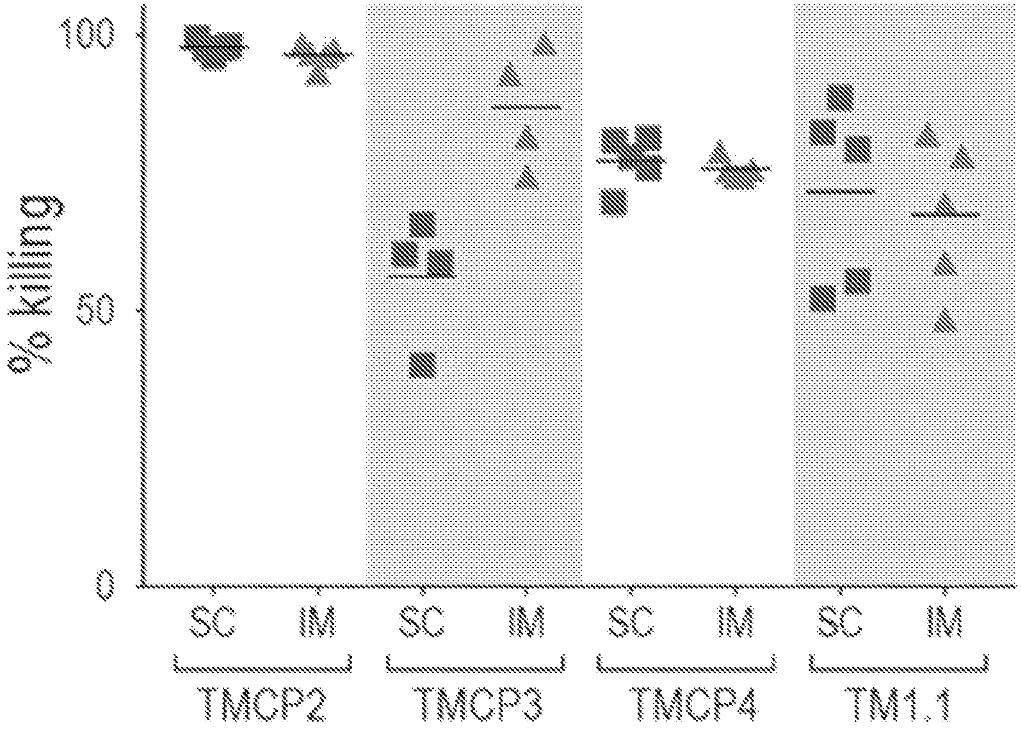
FIG. 11 shows serum bactericidal activity (SBA) of mouse antisera raised against tetra-MAP vaccine candidates (50 μg/dose at weeks 0, 3, 6, 9, and 12) with Sigma MPL adjuvant given via the subcutaneous (SC) or intramuscular (IM) routes (see FIG. 10 for immunization details). See Tables 1A-1K for a description of peptides. Post-dose 5 mouse anti-serum (IgM depleted) was tested against *N. gonorrhoeae* strain 15253 at a final dilution of 1:3 in the presence of 17% normal human serum (NHS) as the complement source. Y-axis, % killing ([CFU at t0–CFU at t30/CFU at t0]×100).

Finally, use of a reverse MAP core, where conjugation of monomers ([19], [20] and [21]) were carried out through the C-terminus of the core structure. One of the preparations, Tetra-MAP Cyclic Peptide 2 (TMCP2) [22], was modified at the N-terminus of the monomeric peptide (PEP1) so a stable non-reducible (covalent) thioether bond formed a cyclized peptide with the C-terminal Cys of the peptide (Table 1H). The two other peptides, TMCP3 [23] and TMCP4, [24] each contained internal disulfide bonds when cyclized leading, potentially, to the formation of heterogenous molecules (Table1H). TMCP3 bound best to mAb 2C7 as determined by inhibition ELISA (FIG. 9). TMCP2 and TMCP3 yielded higher anti-LOS titers than TMCP4 in immunization experiments that used the tetrapeptides plus Sigma MPL adjuvant (FIG. 10). Anti-TMCP2 antisera showed maximal complement-dependent bactericidal activity against *N. gonorrhoeae* strain 15253 in immunized mice (FIG. 11) and was chosen for further development. It is worth noting that affinity of binding to mAb 2C7 did not correlate with the functional antibody response. In light of its stability and performance in functional studies, TMCP2 was chosen as the lead candidate and was characterized further.

Tables

Tables 1A-1H. Summary of Peptides Synthesized and Tested

TABLE 1A

| Original Tetra- and Octa-MAP Constructs | |
|---|---|
| Monomeric mimitope sequence (PEP1):<br>CGP**<u>IPVLDENGLFAP</u>**GPC (SEQ ID NO: 8)<br>(aa's in bold and underlined font) indicates the consensus sequence derived from a peptide display library; N- and C-terminal CGP and GPC, respectively, were retained from the FliC scaffold in the<br>pFliTrx ™ system, to facilitate circularization, if needed (Ngampasutadol J et al. Vaccine. 2006.24(2): 157-170; Gulati S et al. PLoS Pathog. 2013.9(8): e11003559) | 'Stepwise' addition of amino acids to polylysine core. The resulting product was too heterogenous for clinical development (Octa MAP 1 product shown in FIG. 15) and was abandoned. |
| Tetra MAP1<br>(CGP**<u>IPVLDENGLFAP</u>**GPC)4(Lys)2Lys-β-Ala-COOH<br>Octa MAP 1<br>(CGP**<u>IPVLDENGLFAP</u>**GPC)8(Lys)4(Lys)2Lys-β-Ala-COOH | |

TABLE 1B

| Tetra-MAP linked to Poly-Lys-maleamide core | |
|---|---|
| Peptide: Ac-(CGP**IPVLDENGLFAP**GPC (SEQ ID NO: 8))-Lys-OH Cys residues linked by disulfide Core: β-Ala-Lys-(Lys)2-(Mal)4 | The product was too heterogeneous and this approach was abandoned. |

TABLE 1C

| Modular addition of mimitope PEP1 to poly-Lysine core | |
|---|---|
| Octa-MAP1-modular [H2N-Cys(StBu)GP**IPVLDENGLFAP** GP(CysMAL-PEG4)-amide]$_8$(Lys$_7$MAP)(bA)-amide | Mimitope (PEP1) added 'en bloc' to poly-lysine core A modular system approach where each 18 aa single peptide (PEP1) was synthesized first and then purified to homogeneity. The N-terminal Cys was protected with a tert-butylsulfinyl (StBu) group; —SH of the C-terminal cysteine was linked to a heterobifunctional cross-linker intermediary molecule (MAL-PEG4-NHS), through the maleimide (MAL) reactive group at one end. By displacing the reactive N-hydrosuccinimide (NHS) on the other end, PEP1-MAL-PEG molecules were amide-linked to each of 8 Lys residues of the Poly-Lys backbone. PEG4 was included to create a water-soluble product. After synthesis and purification, the final octa-MAP product is treated with 0.5M tris-(2-carboxyethyl)phosphine hydrochloride to remove StBu from the N-terminal cysteine. This octa-MAP (~20.3 kDa) contained >90% complete octa-MAP. The process was too inefficient (low yield) for scale-up production of an economical vaccine product and therefore abandoned. |

Tables 1D.-1H. TetraMAPs without Terminal Cys Residues

TABLE 1D

| Monomeric (circularized) peptides used for construction of tetra-MAPs (using modular approach) | |
|---|---|
| Mod1: SGP**IPVLDENGLFAP**GPS (SEQ ID NO: 9)<br>Mod2: **IPVLDENGLFAP** (SEQ ID NO: 2)-PEG2-KK<br>Mod3: K**IPVLDENGLFAP** (SEQ ID NO: 3)-PEG2-KK<br>Mod4: SGP**IPVLDENGLFAP** (SEQ ID NO: 11)-PEG2-KK | This set of peptides (PEP1s) was constructed without terminal Cys residues because: 1) the oxidation state of the Cys residues was uncertain-i.e., it was not clear if all peptides were in a given state (monomers, linear, cyclic) with respect to the sulfhydryl groups and 2) the tetra-MAP construction (reviewed above) had utilized 4 maleamide residues from a Lys dendrimer core that reacted both with primary amines and sulfhydryl groups. These factors likely contributed to product heterogeneity of the original Octa- and Tetra-MAPs<br>The circular monomeric peptides were tested for their ability to inhibit mAb 2C7 binding to LOS in order to down-select for further tetra-MAP synthesis. PEP1 is the original mimitope peptide monomer. Mod3 showed the best ability to inhibit mAb 2C7 binding to LOS (inhibition ELISA assay described in methods) and was chosen to generate tetra-MAP derivates 3.1, 3.2, 3.3 and 4.4<br>(described in Table 1E) |

TABLE 1E

| Tetra-MAP derivatives of Mod3 (dendrimers) | |
|---|---|
| TetraMAP3.1<br>(K**IPVLDENGLFAP**-PEG2-KK)4-MAP4<br>TetraMAP3.2 | Mod3 was linked to different core structures as described on the left. Immunogenicity was evaluated in BALB/c mice (n = 5 mice/group). |

TABLE 1E-continued

| Tetra-MAP derivatives of Mod3 (dendrimers) | |
|---|---|
| (K**IPVLDENGLFAP**-PEG2-KKC)4-<br>Maleimide4-MAP4<br>TetraMAP3.3<br>K**IPVLDENGLFAP**-D Lys-D Lys4-K2-K-<br>MAP4<br>TetraMAP3.4<br>K**IPVLDENGLFAP**GPC-D Lys-D Lys4-K2-<br>K-MAP4<br>Three GPC residues at the C-terminus (also present in PEP1) were added to Mod3 to examine their role in immunogenicity<br>Additional tetra-MAP peptides synthesized:<br>Tetra MAP1.1: control peptide; identical structure to original Tetra-MAP1, but made by modular synthesis<br>(CGP**IPVLDENGLFAP**GPC)4(Lys)2Lys-β-<br>Ala-COOH<br>Tetra MAP1.2: N-terminal Cys in TetraMAP1.1 replaced with Ser in attempt to reduce unwanted disulfide bond formation<br>SGP**IPVLDENGLFAP**GPC)4(Lys)2Lys-β-<br>Ala-COOH<br>Immunization studies (described in FIG. 18), in addition to using original stepwise synthesized antigens (Octa MAP1 and Tetra MAP1) and MOD3 derivatives for immunization, also included immunizations with Tetra MAP 1.1 and Tetra MAP 1.2 (n = 9 mice/group). TetraMAP1.1 (bottom row) elicited similar anti-LOS Ab levels as Tetra MAP1 (top row). | IgG against 2C7 + LOS was measured by ELISA. Original Octa MAP1 and TetraMAP1 compounds were included as historical (positive) controls, (described in FIG. 18). All Mod3 derivatives gave poor responses. |

TABLE 1F

Figure 19:
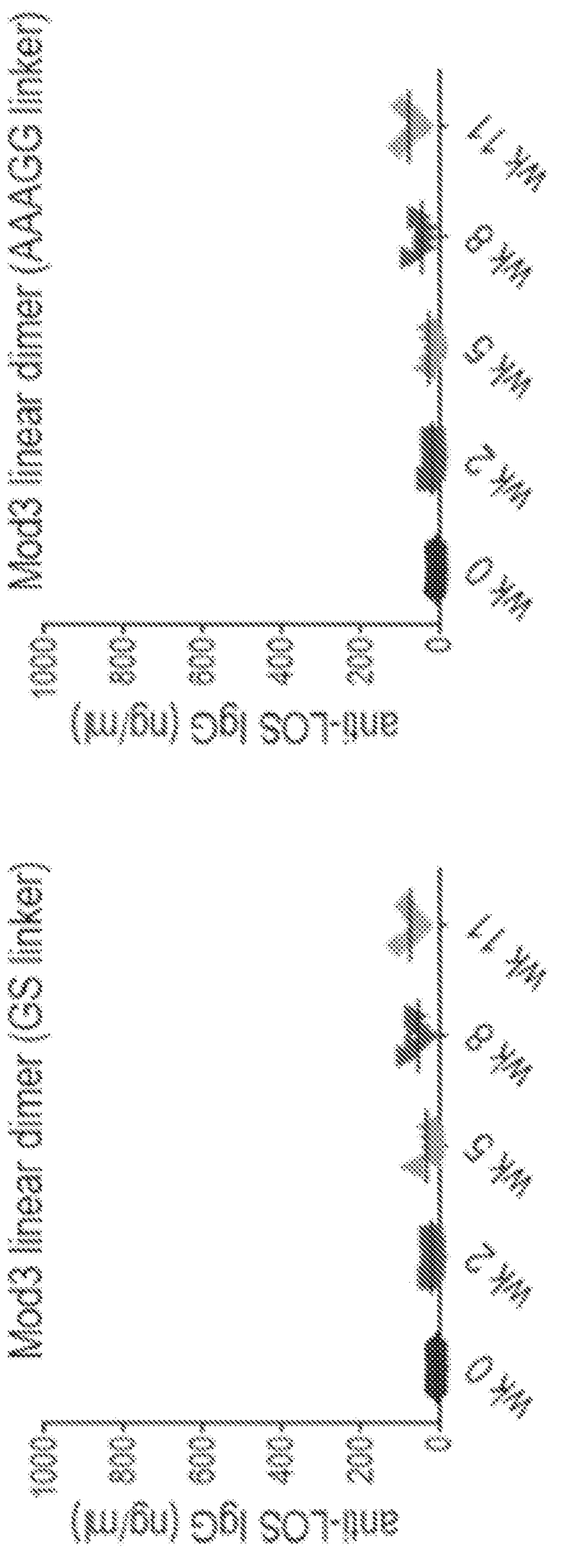
FIG. 19 shows linear peptides (Mod3 linear dimer with GS linker (italicized and underlined): KIPVLDENGL-FAPGSKIPVLDENGLFAP (SEQ ID NO: 4) and Mod3 linear dimer with AAAGG (SEQ ID NO: 5) linker (linker italicized and underlined): KIPVLDENGLFAPAAAGG-KIPVLDENGLFAP (SEQ ID NO: 6)) studied in 2C7 inhibition ELISA. The molecule with AAAGG linker inhibited mAb 2C7 binding to LOS better than the molecule with the AG linker, but neither were immunogenic in mice.

| Concatemers (dimers) derived from Mod3 sequence | |
|---|---|
| Concatemers (dimers) derived from Mod3 sequence<br>Mod3 linear dimer #1:<br>K**IPVLDENGLFAP**GSK**IPVLDENGLFAP**<br>(SEQ ID NO: 4)<br>Mod3 linear dimer #2:<br>K**IPVLDENGLFAP**AAAGGK**IPVLDENGLFAP**<br>(SEQ ID NO: 6) | Linear peptides were studied in 2C7 inhibition ELISA-the molecule with AAAGG linker inhibited mAb 2C7 binding to LOS better than the molecule with the AG linker (not shown), but neither were immunogenic in mice (described in FIG. 19). |

TABLE 1G

Figure 20B:
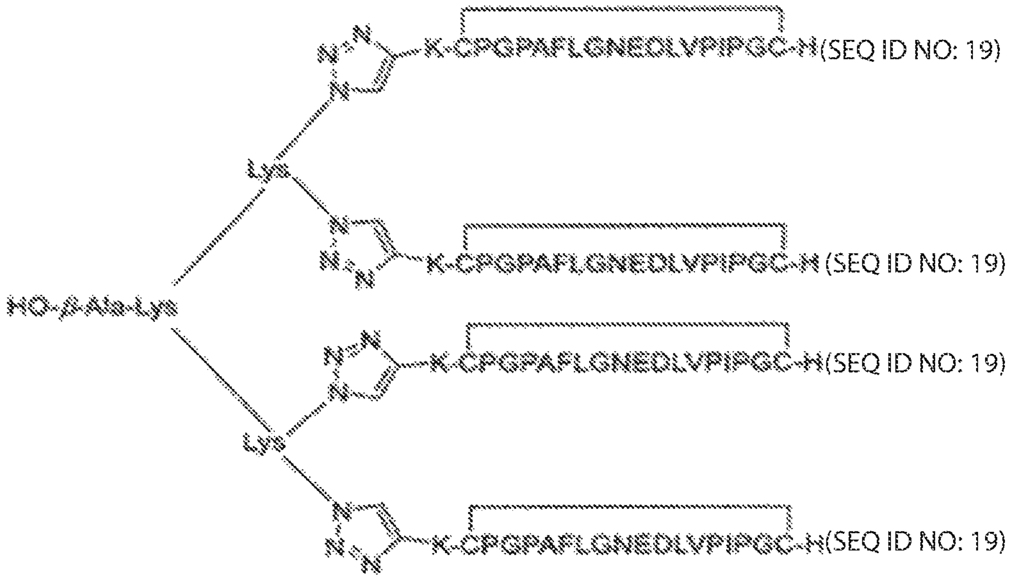

| Cyclic peptides and Core synthesized for Click chemistry linkage | |
|---|---|
| Click pep#1:<br>Cyclic H-(CGP**IPVLDENGLFAP**GPC (SEQ ID NO: 8))-K-alkyne<br>Click pep#2:<br>Cyclo H-(AGP**IPVLDENGLFAP**GPC (SEQ ID NO: 12)-K-alkyne<br>Click pep#3:<br>Cyclic Ac-(CGP**IPVLDENGLFAP**GPC (SEQ ID NO: 8))-K-OH<br>Click pep#4:<br>Cyclic GP(C**IPVLDENGLFAP**C (SEQ ID NO: 13))-GP-K-alkyne (synthesized to increase distance of Cys from Core)<br>Click Core 4:<br>(6-Azido-hexynoyl)4-Lys2-Lys-β-Ala-OH<br>(structure in FIG. 20A; structure in FIG. 20B represents expected product with Cyclic peptide #1) | Attempts to "click" the monomeric disulfide constrained peptides to the MAP Click-core 4 (6-Azido-hexynoyl)$_4$-Lys$_2$-Lys-β-Ala-OH (tetraMAP azide)) were minimally successful. RP-HPLC chromatography of the product after the reaction between the MAP Click-core showed only a small formation of the desired product with a large excess of residual substrate. Additional heterogeneity likely was caused by reduction of the disulfide bonds. This approach was abandoned. |

TABLE 1H

| Reverse MAP constructs | |
|---|---|
| TMCP2:<br>CH2-CO-GP**IPVLDENGLFAP**GPC (SEQ ID NO: 1))-K-OH<br>MAP construct is made up of 4 individual peptides (peptide shown above) that each contain stable non-reducible thioether bonds for cyclization; cyclized peptides have no free —SH to form inter-molecular bonds. C-terminus is linked to reverse MAP core<br>TMCP3:<br>Ac-CGP**IPVLDENGLFAP**GPC (SEQ ID NO: 8)-K-OH<br>MAP construct is made up of 4 individual peptides (peptide shown above) that contain internal S—S (disulfide) formed by the two cysteines (C); cyclized peptides have no free terminal —SH to form inter-molecular bonds but the internal S—S bonds are potentially reducible<br>TMCP4:<br>Ac-GP-(C**IPVLDENGLFAP**C (SEQ ID NO: 13))-GPK-OH<br>Same as TMCP3, but Cys at C-terminus was moved proximal (N-terminal) to the GP in order to move the cyclic peptide further away from the core.<br>Reverse MAP core:<br>Ac-N-β-Ala-Glu-(Glu)2-(COOH)4 | Reverse MAP constructs were developed as an inverse to the standard lysine branch approaches. Because each of the peptides were designed to contain only a single amine functional group, the development of a dendrimeric structure based upon a glutamic acid came about as a logical extension of this technology. The need for developing a combination solid-phase and solution process would help ensure a highly reproducible strategy, which would yield homogenous products. The key step in generating the tetraMAP was controlled by using a solution phase coupling step of highly purified monomers to the reverse tetra-MAP core. The reverse MAP core construct starting with the Ac-N-β-Ala-Glu-(Glu)2-(COOH)4 was designed to position four carboxyl groups for modification with amine components from the peptide monomers.<br>Inhibition ELISA assay-see FIG. 9<br>Immunogenicity (IgG responses elicited in BALB/c mice)-see FIG. 10<br>Serum bactericidal activity of immune sera-see FIG. 11<br>Based on manufacturability, its stable thioether bond for cyclization and elicited bactericidal activity, TMCP2 was selected as the lead candidate for further development. |

TABLE 2

Chemical structures of peptides tested

| # | Name | | Structure | Linker | MAP Core |
|---|---|---|---|---|---|
| 1 | Tetra MAP 1 | | (CGP**IPVLDENGLFAP**GPC (SEQ ID NO: 8))4 | No linker | (Lys)2Lys-β-Ala-COOH |
| 2 | Octa MAP 1 | | (CGP**IPVLDENGLFAP**GPC (SEQ ID NO: 8))8 | No linker | (Lys)4 (Lys)2 Lys-β-Ala-COOH |
| 3 | Tetra MAP 2 | | (CGPPEARDEGTITLERGPC (SEQ ID NO: 14))4 | No linker | (Lys)2Lys-β-Ala-COOH |
| — | Tetra MAP 1.1 | Api 1875 | (CGP**IPVLDENGLFAP**GPC (SEQ ID NO: 8))4 | | (Lys)2Lys-β-Ala-COOH |
| 4 | Tetra MAP 1.2 | Api 1876 | (SGP**IPVLDENGLFAP**GPC (SEQ ID NO: 15))4 | | (Lys)2Lys-β-Ala-COOH |
| 5 | Octa-MAP | Api 1873 | H2N-C(StBu)GP**IPVLDENGLFAP**GP(CysMal-PEG4)-amide]8(Lys7MAP)(bA)-amide | Ordered but unable to produce | |
| 6 | Octa-MAP | Api 1874 | H2N-SGP**IPVLDENGLFAP**GP(CysMal-PEG4)-amide]8(Lys7MAP)(bA)-amide | Ordered but unable to produce | |
| 7 | Mod 1 | 903482 | SGP**IPVLDENGLFAP**GPS (SEQ ID NO: 9) | N/A | |
| 8 | Mod 2 | 903483 | **IPVLDENGLFAP** (SEQ ID NO: 2) | -PEG2-KK)- | |
| 9 | Mod 3 | 903484 | K**IPVLDENGLFAP** (SEQ ID NO: 3) | -PEG2-KK)- | |
| 10 | Mod 4 | 903485 | SGP**IPVLDENGLFAP** (SEQ ID NO: 11) | -PEG2-KK)- | |

TABLE 2-continued

Chemical structures of peptides tested

| # | Name | Structure | Linker | MAP Core |
| --- | --- | --- | --- | --- |
| 11 | TMAP3.1 904680 | K**IPVLDENGLFAP** (SEQ ID NO: 3) | -PEG2-KK)- | -MAP4 |
| 12 | TMAP 3.2 904681 | K**IPVLDENGLFAP** (SEQ ID NO: 3) | -PEG2-KKC)- | 4-Maleimide4-MAP4 |
| 13 | TMAP 3.3 906164 | K**IPVLDENGLFAP** (SEQ ID NO: 3) (K = Lys) | -D-Lys-D-Lys4 'D-Lys' is the dextro-form of Lys | -K2-K-MAP4 |
| 14 | TMAP 3.4 906165 | K**IPVLDENGLFAP**GPC (SEQ ID NO: 10) | -D-Lys-D-Lys4 | -K2-K-MAP4 |
| 15 | Mod 3 dimer #1 | K**IPVLDENGLFAP**GSKK**IPVLDENGLFAP** (SEQ ID NO: 16) | Concatemer | |
| 16 | Mod 3 dimer #2 | K**IPVLDENGLFAP**AAAGGKK **IPVLDENGLFAP** (SEQ ID NO: 6) | Concatemer | |
| 17 | PCS-32325-PIC Cyclized peptide | cyclic-CGP-**IPVLDENGLFAP**-GPC-K-alkyne* (SEQ ID NO: 18) this is a disulfide constrained monomer (K = Lys) *(5-Hexynoyl)-OH | (N3K2-K-B-Ala-OH)* *There is no core because the structure is a disulfide constrained monomer: see the attached information sheet (PCS-32325-PI) (click chemistry was not successful) | |
| 18 | PCS-32328-PIC Cyclized peptide | cyclic-GPC-**IPVLDENGLFAP**-CGP-K-alkyne* (SEQ ID NO: 17) | (N3K2-K-B-Ala-OH) (click chemistry was not successful) | |
| 19 | PCS-32403-PI Cyclic Peptide 1 CP1 | cyclic Ac-CGP-**IPVLDENGLFAP**-GPC-K-OH (SEQ ID NO: 18) Same as cyclic peptide 3 (CP3) | | Tested as a monomer |
| 20 | PCS-32404-PI Cyclic Peptide 2 CP2 | (CH2-CO-GP**IPVLDENGLFAP**GPC)-K-OH (SEQ ID NO: 7) | | Tested as a monomer |
| — | PCS-32327-PI Cyclic 3 CP3 Peptide | cyclic Ac-CGP-**IPVLDENGLFAP**-GPC-K-OH (SEQ ID NO: 18) Same as cyclic peptide 1 | | Tested as a monomer |
| 21 | PCS-32405-PI Cyclic Peptide 4 CP4 | Ac-GP-(C**IPVLDENGLFAP**C)-GP-K-OH (SEQ ID NO: 17) | | Tested as a monomer |
| 22 | PCS-32330-PI Tetra MAP Cyclic Peptide 2; TMCP2 reverse | [(CH2-CO-GP**IPVLDENGLFAP**GPC)-K-OH]4 (SEQ ID NO: 7) | | Glu2-Glu-βAla-N-Ac —NH2 group of the K (Lys) links to the —COOH group of Glu "reverse linkage") |
| 23 | PCS-32331-PI Tetra MAP Cyclic Peptide 3; TMCP3 reverse | [Ac-(CGP**IPVLDENGLFAP**GPC)-K-OH]4 (SEQ ID NO: 18) | | Glu2-Glu-βAla-N-Ac "reverse linkage |

TABLE 2-continued

| Chemical structures of peptides tested | | | | | |
|---|---|---|---|---|---|
| # | Name | | Structure | Linker | MAP Core |
| 24 | PCS-32332-PI | Tetra MAP Cyclic Peptide 4; TMCP4 reverse | [Ac-GP-(C**IPVLDENGLFAP**C)-GP-K-OH]4 (SEQ ID NO: 17) | | Glu2-Glu-βAla-N-Ac "reverse linkage" |
| — | PCS-32329-PI | | [Ac-(CGP**IPVLDENGLFAP**GPC)-K-OH]4 (SEQ ID NO: 18) | | |

TABLE 3

| Bactericidal activity of naïve mouse sera against *N. gonorrhoeae* FA1090 | | | | |
|---|---|---|---|---|
| Mouse strain | Source | Length of time housed at UMass | Titer (%) of heat-inactivated mouse serum used in serum bactericidal assay | Number of animals with bactericidal activity [A] (%) versus FA1090 |
| BALB/c | Charles River | <2 days | 1:6 (16.6%) | 5/8 (63%) |
| BALB/c | Jackson | >4 months | ≥1:6 (≥16.6%) | 4/4 (100%) |
| BALB/c | Jackson (parent) | Bred at UMass for 3 generations | ≥1:3 (≥33%) | 5/5 (100%) |
| BALB/c | Envigo | <2 days | 1:6 (16.6%) | 9/9 (100%) |
| BALB/c | Taconic | <2 days | 1:15 (6.7%) | 3/5 (60%) |
| CMAH$^{-/-}$ (BALB/c background) | Univ, of California, San Diego | Bred for > 5 generations | ≥1:3 (≥33%) | 2/2 (100%) |
| C3$^{-/-}$ (C57BL6 backcrossed into BALB/c background) | Jackson (parent) | Bred at UMass for > 8 generations | ≥1:3 (≥33%) | 1/3 (33%) |
| Rag 1$^{-/-}$ (BALB/c background) | Jackson (parent) | Bred at UMass for > 5 generations | ≥1:3 (≥33%) | 0/5 (0%) |
| JhD (BALB/c background) | Jackson (parent) | Bred at UMass for > 5 generations | 1:15 (6.7%) | 0/1 (0%) |
| JhD$^{+/-}$ (BALB/C background) | Jackson (parent) | Bred at UMass for > 5 generations | 1:15 (6.7%) | 2/2 (100%) |

[A] Bactericidal activity is defined as ≤ 50% survival following 30 min of incubation with 17% normal human serum (NHS) as the complement source.

TABLE 4

| Complement-dependent killing of *N. gonorrhoeae* FA1090 in intact and IgM-depleted immune sera [A] | | | | | | |
|---|---|---|---|---|---|---|
| | Survival in intact immune serum % (dilution) of immune serum | | | Survival in IgM-depleted immune serum % (dilution) of immune serum | | |
| Mouse # | 3.3% (1/30) | 6.7% (1/15) | 16.7% (1/6) | 3.3% (1/30) | 6.7% (1/15) | 16.7% (1/6) |
| 50 μg/dose | | | | | | |
| 50-1 | 81.13 | 71.50 | 49.24 | 89.15 | 76.53 | 53.71 |
| 50-2 | 21.21 | 15.00 | 9.95 | 29.30 | 21.78 | 15.00 |
| 50-3 | 16.59 | 10.71 | 1.90 | 19.91 | 14.93 | 3.41 |
| 50-4 | 16.33 | 5.43 | 0.00 | 22.03 | 17.81 | 2.24 |
| 50-5 | 2.84 | 0.47 | 0.00 | 5.38 | 2.33 | 0.00 |
| 100 μg/dose | | | | | | |
| 100-1 | 11.43 | 0.52 | 0.00 | 16.67 | 4.57 | 0.90 |
| 100-2 | 35.42 | 22.48 | 5.21 | 47.17 | 18.34 | 11.42 |

TABLE 4-continued

Complement-dependent killing of *N. gonorrhoeae* FA1090 in intact and IgM-depleted immune sera [A]

| Mouse # | Survival in intact immune serum % (dilution) of immune serum 3.3% (1/30) | 6.7% (1/15) | 16.7% (1/6) | Survival in IgM-depleted immune serum % (dilution) of immune serum 3.3% (1/30) | 6.7% (1/15) | 16.7% (1/6) |
|---|---|---|---|---|---|---|
| 100-3 | 2.54 | 0.48 | 0.47 | 8.07 | 0.89 | 0.46 |
| 100-4 | 59.60 | 44.19 | 33.33 | 76.23 | 61.40 | 48.89 |
| 100-5 | 64.82 | 46.30 | 27.41 | 76.44 | 50.00 | 34.51 |
| 200 μg/dose | | | | | | |
| 100-1 | 9.81 | 5.21 | 0.00 | 9.61 | 4.89 | 1.79 |
| 100-2 | 26.39 | 0.93 | 0.00 | 33.64 | 2.28 | 1.93 |
| 100-3 | 2.00 | 0.00 | 0.00 | 3.56 | 1.91 | 0.00 |
| 100-4 | 74.88 | 43.12 | 6.19 | 85.02 | 54.50 | 10.73 |
| Adj. cont. | | | | | | |
| A-1 | ND [B] | ND | 108.75 | ND | ND | 114.29 |
| A-2 | ND | ND | 109.47 | ND | ND | 111.59 |
| A-3 | ND | ND | 109.58 | ND | ND | 111.66 |
| A-4 | ND | ND | 110.79 | ND | ND | 116.63 |
| A-5 | ND | ND | 109.31 | ND | ND | 113.27 |

[A] Normal human serum (16.7%) was used as the complement source

[B] ND; not done

TABLE 5

Complement-dependent killing of *N. gonorrhoeae* FA1090 in intact and IgM-depleted immune sera [A]

| Mouse # | Survival in intact immune serum % (dilution) of immune serum 10% (1/10) | 12.5% (1/8) | 16.7% (1/6) | Survival in IgM-depleted immune serum % (dilution) of immune serum 10% (1/10) | 12.5% (1/8) | 16.7% (1/6) |
|---|---|---|---|---|---|---|
| 50 μg/dose | | | | | | |
| 50-1 | 48.10 | 30.23 | 8.96 | 56.17 | 46.73 | 29.34 |
| 50-2 | 23.12 | 11.50 | 1.49 | 61.90 | 27.66 | 10.13 |
| 50-3 | 21.67 | 6.63 | 0.00 | 62.86 | 34.72 | 13.54 |
| 50-4 | 50.73 | 27.86 | 16.24 | 66.51 | 47.96 | 33.63 |
| 50-5 | 59.02 | 27.27 | 7.39 | 75.71 | 50.23 | 29.65 |
| 50-6 | 48.74 | 40.39 | 24.50 | 58.37 | 43.26 | 36.07 |
| 50-7 | 50.25 | 34.17 | 15.42 | 59.73 | 42.40 | 24.00 |
| 50-8 | 56.28 | 48.50 | 16.75 | 67.25 | 52.53 | 23.45 |
| 50-9 | 45.73 | 38.24 | 10.45 | 56.33 | 49.78 | 36.65 |
| 50-10 | 41.12 | 25.62 | 5.45 | 52.61 | 34.88 | 9.72 |
| 50-11 | 39.20 | 27.09 | 6.28 | 48.39 | 38.46 | 10.96 |
| 50-12 | 50.50 | 39.49 | 22.17 | 68.00 | 48.62 | 34.12 |
| 50-13 | 57.50 | 30.10 | 1.50 | 61.84 | 39.73 | 15.42 |
| 100 μg/dose | | | | | | |
| 100-1 | 49.25 | 10.55 | 3.05 | 58.41 | 26.11 | 20.20 |
| 100-2 | 21.43 | 14.50 | 8.59 | 30.00 | 25.58 | 20.87 |
| 100-3 | 23.90 | 10.10 | 3.78 | 31.75 | 14.93 | 9.33 |
| 100-4 | 52.04 | 29.35 | 19.39 | 55.72 | 42.47 | 30.14 |
| 100-5 | 31.07 | 14.14 | 1.00 | 39.05 | 18.55 | 2.79 |
| 100-6 | 37.31 | 4.85 | 0.50 | 60.00 | 21.43 | 1.67 |
| 100-7 | 20.29 | 9.14 | 4.02 | 27.23 | 19.38 | 15.15 |
| 100-8 | 65.85 | 49.75 | 15.27 | 78.74 | 59.15 | 23.24 |
| 100-9 | 31.12 | 15.27 | 0.00 | 48.79 | 28.40 | 3.14 |
| 100-10 | 36.36 | 8.76 | 0.00 | 57.21 | 26.27 | 2.39 |
| 100-11 | 33.50 | 10.71 | 4.04 | 39.04 | 20.27 | 10.92 |
| 100-12 | 23.15 | 3.98 | 0.50 | 56.28 | 20.35 | 2.16 |
| 100-13 | 40.40 | 16.99 | 2.45 | 53.11 | 25.11 | 2.78 |
| 200 μg/dose | | | | | | |
| 200-1 | 52.66 | 27.75 | 6.53 | 50.00 | 26.42 | 14.23 |
| 200-2 | 54.64 | 38.50 | 7.85 | 46.00 | 32.20 | 16.33 |
| 200-3 | 53.23 | 25.91 | 6.47 | 50.21 | 31.90 | 23.08 |
| 200-4 | 38.07 | 19.90 | 0.00 | 54.11 | 28.63 | 16.20 |
| 200-5 | 24.74 | 5.97 | 0.51 | 50.00 | 27.49 | 8.68 |
| 200-6 | 22.39 | 0.00 | 0.00 | 42.01 | 18.67 | 13.49 |
| 200-7 | 28.00 | 4.06 | 2.06 | 46.89 | 22.75 | 15.12 |
| 200-8 | 31.47 | 10.88 | 0.00 | 49.77 | 32.86 | 16.16 |

TABLE 5-continued

Complement-dependent killing of *N. gonorrhoeae* FA1090 in intact and IgM-depleted immune sera [A]

| Mouse # | Survival in intact immune serum % (dilution) of immune serum | | | Survival in IgM-depleted immune serum % (dilution) of immune serum | | |
|---|---|---|---|---|---|---|
| | 10% (1/10) | 12.5% (1/8) | 16.7% (1/6) | 10% (1/10) | 12.5% (1/8) | 16.7% (1/6) |
| 200-9 | 11.92 | 0.50 | 0.00 | 54.59 | 22.57 | 3.90 |
| 200-10 | 8.29 | 1.46 | 0.00 | 23.14 | 18.35 | 21.00 |
| 200-11 | 23.23 | 6.67 | 1.94 | 55.00 | 36.86 | 20.76 |
| 200-12 | 16.58 | 4.08 | 3.02 | 42.86 | 26.05 | 10.55 |
| 200-13 | 39.59 | 15.34 | 1.01 | 57.64 | 31.94 | 7.21 |
| Adj. control | | | | | | |
| A-1 | ND [B] | ND | 111.11 | ND | ND | 107.59 |
| A-2 | ND | ND | 108.10 | ND | ND | 118.58 |
| A-3 | ND | ND | 109.13 | ND | ND | 117.08 |
| A-4 | ND | ND | 109.58 | ND | ND | ND |
| A-5 | ND | ND | 109.21 | ND | ND | ND |
| A-6 | ND | ND | 108.33 | ND | ND | ND |
| A-7 | ND | ND | 110.37 | ND | ND | ND |
| A-8 | ND | ND | 108.75 | ND | ND | ND |
| A-9 | ND | ND | 112.03 | ND | ND | ND |
| A-10 | ND | ND | 112.35 | ND | ND | ND |
| A-11 | ND | ND | 110.25 | ND | ND | ND |
| A-12 | ND | ND | 111.52 | ND | ND | ND |
| A-13 | ND | ND | 111.43 | ND | ND | ND |

[A] Normal human serum (16.7%) was used as a source of complement;
[B] ND; not done

TABLE 6

Complement-dependent killing of *N. gonorrhoeae* MS11 in intact and IgM-depleted immune sera [A]

| Mouse # | Survival in intact immune serum % (dilution) of immune serum | | | Survival in IgM-depleted immune serum % (dilution) of immune serum | | |
|---|---|---|---|---|---|---|
| | 1.3% (1/75) | 3.3% (1/30) | 6.7% (1/15) | 1.3% (1/75) | 3.3% (1/30) | 6.7% (1/15) |
| 50 μg/dose | | | | | | |
| 50-1 | 18.27 | 0.48 | 0.00 | 40.52 | 19.75 | 3.11 |
| 50-2 | 39.90 | 26.47 | 0.00 | 72.26 | 41.03 | 10.98 |
| 50-3 | 49.28 | 19.91 | 0.00 | 82.67 | 45.00 | 12.58 |
| 50-4 | 15.50 | 0.00 | 0.00 | 35.00 | 0.00 | 0.00 |
| 50-5 | 6.03 | 0.99 | 0.00 | 21.94 | 0.00 | 0.00 |
| 50-6 | 14.78 | 0.51 | 0.00 | 26.99 | 0.00 | 0.00 |
| 50-7 | 10.50 | 0.97 | 0.00 | 23.53 | 0.00 | 0.00 |
| 50-8 | 22.93 | 7.39 | 1.52 | 38.75 | 12.66 | 2.65 |
| 50-9 | 10.61 | 0.00 | 0.00 | 25.48 | 0.00 | 0.00 |
| 50-10 | 18.60 | 9.95 | 0.00 | 44.30 | 11.66 | 4.52 |
| 50-11 | 31.66 | 11.33 | 0.00 | 37.75 | 16.34 | 0.63 |
| 50-12 | 19.91 | 0.48 | 0.47 | 27.10 | 0.00 | 0.00 |
| 50-13 | 47.85 | 19.43 | 0.93 | 64.67 | 34.62 | 9.82 |
| Adj. cont. | | | | | | |
| A-1 | ND | ND | 108.53 | ND | ND | 109.38 |
| A-2 | ND | ND | 113.59 | ND | ND | 112.99 |

[A] Normal human serum depleted of IgG and IgM (Human complement [Pel-Freez]) 6.7% was used as the source of complement
[B] ND; not done

Figure 21:
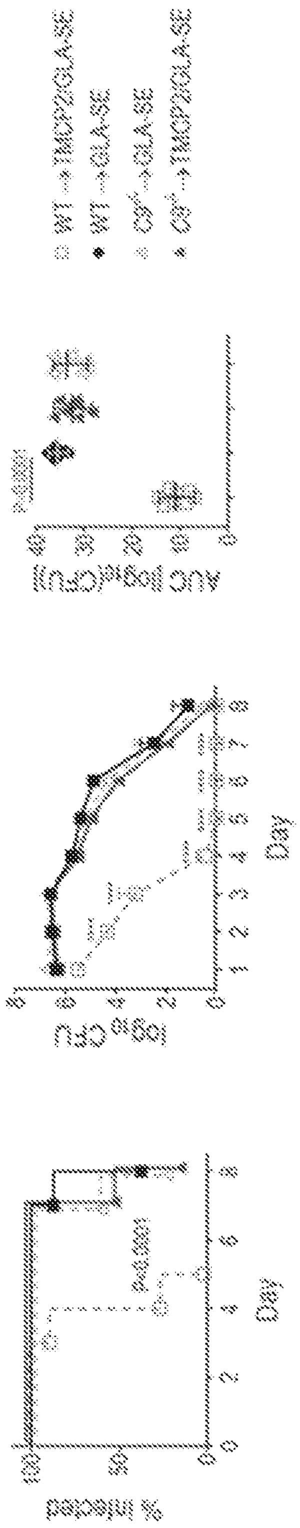
FIG. 21 shows results showing that the TMCP2 likely functions through direct killing by the terminal complement pore (e.g., the membrane attack complex). Kaplan-Meier curves for time to clearance of infection (analyzed by Mantel-Cox Log Rank test) (leftmost panel). $\log_{10}$ CFU vs time (comparisons by 2-way ANOVA; ****, P<0.0001) (middle panel). Area Under Curve (AUC) analysis (groups compared by one-way ANOVA using Kruskal Wallis' non-parametric test and pairwise comparisons were made with Dunn's test) (rightmost panel).

Example 2: An Intact Terminal Complement Pathway Affects the Efficacy of the TMCP2 Vaccine Wild-type C57BL/6 mice or C9−/− mice (lack terminal complement) were immunized were immunized intramuscularly with either TMCP2 vaccine plus glucopyranosyl lipid adjuvant-stable emulsion (GLA-SE) adjuvant, or with GLA-SE alone at 0, 3, and 6 weeks. Two weeks after the third dose, mice were challenged with *N. gonorrhoeae* strain FA1090 ($3\times10^7$ CFU) intravaginally (n=8 mice/group). Vaginas were swabbed daily to obtain CFUs. Kaplan-Meier curves for time to clearance of infection (analyzed by Mantel-Cox Log Rank test) (FIG. 21, leftmost panel). $\log_{10}$ CFU vs time (comparisons by 2-way ANOVA; **, P<0.0001) (FIG. 21, middle panel). Area Under Curve (AUC) analysis (groups compared by one-way ANOVA using Kruskal Wallis' non-parametric test and pairwise comparisons were made with Dunn's test) (FIG. 21**, rightmost panel).

REFERENCES

1. Weston E J, Workowski K, Torrone E, Weinstock H, Stenger M R. 2018. Adherence to CDC Recommendations for the Treatment of Uncomplicated Gonorrhea—STD Surveillance Network, United States, 2016. MMWR Morb Mortal Wkly Rep 67:473-476.
2. Costa-Lourenco A, Barros Dos Santos K T, Moreira B M, Fracalanzza S E L, Bonelli R R. 2017. Antimicrobial resistance in *Neisseria gonorrhoeae*: history, molecular mechanisms and epidemiological aspects of an emerging global threat. Braz J Microbiol 48:617-628.
3. Unemo M, Del Rio C, Shafer W M. 2016. Antimicrobial Resistance Expressed by *Neisseria gonorrhoeae*: A Major Global Public Health Problem in the 21st Century. Microbiol Spectr 4.
4. Unemo M, Shafer W M. 2014. Antimicrobial resistance in *Neisseria gonorrhoeae* in the 21st century: past, evolution, and future. Clin Microbiol Rev 27:587-613.
5. Rice P A, Shafer W M, Ram S, Jerse A E. 2017. *Neisseria gonorrhoeae*: Drug Resistance, Mouse Models, and Vaccine Development. Annu Rev Microbiol 71:665-686.
6. Schmidt K A, Schneider H, Lindstrom J A, Boslego J W, Warren R A, Van de Verg L, Deal C D, McClain J B, Griffiss J M. 2001. Experimental gonococcal urethritis and reinfection with homologous gonococci in male volunteers. Sex Transm Dis 28:555-64.

7. Gulati S, McQuillen D P, Mandrell R E, Jani D B, Rice P A. 1996. Immunogenicity of *Neisseria gonorrhoeae* lipooligosaccharide epitope 2C7, widely expressed in vivo with no immunochemical similarity to human glycosphingolipids [published erratum appears in J Infect Dis 1997 April; 175(4):1027]. J Infect Dis 174:1223-37.
8. Hook E W, Olsen D A, Buchanan T M. 1984. Analysis of antigen specificity of the human serum immunoglobulin G immune response to complicated gonococcal infection. Infect Immun 43:706-709.
9. Brooks G F, Lammel C J. 1989. Humoral immune response to gonococcal infections. Clin Micro Rev 2S: S5-S10.
10. Yamasaki R, Koshino H, Kurono S, Nishinaka Y, McQuillen D P, Kume A, Gulati S, Rice P A. 1999. Structural and immunochemical characterization of a *Neisseria gonorrhoeae* epitope defined by a monoclonal antibody 2C7; the antibody recognizes a conserved epitope on specific lipo-oligosaccharides in spite of the presence of human carbohydrate epitopes. J Biol Chem 274:36550-8.
11. Chakraborti S, Lewis L A, Cox A D, St Michael F, Li J, Rice P A, Ram S. 2016. Phase-Variable Heptose I Glycan Extensions Modulate Efficacy of 2C7 Vaccine Antibody Directed against *Neisseria gonorrhoeae* Lipooligosaccharide. J Immunol 196:4576-86.
12. Banerjee A, Wang R, Uljon S N, Rice P A, Gotschlich E C, Stein D C. 1998. Identification of the gene (lgtG) encoding the lipooligosaccharide beta chain synthesizing glucosyl transferase from *Neisseria gonorrhoeae*. Proc Natl Acad Sci USA 95:10872-7.
13. Gulati S, Zheng B, Reed G W, Su X, Cox A D, St Michael F, Stupak J, Lewis L A, Ram S, Rice P A. 2013. Immunization against a Saccharide Epitope Accelerates Clearance of Experimental Gonococcal Infection. PLoS Pathog 9: e1003559.
14. Lam J. 2017. Genetic Adaptation Contributing to Increased Gonococcal Fitness during Vaginal Infection of CEACAM-humanized Mice. Master's. University of Toronto.
15. Ram S, Gulati S, Lewis L A, Chakraborti S, Zheng B, DeOliveira R B, Reed G W, Cox A D, Li J, St Michael F, Stupak J, Su X H, Saha S, Landig C S, Varki A, Rice P A. 2018. A Novel Sialylation Site on *Neisseria gonorrhoeae* Lipooligosaccharide Links Heptose II Lactose Expression with Pathogenicity. Infect Immun 86.
16. Ram S, Gulati S, Lewis L A, Chakraborti S, Zheng B, DeOliveira R B, Reed G W, Cox A D, Li J, St Michael F, Stupak J, Su X H, Saha S, Landig C S, Varki A, Rice P A. 2018. A novel sialylation site on *Neisseria gonorrhoeae* lipooligosaccharide links heptose I I lactose expression with pathogenicity. Infect Immun doi:10.1128/IAI.00285-18.
17. Landig C S, Hazel A, Kellman B P, Fong J J, Schwarz F, Agarwal S, Varki N, Massari P, Lewis N E, Ram S, Varki A. 2018. Evolution of the exclusively human pathogen *Neisseria gonorrhoeae*: Human-specific engagement of immunoregulatory Siglecs. Evol Appl.
18. Gulati S, McQuillen D P, Mandrell R E, Jani D B, Rice P A. 1996. Immunogenicity of *Neisseria gonorrhoeae* lipooligosaccharide epitope 2C7, widely expressed in vivo with no immunochemical similarity to human glycosphingolipids. J Infect Dis 174:1223-37.
19. Ngampasutadol J, Rice P A, Walsh M T, Gulati S. 2006. Characterization of a peptide vaccine candidate mimicking an oligosaccharide epitope of *Neisseria gonorrhoeae* and resultant immune responses and function. Vaccine 24:157-70.
20. Cohen M S, Cannon J G, Jerse A E, Charniga L M, Isbey S F, Whicker L G. 1994. Human experimentation with *Neisseria gonorrhoeae*: rationale, methods, and implications for the biology of infection and vaccine development. J Infect Dis 169:532-7.
21. Swanson J, Robbins K, Barrera 0, Corwin D, Boslego J, Ciak J, Blake M, Koomey J M. 1987. Gonococcal pilin variants in experimental gonorrhea. J Exp Med 165:1344-57.
22. Yamasaki R, Kerwood D E, Schneider H, Quinn K P, Griffiss J M, Mandrell R E. 1994. The structure of lipooligosaccharide produced by *Neisseria gonorrhoeae*, strain 15253, isolated from a patient with disseminated infection: evidence for a new glycosylation pathway of gonococcal lipooligosaccharide. J Biol Chem 269:30345-30351.
23. Westphal O, Luderitz O, Bister F. 1952. Uber die extraktion von bacterien mit phenol/wasser. Z Naturforsch B7:148-155.
24. McQuillen D P, Gulati S, Rice P A. 1994. Complement-mediated bacterial killing assays. Methods Enzymol 236: 137-47.
25. Jerse A E. 1999. Experimental gonococcal genital tract infection and opacity protein expression in estradiol-treated mice. Infect Immun 67:5699-708.
26. Jerse A E, Wu H, Packiam M, Vonck R A, Begum A A, Garvin L E. 2011. Estradiol-Treated Female Mice as Surrogate Hosts for *Neisseria gonorrhoeae* Genital Tract Infections. Front Microbiol 2:107.
27. Ram S, Cullinane M, Blom A, Gulati S, McQuillen D, Monks B, O'Connell C, Boden R, Elkins C, Pangburn M, Dahlback B, Rice P A. 2001. Binding of $C_4$b-binding Protein to Porin: A molecular mechanism of serum resistance of *Neisseria gonorrhoeae*. J Exp Med 193:281-96.
28. Beernink P T, Ispasanie E, Lewis L A, Ram S, Moe G R, Granoff D M. 2018. A meningococcal native outer membrane vesicle vaccine with attenuated endotoxin and over-expressed Factor H binding protein elicits gonococcal bactericidal antibodies. J Infect Dis doi:10.1093/infdis/jiy609.
29. Diebolder C A, Beurskens F J, de Jong R N, Koning R I, Strumane K, Lindorfer M A, Voorhorst M, Ugurlar D, Rosati S, Heck A J, van de Winkel J G, Wilson I A, Koster A J, Taylor R P, Saphire E O, Burton D R, Schuurman J, Gros P, Parren P W. 2014. Complement is activated by IgG hexamers assembled at the cell surface. Science 343:1260-3.
30. Crew P E, Abara W E, McCulley L, Waldron P E, Kirkcaldy R D, Weston E J, Bernstein K T, C. J S, J. B-M S. 2018. Disseminated gonococcal infections in patients receiving eculizumab: a case series. Clin Infect Dis.
31. Ellison R T, 3rd, Curd J G, Kohler P F, Reller L B, Judson F N. 1987. Underlying complement deficiency in patients with disseminated gonococcal infection. Sex Transm Dis 14:201-4.
32. Snyderman R, Durack D T, McCarty G A, Ward F E, Meadows L. 1979. Deficiency of the fifth component of complement in human subjects. Clinical, genetic and immunologic studies in a large kindred. Am J Med 67:638-45.
33. Peter G, Weigert M B, Bissel A R, Gold R, Kreutzer D, McLean R H. 1981. Meningococcal meningitis in familial deficiency of the fifth component of complement. Pediatrics 67:882-6.

34. Liu Y, Hammer L A, Liu W, Hobbs M M, Zielke R A, Sikora A E, Jerse A E, Egilmez N K, Russell M W. 2017. Experimental vaccine induces Th1-driven immune responses and resistance to *Neisseria gonorrhoeae* infection in a murine model. Mucosal Immunol 10:1594-1608.
35. Jerse A E, Bash M C, Russell M W. 2014. Vaccines against gonorrhea: current status and future challenges. Vaccine 32:1579-87.
36. Liu Y, Perez J, Hammer L A, Gallagher H C, De Jesus M, Egilmez N K, Russell M W. 2018. Intravaginal Administration of Interleukin 12 during Genital Gonococcal Infection in Mice Induces Immunity to Heterologous Strains of *Neisseria gonorrhoeae*. mSphere 3.
37. Yip K S, Suvorov A, Connerney J, Lodato N J, Waxman D J. 2013. Changes in mouse uterine transcriptome in estrus and proestrus. Biol Reprod 89:13.
38. Churchill W H, Jr., Weintraub R M, Borsos T, Rapp H J. 1967. Mouse complement: the effect of sex hormones and castration on two of the late-acting components. J Exp Med 125:657-72.
39. Weintraub R M, Churchill W H, Jr., Crisler C, Rapp H J, Borsos T. 1966. Mouse complement: influence of sex hormones on its activity. Science 152:783-5.
40. Forward K R. 2010. Risk of coinfection with *Chlamydia trachomatis* and *Neisseria gonorrhoeae* in Nova Scotia. Can J Infect Dis Med Microbiol 21: e84-6.
41. Guy R, Ward J, Wand H, Rumbold A, Garton L, Hengel B, Silver B, Taylor-Thomson D, Knox J, McGregor S, Dyda A, Fairley C, Maher L, Donovan B, Kaldor J, Group S I. 2015. Coinfection with *Chlamydia trachomatis, Neisseria gonorrhoeae* and *Trichomonas vaginalis*: a cross-sectional analysis of positivity and risk factors in remote Australian Aboriginal communities. Sex Transm Infect 91:201-6.
42. Lim R B, Wong M L, Cook A R, Brun C, Chan R K, Sen P, Chio M. 2015. Determinants of *Chlamydia*, Gonorrhea, and Coinfection in Heterosexual Adolescents Attending the National Public Sexually Transmitted Infection Clinic in Singapore. Sex Transm Dis 42:450-6.
43. Giuliani M M, Adu-Bobie J, Comanducci M, Arico B, Savino S, Santini L, Brunelli B, Bambini S, Biolchi A, Capecchi B, Cartocci E, Ciucchi L, Di Marcello F, Ferlicca F, Galli B, Luzzi E, Masignani V, Serruto D, Veggi D, Contorni M, Morandi M, Bartalesi A, Cinotti V, Mannucci D, Titta F, Ovidi E, Welsch J A, Granoff D, Rappuoli R, Pizza M. 2006. A universal vaccine for serogroup B meningococcus. Proc Natl Acad Sci USA 103:10834-9.
44. Semchenko E A, Tan A, Borrow R, Seib K L. 2018. The serogroup B meningococcal vaccine Bexsero elicits antibodies to *Neisseria gonorrhoeae*. Clin Infect Dis doi: 10.1093/cid/ciy1061.
45. Zielke R A, Wierzbicki I H, Baarda B I, Gafken P R, Soge 00, Holmes K K, Jerse A E, Unemo M, Sikora A E. 2016. Proteomics-driven Antigen Discovery for Development of Vaccines Against Gonorrhea. Mol Cell Proteomics 15:2338-55.
46. Semchenko E A, Day C J, Seib K L. 2017. MetQ of *Neisseria gonorrhoeae* Is a Surface-Expressed Antigen That Elicits Bactericidal and Functional Blocking Antibodies. Infect Immun 85.
47. Wang S, Xue J, Lu P, Ni C, Cheng H, Han R, van der Veen S. 2018. Gonococcal MtrE and its surface-expressed Loop 2 are immunogenic and elicit bactericidal antibodies. J Infect 77:191-204.
48. Gotschlich E C. 1994. Genetic locus for the biosynthesis of the variable portion of *Neisseria gonorrhoeae* lipooligosaccharide. J Exp Med 180:2181-2190.
49. Tong Y, Arking D, Ye S, Reinhold B, Reinhold V, Stein D C. 2002. *Neisseria gonorrhoeae* strain PID2 simultaneously expresses six chemically related lipooligosaccharide structures. Glycobiology 12:523-33.
50. Danaher R J, Levin J C, Arking D, Burch C L, Sandlin R, Stein D C. 1995. Genetic basis of *Neisseria gonorrhoeae* lipooligosaccharide antigenic variation. J Bacteriol 177:7275-7279.
51. Gotschlich E C. 1994. Genetic locus for the biosynthesis of the variable portion of *Neisseria gonorrhoeae* lipooligosaccharide. J Exp Med 180:2181-2190.
52. Jennings M, Hood D, Peak R, Virji M, Moxon E. 1995. Molecular analysis of a locus for the biosynthesis and phase-variable expression of the lacto-N-neotetraose terminal lipopolysaccharide structure in *Neisseria meningitidis*. Mol Microbiol 18::729-740.
53. Yang Q L, Gotschlich E C. 1996. Variation of gonococcal lipoligosaccharide structure is due to alteration in poly-G tracts in lgt genes encoding glycosyl transferases. J Exp Med 183:323-327.
54. Crocker P R, Paulson J C, Varki A. 2007. Siglecs and their roles in the immune system. Nat Rev Immunol 7:255-66.
55. Ali S R, Fong J J, Carlin A F, Busch T D, Linden R, Angata T, Areschoug T, Parast M, Varki N, Murray J, Nizet V, Varki A. 2014. Siglec-5 and Siglec-14 are polymorphic paired receptors that modulate neutrophil and amnion signaling responses to group B *Streptococcus*. J Exp Med 211:1231-42.
56. Carlin A F, Chang Y C, Areschoug T, Lindahl G, Hurtado-Ziola N, King C C, Varki A, Nizet V. 2009. Group B *Streptococcus* suppression of phagocyte functions by protein-mediated engagement of human Siglec-5. J Exp Med 206:1691-9.
57. Lam J, Gray-Owen S D. 2016. Genetic adaptation contributing to increased gonococcal fitness during vaginal infection of CEACAM-humanized mice., abstr 20th International Pathogenic *Neisseria* Conference, Manchester, United Kingdom.
58. Gulati S, Beurskens F J, de Kreuk B J, Roza M, Zheng B, DeOliveira R B, Shaughnessy J, Nowak N A, Taylor R P, Botto M, He X, Ingalls R R, Woodruff™, Song W C, Schuurman J, Rice P A, Ram S. 2019. Complement alone drives efficacy of a chimeric antigonococcal monoclonal antibody. PLoS Biol 17: e3000323.
59. Giuliani M M, Monaci E, Leuzzi R, Pezzicoli A, Gianfaldoni C, Fontana L, Tavarini S, Bonci A, Norais N, Mori E, Paccani S R, Ros I M, Delany I, Pizza M. Exploiting in vitro and in vivo assays to evaluate the potential ability of 4CMenB to confer protection against *Neisseria gonorrhoeae*. P139. Abstr 21st International Pathogenic *Neisseria* Conference. Monterey, C A.
60. Gulati S, Agarwal S, Vasudhev S, Rice P A, Ram S. 2012. Properdin is critical for antibody-dependent bactericidal activity against *Neisseria gonorrhoeae* that recruit $C_4$b-binding protein. J Immunol 188:3416-25.

OTHER EMBODIMENTS

Embodiment 1. A compound of Formula (I):

(I)

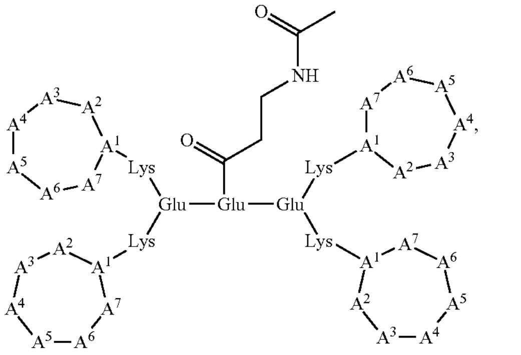

(I), or a salt or polymorph thereof, wherein: A1, A2, A3, A5, A6, and A7 are each independently a bond, an amino acid residue, substituted or unsubstituted acyl, substituted or unsubstituted alkylene, substituted or unsubstituted alkenylene, substituted or unsubstituted heteroalkylene, substituted or unsubstituted heterocyclylene, or substituted or unsubstituted heteroarylene, or a combination thereof; and A4 is a peptidyl sequence.

Embodiment 2. The compound of embodiment 1, or a salt or polymorph thereof, wherein: A1, A2, A3, A5, A6, and A7 are each independently an amino acid residue, substituted or unsubstituted acyl, or substituted or unsubstituted alkylene, or a combination thereof.

Embodiment 3. The compound of embodiment 1 or 2, or a salt or polymorph thereof, wherein: A1, A2, A3, A5, and A6 are each independently an amino acid residue.

Embodiment 6. The compound of any of embodiments 1-5, or a salt or polymorph thereof, wherein: A7 is an amino acid residue, substituted or unsubstituted acyl, or substituted or unsubstituted alkylene, or a combination thereof.

Embodiment 7. The compound of any of embodiments 1-6, or a salt or polymorph thereof, wherein: A7 is cysteine, substituted or unsubstituted acyl, or substituted or unsubstituted alkylene, or a combination thereof.

Embodiment 8. The compound of any of embodiments 1-7, or a salt or polymorph thereof, wherein: A7 is —(C═X)—$CR_2$—; wherein X is O or S, and each R is independently hydrogen, substituted or unsubstituted alkyl, or halogen.

Embodiment 9. The compound of any of embodiments 1-8, or a salt or polymorph thereof, wherein: A7 is *-(C═O)—$CH_2$—; wherein * indicates attachment to A6.

Embodiment 10. The compound of any of embodiments 1-9, or a salt or polymorph thereof, wherein: A4 is an antigenic peptidyl sequence.

Embodiment 11. The compound of any of embodiments 1-10, or a salt or polymorph thereof, wherein: A4 is a 12-mer antigenic peptidyl sequence.

Embodiment 12. The compound of any of embodiments 1-11, or a salt or polymorph thereof, wherein: A4 is a 12-mer antigenic peptidyl sequence, wherein each amino acid residue is independently isoleucine, proline, valine, leucine, aspartic acid, glutamic acid, asparagine, glycine, phenylalanine, or alanine.

Embodiment 13. The compound of any of embodiments 1-12, or a salt or polymorph thereof, wherein: A4 is *-Ile-Pro-Val-Leu-Asp-Glu-Asn-Gly-Leu-Phe-Ala-Pro- (SEQ ID NO: 2); wherein * indicates attachment to A5.

Embodiment 14. The compound of embodiment 1, wherein the compound of Formula (I) is of Formula (I-a):

(I-a)

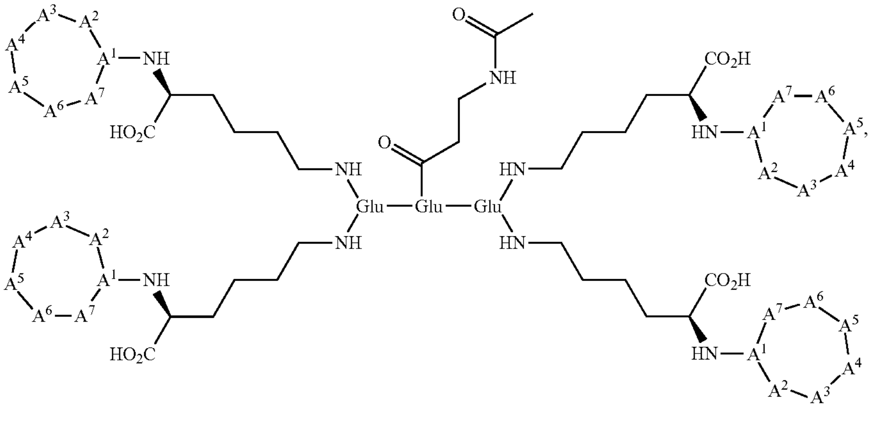

Embodiment 4. The compound of any of embodiments 1-3, or a salt or polymorph thereof, wherein: A1, A2, A3, A5, and A6 are each independently glycine, proline, or cysteine.

Embodiment 5. The compound of any of embodiments 1-4, or a salt or polymorph thereof, wherein: A1 is cysteine; and A2, A3, A5, and A6 are each independently glycine or proline.

or a salt or polymorph thereof.

Embodiment 15. The compound of embodiment 1, wherein the compound of Formula (I) is of Formula (I-b):

(I-b)
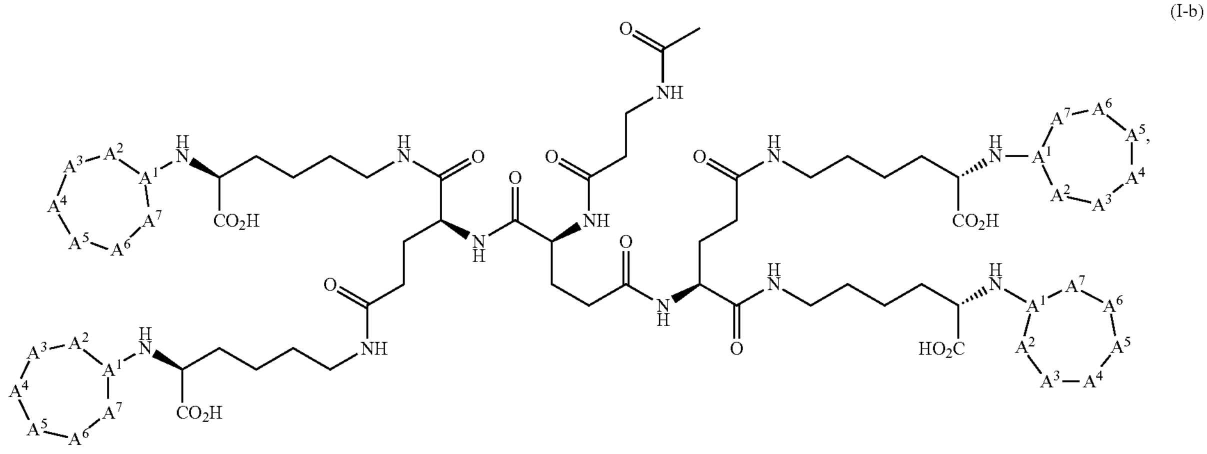
or a salt or polymorph thereof.
Embodiment 16. The compound of embodiment 1, wherein the compound of Formula (I) is of Formula (I-c):
(I-c)
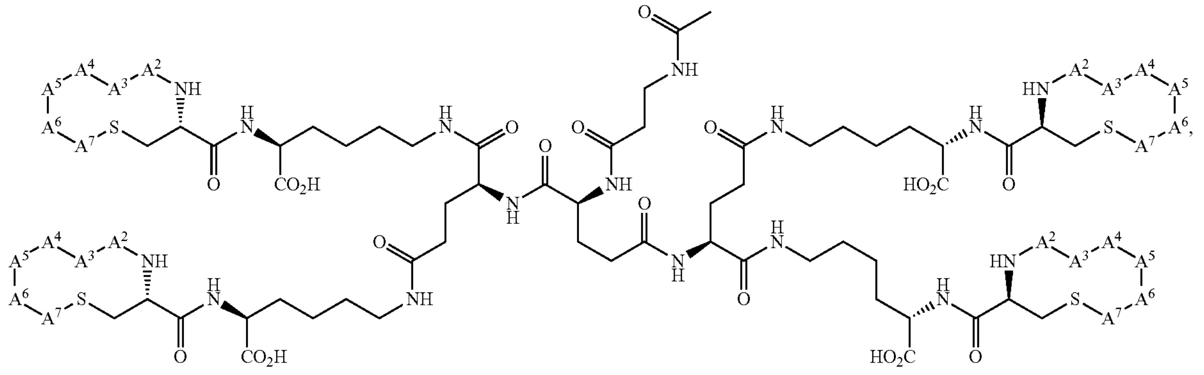
or a salt or polymorph thereof.
Embodiment 7. The compound of embodiment 1, wherein the compound of Formula (I) is of Formula (I-d):
(I-d)
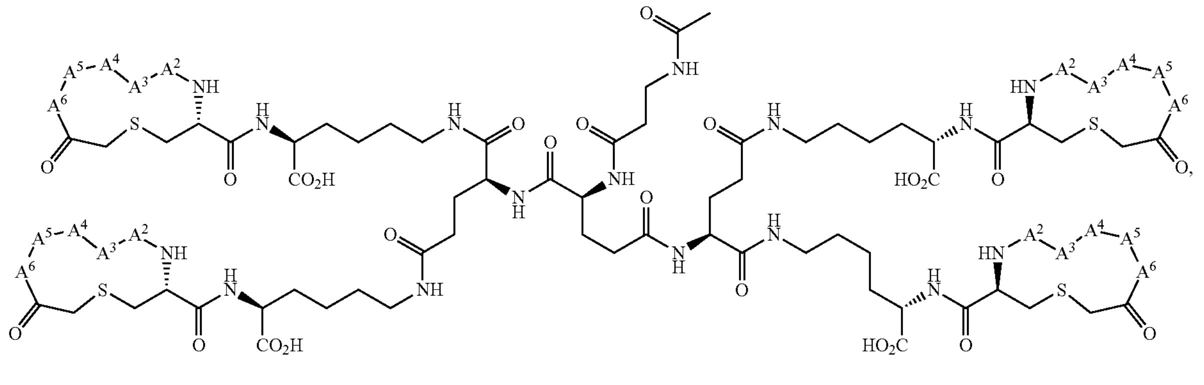
or a salt or polymorph thereof.

Embodiment 18. The compound of embodiment 1, wherein the compound of Formula (I) is of Formula (I-e):

(I-e)

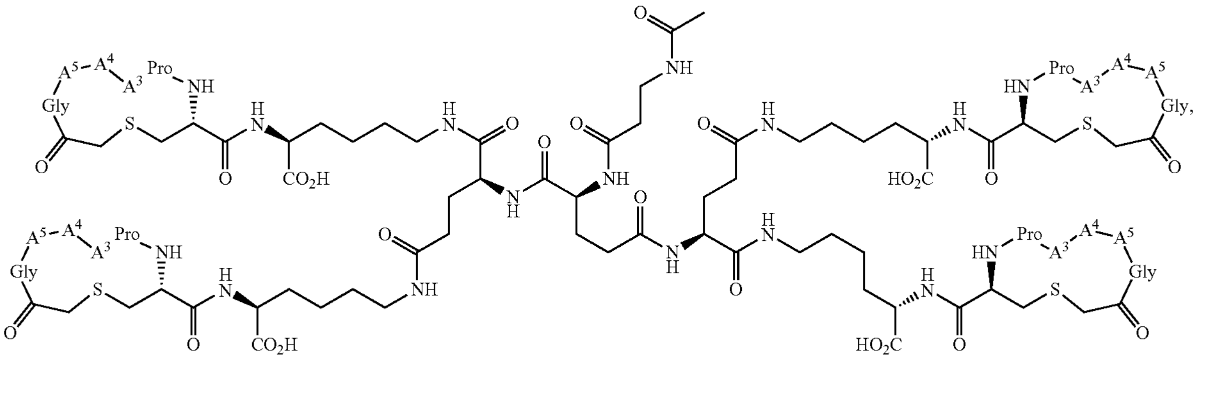

or a salt or polymorph thereof.

Embodiment 19. The compound of embodiment 1, wherein the compound of Formula (I) is of Formula (I-f):

(I-f)

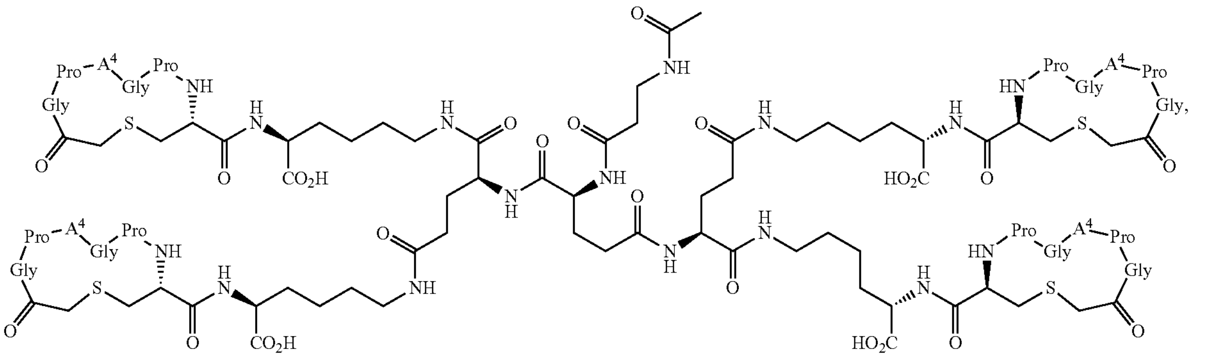

or a salt or polymorph thereof.

Embodiment 20. The compound of embodiment 19, or a salt or polymorph thereof, wherein: A4 is *-Ile-Pro-Val-Leu-Asp-Glu-Asn-Gly-Leu-Phe-Ala-Pro-, wherein * indicates attachment to Pro.

Embodiment 21. A compound of the formula:

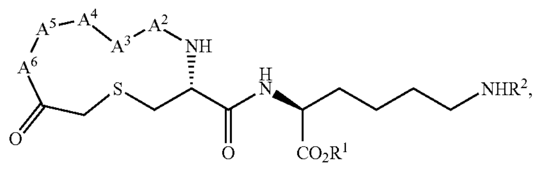

or a salt or polymorph thereof, wherein: A2, A3, A5, and A6 are each independently an amino acid residue; A4 is an antigenic peptidyl sequence; $R^1$ is hydrogen, a solid support resin, or a protecting group; and $R^2$ is hydrogen or a protecting group.

Embodiment 22. A compound of the formula:

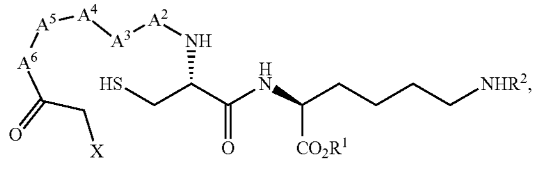

or a salt or polymorph thereof, wherein: X is a leaving group; A2, A3, A5, and A6 are each independently an amino acid residue; A4 is an antigenic peptidyl sequence; $R^1$ is hydrogen, a solid support resin, or a protecting group; and $R^2$ is hydrogen or a protecting group.

Embodiment 23. An peptide mimic of a conserved gonococcal lipo-oligosaccharide (LOS) epitope not found on human blood group antigens, wherein the peptide mimic is capable of inducing in a subject an immune response against the conserved gonococcal LOS epitope.

Embodiment 24. The peptide mimic of embodiment 23, wherein the peptide mimic comprises the amino acid sequence of IPVLDENGLFAP (SEQ ID NO: 2).

Embodiment 25. The peptide mimic according to embodiment 23-24, wherein the immune response is T-cell dependent.

Embodiment 26. The peptide mimic according to embodiment 23-25, wherein the amino acid sequence of the peptide mimic further comprises cysteine residues at each terminus.

Embodiment 27. The peptide mimic according to embodiment 26, wherein a cyclic peptide is formed through disulfide bridges between the cysteine residues at each terminus of the amino acid sequence.

Embodiment 28. The peptide mimic according to embodiment 23-27, wherein the peptide mimic is coupled to a second agent.

Embodiment 29. The peptide mimic according to embodiment 23-28, wherein the peptide comprises any of the compounds of embodiments 1-22 or the peptide mimics of embodiments 22-28.

Embodiment 30. The peptide mimic according to embodiment 29, wherein the peptide mimic competes with gonococcal lipooligosaccharide (LOS) for binding to monoclonal antibody 2C7 produced by a hybridoma cell line having the ATCC accession number HB-11859.

Embodiment 31. The peptide mimic according to embodiment 29, wherein the peptide mimic immuno-specifically binds to monoclonal antibody 2C7 produced by a hybridoma cell line having the ATCC accession number HB-11859.

Embodiment 32. The peptide mimic according to embodiment 29, wherein the peptide mimic immuno-specifically binds to a monoclonal antibody produced by immunizing a subject with an anti idiotypic monoclonal antibody, or fragment thereof, wherein the anti-idiotypic monoclonal antibody is produced by a hybridoma cell line having the ATCC accession number HB-11311.

Embodiment 33. A composition for immunizing against *N. gonorrhoeae* infection comprising the peptide mimic according to any one of embodiments 29-32.

Embodiment 34. A composition for immunizing against *N. gonorrhoeae* infection comprising a peptide mimic comprising the amino acid sequence of IPVLDENGLFAP.

Embodiment 35. A method of immunizing a subject against *N. gonorrhoeae* infection comprising administering to the subject an effective amount of the compounds of any one of embodiments 1-22 and/or any of the peptide mimics according to embodiment 23-29.

Embodiment 36. The peptide mimic according to embodiment 29, wherein the peptide mimic is coupled to a complement protein.

Embodiment 37. The peptide mimic according to embodiment 36, wherein the complement protein is $C_3d$.

Embodiment 38. A method of immunizing a subject against *N. gonorrhoeae* infection comprising administering to the subject an effective amount of the peptide mimic according to any one of embodiments 36-37.

Embodiment 39. A method for immunizing against *N. gonorrhoeae* infection comprising administering an effective amount of a composition comprising a peptide mimic according to embodiment 38 and a pharmaceutically acceptable carrier.

Embodiment 40. A method for increasing the antigenicity of the peptide mimic according to embodiment 29 comprising coupling the peptide mimic to a complement protein.

Embodiment 41. The method according to embodiment 40, wherein the complement protein is C3d.

Embodiment 42. The method according to any one of embodiments 35-38-41, wherein the subject has an active complement pathway.

In addition to the embodiments expressly described herein, it is to be understood that all of the features disclosed in this disclosure may be combined in any combination (e.g., permutation, combination). Each element disclosed in the disclosure may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, and can make various changes and modifications of the invention to adapt it to various usages and conditions. Thus, other embodiments are also within the claims.

Equivalents And Scope

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists (e.g., in Markush group format) each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms “comprising” and “containing” are intended to be open and permits the inclusion of additional elements or steps. Where ranges are given, endpoints are included.

Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This disclosure (i.e., the instant application) refers to various issued patents, published patent applications, journal articles, and other publications, all of which are incorporated herein by reference. If there is a conflict between any of the incorporated references and the disclosure, the disclosure shall control. In addition, any particular embodiment of the disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above description, but rather is as set forth in the appended claims. Those of ordinary skill in the art will appreciate that various changes and modifications to this description may be made without departing from the spirit or scope of the disclosure, as defined in the following claims.

The invention claimed is:

1. A compound of Formula (I-c):

(I-c)

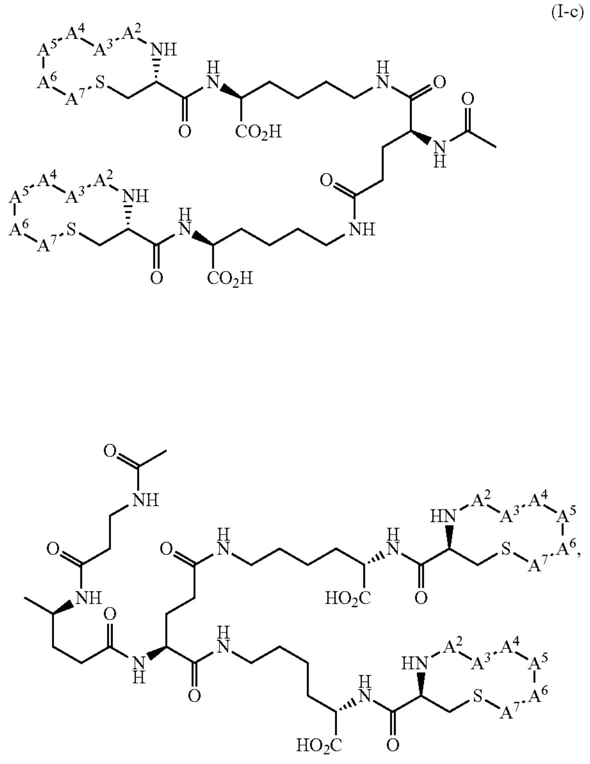

or a salt or polymorph thereof, wherein:

A2, A3, A5, and A6, are each independently glycine, proline, or cysteine

A4 is *-Ile-Pro-Val-Leu-Asp-Glu-Asn-Gly-Leu-Phe-Ala-Pro- (SEQ ID NO: 2), wherein * indicates attachment to A5; and A7 is *-(C═O)—$CH_2$—; wherein * indicates attachment to A6.

2. The compound of claim 1, wherein the compound of Formula (I-c) is

Formula (I-d):

(I-d)

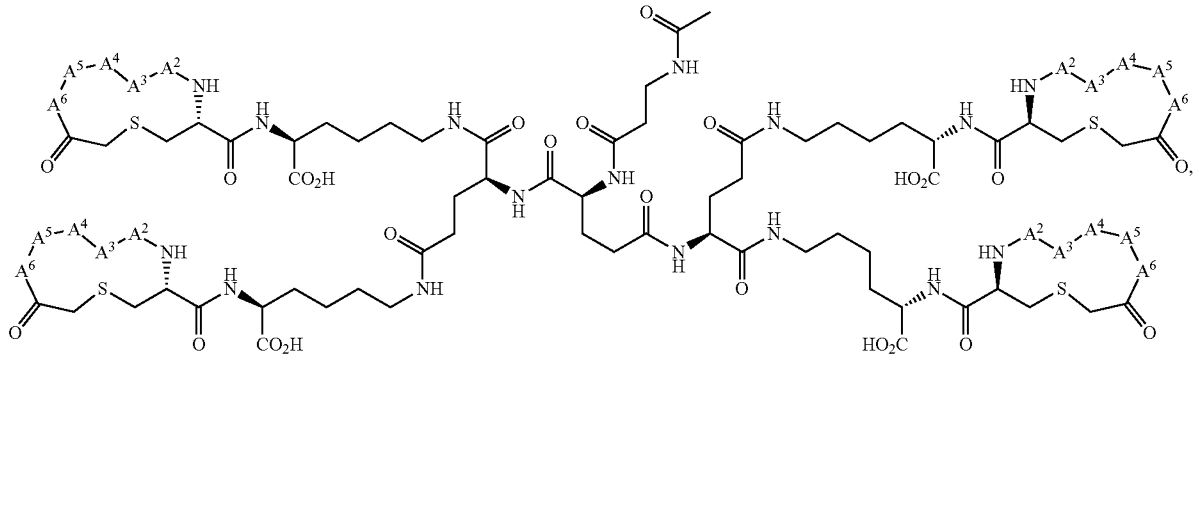

or a salt or polymorph thereof; or Formula (I-e):
(I-e)
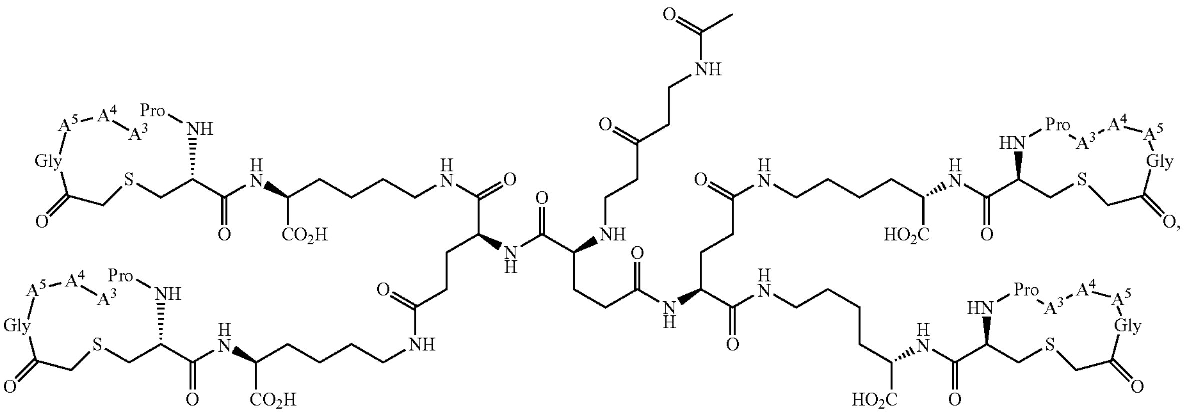
or a salt or polymorph thereof; or Formula (I-f):
(I-f)
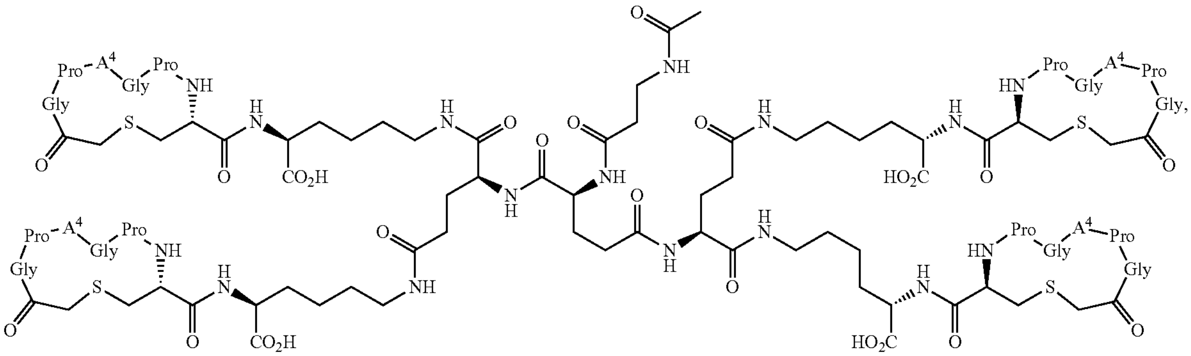
or a salt or polymorph thereof.
* * * * *

SEQUENCE LISTING

```
<160> NUMBER OF SEQ ID NOS: 19

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Gly Pro Ile Pro Val Leu Asp Glu Asn Gly Leu Phe Ala Pro Gly Pro
1               5                   10                  15

Cys


<210> SEQ ID NO 2
<211> LENGTH: 12
<212> TYPE: PRT
<213> ORGANISM: Artificial Sequence
<220> FEATURE:
<223> OTHER INFORMATION: Synthetic

<400> SEQUENCE: 2

Ile Pro Val Leu Asp Glu Asn Gly Leu Phe Ala Pro
1               5                   10


<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Lys Ile Pro Val Leu Asp Glu Asn Gly Leu Phe Ala Pro
1               5                   10


<210> SEQ ID NO 4
<211> LENGTH: 28
<212> TYPE: PRT
<213> ORGANISM: Artificial Sequence
<220> FEATURE:
<223> OTHER INFORMATION: Synthetic

<400> SEQUENCE: 4
```

-continued

Lys Ile Pro Val Leu Asp Glu Asn Gly Leu Phe Ala Pro Gly Ser Lys
1 5 10 15

Ile Pro Val Leu Asp Glu Asn Gly Leu Phe Ala Pro
20 25

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

Ala Ala Ala Gly Gly
1 5

<210> SEQ ID NO 6
<211> LENGTH: 31
<212> TYPE: PRT
<213> ORGANISM: Artificial Sequence
<220> FEATURE:
<223> OTHER INFORMATION: Synthetic

<400> SEQUENCE: 6

Lys Ile Pro Val Leu Asp Glu Asn Gly Leu Phe Ala Pro Ala Ala Ala
1 5 10 15

Gly Gly Lys Ile Pro Val Leu Asp Glu Asn Gly Leu Phe Ala Pro
20 25 30

<210> SEQ ID NO 7
<211> LENGTH: 18
<212> TYPE: PRT
<213> ORGANISM: Artificial Sequence
<220> FEATURE:
<223> OTHER INFORMATION: Synthetic

<400> SEQUENCE: 7

Gly Pro Ile Pro Val Leu Asp Glu Asn Gly Leu Phe Ala Pro Gly Pro
1 5 10 15

Cys Lys

<210> SEQ ID NO 8
<211> LENGTH: 18
<212> TYPE: PRT
<213> ORGANISM: Artificial Sequence
<220> FEATURE:
<223> OTHER INFORMATION: Synthetic

<400> SEQUENCE: 8

Cys Gly Pro Ile Pro Val Leu Asp Glu Asn Gly Leu Phe Ala Pro Gly
1 5 10 15

Pro Cys

<210> SEQ ID NO 9
<211> LENGTH: 18
<212> TYPE: PRT
<213> ORGANISM: Artificial Sequence
<220> FEATURE:
<223> OTHER INFORMATION: Synthetic

<400> SEQUENCE: 9

Ser Gly Pro Ile Pro Val Leu Asp Glu Asn Gly Leu Phe Ala Pro Gly
1 5 10 15

Pro Ser

-continued

<210> SEQ ID NO 10
<211> LENGTH: 16
<212> TYPE: PRT
<213> ORGANISM: Artificial Sequence
<220> FEATURE:
<223> OTHER INFORMATION: Synthetic

<400> SEQUENCE: 10

Lys Ile Pro Val Leu Asp Glu Asn Gly Leu Phe Ala Pro Gly Pro Cys
1 5 10 15

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Ser Gly Pro Ile Pro Val Leu Asp Glu Asn Gly Leu Phe Ala Pro
1 5 10 15

<210> SEQ ID NO 12
<211> LENGTH: 18
<212> TYPE: PRT
<213> ORGANISM: Artificial Sequence
<220> FEATURE:
<223> OTHER INFORMATION: Synthetic

<400> SEQUENCE: 12

Ala Gly Pro Ile Pro Val Leu Asp Glu Asn Gly Leu Phe Ala Pro Gly
1 5 10 15

Pro Cys

<210> SEQ ID NO 13
<211> LENGTH: 14
<212> TYPE: PRT
<213> ORGANISM: Artificial Sequence
<220> FEATURE:
<223> OTHER INFORMATION: Synthetic

<400> SEQUENCE: 13

Cys Ile Pro Val Leu Asp Glu Asn Gly Leu Phe Ala Pro Cys
1 5 10

<210> SEQ ID NO 14
<211> LENGTH: 19
<212> TYPE: PRT
<213> ORGANISM: Artificial Sequence
<220> FEATURE:
<223> OTHER INFORMATION: Synthetic

<400> SEQUENCE: 14

Cys Gly Pro Pro Glu Ala Arg Asp Glu Gly Thr Ile Thr Leu Glu Arg
1 5 10 15

Gly Pro Cys

<210> SEQ ID NO 15
<211> LENGTH: 18
<212> TYPE: PRT
<213> ORGANISM: Artificial Sequence
<220> FEATURE:
<223> OTHER INFORMATION: Synthetic

<400> SEQUENCE: 15

Ser Gly Pro Ile Pro Val Leu Asp Glu Asn Gly Leu Phe Ala Pro Gly
1 5 10 15

Pro Cys

<210> SEQ ID NO 16
<211> LENGTH: 29
<212> TYPE: PRT
<213> ORGANISM: Artificial Sequence
<220> FEATURE:
<223> OTHER INFORMATION: Synthetic

<400> SEQUENCE: 16

Lys Ile Pro Val Leu Asp Glu Asn Gly Leu Phe Ala Pro Gly Ser Lys
1 5 10 15

Lys Ile Pro Val Leu Asp Glu Asn Gly Leu Phe Ala Pro
20 25

<210> SEQ ID NO 17
<211> LENGTH: 19
<212> TYPE: PRT
<213> ORGANISM: Artificial Sequence
<220> FEATURE:
<223> OTHER INFORMATION: Synthetic

<400> SEQUENCE: 17

Gly Pro Cys Ile Pro Val Leu Asp Glu Asn Gly Leu Phe Ala Pro Cys
1 5 10 15

Gly Pro Lys

<210> SEQ ID NO 18
<211> LENGTH: 19
<212> TYPE: PRT
<213> ORGANISM: Artificial Sequence
<220> FEATURE:
<223> OTHER INFORMATION: Synthetic

<400> SEQUENCE: 18

Cys Gly Pro Ile Pro Val Leu Asp Glu Asn Gly Leu Phe Ala Pro Gly
1 5 10 15

Pro Cys Lys

<210> SEQ ID NO 19
<211> LENGTH: 18
<212> TYPE: PRT
<213> ORGANISM: Artificial Sequence
<220> FEATURE:
<223> OTHER INFORMATION: Synthetic

<400> SEQUENCE: 19

Cys Pro Gly Pro Ala Phe Leu Gly Asn Glu Asp Leu Val Pro Ile Pro
1 5 10 15

Phe Cys